US012668830B2

(12) United States Patent
Typas et al.

(10) Patent No.: US 12,668,830 B2
(45) Date of Patent: Jun. 30, 2026

(54) PHARMACEUTICAL COMPOSITIONS FOR PREVENTION AND/OR TREATMENT OF INFECTIONS AND ANTIBACTERIAL-INDUCED DYSFUNCTIONS

(71) Applicant: EUROPEAN MOLECULAR BIOLOGY LABORATORY, Heidelberg (DE)

(72) Inventors: Athanasios Typas, Heidelberg (DE); Ana Rita Gontao Brochado, Eibelstadt (DE); Stephan Göttig, Neu-Isenburg (DE)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 3 days.

(21) Appl. No.: 18/411,746

(22) Filed: Jan. 12, 2024

(65) Prior Publication Data

US 2024/0175068 A1     May 30, 2024

Related U.S. Application Data

(62) Division of application No. 17/048,735, filed as application No. PCT/EP2019/060017 on Apr. 17, 2019, now Pat. No. 11,926,862.

(30) Foreign Application Priority Data

Apr. 27, 2018     (EP) .................................... 18169989

(51) Int. Cl.
| | |
|---|---|
| *C12Q 1/18* | (2006.01) |
| *A61K 31/11* | (2006.01) |
| *A61K 31/343* | (2006.01) |
| *A61K 31/357* | (2006.01) |
| *A61K 31/445* | (2006.01) |
| *A61K 31/496* | (2006.01) |
| *A61K 31/7036* | (2006.01) |
| *A61K 31/7056* | (2006.01) |
| *A61K 38/12* | (2006.01) |
| *A61K 45/06* | (2006.01) |
| *A61P 31/04* | (2006.01) |

(52) U.S. Cl.
CPC .............. *C12Q 1/18* (2013.01); *A61K 31/11* (2013.01); *A61K 31/343* (2013.01); *A61K 31/357* (2013.01); *A61K 31/445* (2013.01); *A61K 31/496* (2013.01); *A61K 31/7036* (2013.01); *A61K 31/7056* (2013.01); *A61K 38/12* (2013.01); *A61K 45/06* (2013.01); *A61P 31/04* (2018.01)

(58) Field of Classification Search
CPC ........... C12Q 1/18; A61P 31/04; A61K 31/11; A61K 31/343; A61K 31/357; A61K 31/445; A61K 31/496; A61K 31/7036; A61K 31/7056; A61K 38/12; A61K 45/06
USPC .......................................................... 514/32
See application file for complete search history.

(56) References Cited

U.S. PATENT DOCUMENTS

2016/0038438 A1     2/2016   Coates et al.

FOREIGN PATENT DOCUMENTS

| | | |
|---|---|---|
| CN | 103059106 A | 4/2013 |
| CN | 103638524 A | 3/2014 |
| WO | 2008/017734 A1 | 2/2008 |
| WO | 2013103780 A1 | 7/2013 |
| WO | 2014177885 A1 | 11/2014 |
| WO | 2018/035183 A1 | 2/2018 |
| WO | 2018081861 A1 | 5/2018 |

OTHER PUBLICATIONS

Bezerra et al. Vanillin selectively modulates the action of antibiotics against resistant bacteria. Microbial Pathogenesis 113 (2017) 265-268 (Available online Oct. 28, 2017). (Year: 2017).*
Song et al. L-Glycine Alleviates Furfural-Induced Growth Inhibition during Isobutanol Production in *Escherichia coli*. J. Microbiol. Biotechnol. (2017), 27(12), 2165-2172 (First published online Oct. 14, 2017), (Year: 2017).*
Glossary of medical education terms, Institute of International Medical Education. URL: http://iime.org/glossary.htm, (Year: 2013).
Brochado et al. "Species-specific activity of antibacterial drug combinations." Nature vol. 559, pp. 259-263, Jul. 12, 2018.
(Continued)

*Primary Examiner* — Yih-Horng Shiao
(74) *Attorney, Agent, or Firm* — SALIWANCHIK, LLOYD & EISENSCHENK

(57) ABSTRACT

The present invention relates to the field of therapeutics and, more in particular, to pharmaceutical compositions for the prevention and/or treatment of bacterial infections and anti-bacterial-induced dysfunctions. The compositions of the present invention demonstrate high species-specificity in inhibiting the growth of a small number of bacterial species, and most importantly are effective also against multi drug resistant (MDR) clinical isolate species. Interestingly, one of those combinations pairs a non-antibiotic drug, vanillin, with an antibiotic drug, spectinomycin, to demonstrate a surprisingly strong inhibitory effect on the growth of clinically relevant Gram-negative pathogenic and multi-drug resistant *E. coli* isolates. A second set of compounds combines the polymyxin colistin with loperamide, a rifamycin, or a macrolide. Importantly, this invention relates to combinations that enable narrow-spectrum antibacterial therapies, constituting a major effort of current and future drug development efforts in order to prevent major side effects of antibacterial strategies. This invention also relates to pharmaceutical combinations useful to prevent an adverse effect on the gut microbiome, induced by the use of antibacterial compounds.

2 Claims, 45 Drawing Sheets

(56) References Cited

OTHER PUBLICATIONS

Zhao, Kejian (ed.), "Common Knowledge Evidence: Handbook of Practical Drugs." Tianjin Science and Technology Press, pp. 45-46, (Year: 1995).

Tian et al. "Pharmacology." Huazhong University of Science and Technology Press, pp. 231, Jan. 31, 2014.

Chen et al. "New Edition of Clinical Pharmacology." China Traditional Chinese Medicine Press, pp. 58-59, Aug. 31, 2013.

Zeng et al. "Experimental Technology of Grain and Oil Processing." China Agricultural University Press, pp. 189-190, Aug. 31, 2014.

Wang, Feng et al. "In vitro activity of tigecycline in combination with five antibacterial agents against multidrug resistant Acinetobacter baumannii." Therapy on Bacteria Multidrug Resistance, 29(5): 345-349, May 5, 2013.

Fish, Douglas N. "Synergic activity of cephalosporins plus fluoroquinolones against Pseudomonas aeruginosa with resistance to one or both drugs." Journal of Antimicrobial Chemotherapy 50, pp. 1045-1049, (Year: 2002).

* cited by examiner b a - In vitro activity b – *G. mellonella* infections d a a a S. Typhimurium

■ Antagonism ■ Synergy n = 374 interactions

Antibiotic
intracellular concentration:

—— Decreased     —— Not decreased     - - Not tested

PHARMACEUTICAL COMPOSITIONS FOR PREVENTION AND/OR TREATMENT OF INFECTIONS AND ANTIBACTERIAL-INDUCED DYSFUNCTIONS

CROSS-REFERENCE TO RELATED APPLICATIONS

This Application is a Divisional of U.S. Ser. No. 17/048, 735, filed Oct. 19, 2020; which is a National Stage Application of International Application Number PCT/EP2019/060017, filed Apr. 17, 2019; which claims priority to European Application No. 18169989.3, filed Apr. 27, 2018.

FIELD OF THE INVENTION

The present invention relates to the field of therapeutics and, more in particular, to pharmaceutical compositions for the prevention and/or treatment of bacterial infections and antibacterial-induced dysfunctions. The compositions of the present invention demonstrate high species-specificity in inhibiting the growth of a small number of bacterial species, and most importantly are effective also against multi drug resistant (MDR) clinical isolate species. Interestingly, one of those combinations pairs a non-antibiotic drug, vanillin, with an antibiotic drug, spectinomycin, to demonstrate a surprisingly strong inhibitory effect on the growth of clinically relevant Gram-negative pathogenic and multi-drug resistant *E. coli* isolates. A second set of compounds combines the polymyxin colistin with loperamide, a rifamycin, or a macrolide. Importantly, this invention relates to combinations that enable narrow-spectrum antibacterial therapies, constituting a major effort of current and future drug development efforts in order to prevent major side effects of antibacterial strategies. This invention also relates to pharmaceutical combinations useful to prevent an adverse effect on the gut microbiome, induced by the use of antibacterial compounds.

BACKGROUND OF THE INVENTION

The spread of antimicrobial resistance has become a serious public health concern, making once treatable diseases deadly again and undermining breakthrough achievements of modern medicine. Discovery of new antibacterial therapies is imperative, but developing novel drugs takes years and, unfortunately, antibiotic development has stalemated in the last three decades. As a consequence, only a handful of new antibiotic classes have entered the market since the 90's, but none of them is active against Gram-negative pathogens, which currently pose the greatest threat to public health.

In general, antibiotics govern the risk of harming the normal and healthy intestinal flora. This disturbance facilitates bacterial overgrowth and can be the cause of the development of antibiotic resistance in microorganisms. By disrupting the growth cycle of bacteria, antibiotics rapidly select for resistant subpopulations. As such, the rates of nosocomial antibiotic-resistant opportunistic pathogens causing infections have more than doubled in the past decade, and antibiotic resistant bacteria themselves can cause serious infections. As a consequence, a further serious problem governs the possible transfer of resistance factors to other bacteria.

Drug combinations and drug repurposing can act as a first line of defense against the alarming rise of multi-drug resistant (MDR) bacterial infections, e.g. in clinically relevant Gram-negative pathogens, such as *Escherichia coli, Salmonella typhimurium* and *Pseudomonas aeruginosa*. Drug combinations increase the potential therapeutic solution space exponentially, and promising candidates can be swiftly moved to clinical applications, when individual compounds are already approved or used.

Multidrug therapies are common in many diseases, but are largely unexplored for bacterial infections. Antibiotic combinations pose not only opportunities but also challenges. One such challenge is that proper interaction assessment requires mixing several concentrations of each drug in a checkerboard format. This requirement for rigorous testing renders systematic interaction studies difficult. As a consequence, the current knowledge is sparse and comes from many independent studies, each testing a few pairwise combinations with diverse assays and metrics.

To identify general principles for antibacterial drug combinations, drug-drug interactions have to be systematically profiled across different strains and species. Previous large-scale studies had to make compromises either at the drug or the species/strain level. Having as main goal to identify antibiotic adjuvants, most studies profiled combinations of a single antibiotic with 1,000-2,000 previously approved drugs, or even larger chemical libraries.

Although a number of species have been profiled this way, including *Escherichia coli, Pseudomonas aeruginosa* and *Staphylococcus aureus*, the screen design (probing only for synergies in single drug-doses) hampers comparative analyses. Smaller screens have been performed in which both synergies and antagonisms can be quantified, but were confined to *E. coli*, where pairwise combinations of 21 antibiotics at a single concentration were tested. Larger-scale screens exist for antifungals, but also suffer from similar limitations: for example, the largest dose-dependent profiling of combinations is that of ~200 drug pairs in Saccharomyces cerevisiae, whereas many more pairs have recently been tested in different fungal species, albeit at single drug dose combinations.

The development and spread of antibacterial resistance governs one of the most serious threats to public health, generating bacterial strains against which known antibacterial compounds are inefficient. Thus, there is a need to provide novel antibacterial pharmaceutical compositions that can overcome bacterial antibiotic resistance by being effective against a selective bacterial strain. Such narrow-spectrum antibacterial therapies could conquer major problems of current antibacterial strategies, such as mitigating antibiotic resistance spread and side effects caused by the adverse impact of compounds on healthy microorganisms residing in the patients' body.

It is therefore an object of the present invention to provide novel antibacterial pharmaceutical compositions. It is a further object of this invention to offer antibacterial pharmaceutical compositions, which are effective against multidrug resistant (MDR) bacterial strains, e.g. clinically relevant Gram-negative pathogens, such as *Escherichia coli, Salmonella typhimurium* and *Pseudomonas aeruginosa*. A further object of the present invention is the development of antibacterial therapies that can prevent the development of antibiotic resistant bacteria as well as the adverse impact of compounds on healthy microorganisms residing in the patients' body, such as the gut microbiota.

The problem of the present invention is solved by providing a method to systematically screen and assess drug-drug interactions in different strains and species of clinically-relevant Gram-negative bacteria. The results of the screen provide multiple synergistic pairs of compounds, which demonstrate strong antibacterial activity, or antagonistic pairs, which can be used as an antidote treatment strategy to prevent damage induced by the use of antibiotics, e.g. on the healthy microbiome. Some of those combinations of compounds exhibit great species-specificity in inhibiting the growth of a single species of bacteria, most importantly being effective also against MDR clinical isolate species. Compared to broad spectrum antibacterial therapies, such selective pharmaceutical compositions are far less likely to select for antimicrobial resistance as well as less harmful for the patients' intestinal flora.

The inventors of the present invention have found that some of the pharmaceutical pairs identified with the method described in the present invention contain non-antibiotic compounds such as food additives, like vanillin. Importantly, such combinations enable narrow-spectrum antibacterial therapies, constituting a major effort of current and future drug development in order to prevent major side effects of antibacterial strategies. Other objects of the present invention will become apparent to the person of skill when studying the specification of the present invention.

In a first aspect thereof, the object of the present invention is solved by providing a method for identifying a synergistic antibacterial effect of at least two drug compounds on a bacterium, the method comprising
a) providing said bacterium to be tested for said antibacterial effect;
b) selecting said at least two drug compounds, wherein at least one of said drug compounds is known to have an antibacterial effect on said bacterium of a), and wherein said at least one other drug compound is selected from
(i) an antibiotic, or a pharmaceutically acceptable salt thereof, wherein said antibiotic is known to belong to the same class and/or to target the same bacterial cellular process as the first selected drug compound, and
(ii) a human-targeted drug, a food additive, or a pharmaceutically acceptable salt thereof;
c) identifying a synergistic antibacterial effect of said at least two drug compounds in said bacterium; and
d) selecting said at least two drug compounds as identified in step c).

As used herein, "synergy" or "synergistic effect" refers to the effect that occurs when at least two compounds interact, and result in an overall effect that is greater than the sum of individual effects of either of said compounds used alone. This combination thus greatly improves the antibacterial effect of one of the compounds used alone. Stated another way, synergistic effect means that the total antibacterial effect against a bacterium or a bacterial species of the combination of the two components is greater than the sum of the antibacterial effect of each component when measured separately.

As used herein, "antagonism" or "antagonistic effect" refers to the effect that occurs when at least two compounds interact, and result in an overall effect that is lower than the sum of individual effects of either of them used alone. An "antagonistic" combination, as used herein, can prevent the antibacterial effect of one of the compounds used alone. Stated another way, antagonistic effect means that if at least one of the compounds is having an antibacterial effect against a bacterium or a bacterial species, this antibacterial effect can be counteracted by the at least one other compound. The at least one other compound can thus be seen as an "antidote" to said first compound. The combination of the at least two compounds is referred to as having an "antagonistic effect" if the antibacterial effect of at least one of the two compounds is masked when used in combination with the other compound.

"Synergistic" and "antagonistic" effects are scored by permutation p-values as described below in the "Methods" section of this description.

"Human-targeted drug", in the context of the present invention, shall refer to a compound intended for the use in humans. Preferably, the mechanism of action (MOA) of said drug is known and may affect a human cell intracellularly, extracellularly, or within the human cell membrane. The use of said human-targeted drug may suffer from the fact that it has side effects harming a human cell or organism. Examples of such human-targeted drugs include, without being limited thereto, antipsychotics, anesthetics, acid-reducing medications, chemotherapy drugs, and blood-pressure medications. Contrary, the term "antibiotic", in the context of the present invention, shall refer to a compound that is preferably microbiologically active, i.e. for use against pathogenic/undesired microbes.

The object of the present invention is further solved by providing a method for identifying an antagonistic antibacterial effect of at least two drug compounds on a bacterium, the method comprising
a) providing a first bacterium to be tested for said antibacterial effect;
b) selecting said at least two drug compounds, wherein at least one of said drug compounds is known to have an antibacterial effect on a second bacterium, and wherein said at least one other drug compound is selected from an antibiotic, a human-targeted drug, a food additive, or a pharmaceutically acceptable salt thereof, preferably wherein said at least one other drug compound is known to belong to a different class and/or to target a different bacterial cellular process as the first selected drug compound;
c) identifying an antagonistic antibacterial effect of said at least two drug compounds in said first bacterium of a); and
d) selecting said at least two drug compounds as identified in step c).

Preferably, said first bacterium of a) and said second bacterium of b) belong to a different bacterial genus and/or different bacterial species.

Preferred are the afore-mentioned methods, wherein said bacterium is a Gram-positive bacterium or a Gram-negative bacterium, and wherein said bacterium is a member of the *Enterobacter, Escherichia, Shigella, Serratia, Proteus, Pseudomonas, Acinetobacter, Staphylococcus, Streptococcus, Pseudomonas, Salmonella, Helicobacter, Citrobacter, Treponema, Mycobacterium, Bordetella, Borrelia, Brucella, Corynebacteria, Fusobacterium, Leptospira, Listeria, Pasteurella, Rickettsia, Faecalibacteria, Eggerthella, Lactonifactor, Coliform, Bacillus, Franscicella, Acinetobacter, Legionella, Actinobacillus, Coxiella, Bifidobacteria, Mobiluncus, Enterococcus, Actinomyces, Neisseria, Chlamydia, Vibrio, Diplococcus, Lactobacillus, Kingella, Yersinia, Klebsiella, Bacteroides, Eubacterium, Alistipes, Ruminococcus, Roseburia, Parabacteroides, Prevotella, Coprococcus, Dorea, Blautia, Odoribacter, Clostridia, Collinsella, Bilophila, Akkermansia, Veillonella, Haemophilus, Desulfovibrio, Butyrivibrio*, and/or *Campylobacter* genus, or any related genus thereof, optionally wherein said bacterium is an antibiotic-resistant bacterium, in particular a multi drug resistant strain thereof.

Further preferred is the afore-mentioned method for identifying an antagonistic antibacterial effect of at least two drug compounds on a bacterium, wherein said first bacterium to be tested for said antibacterial effect is a commensal bacterium and/or a probiotic bacterium, such as a member of the *Enterobacter, Staphylococcus, Streptococcus, Pseudomonas, Escherichia, Helicobacter, Neisseria, Campylobacter, Clostridia, Citrobacter, Vibrio, Treponema, Mycobacterium, Klebsiella, Actinomyces, Bacteroides, Bordetella, Brucella. Corynebacteria, Diplococcus, Fusobacterium, Leptospira, Pasteurella, Proteus, Rickettsia, Faecalibacteria, Shigella, Parabacteroides, Odoribacter, Collinsella, Eggerthella, Lactonifactor, Roseburia, Coliform, Bacillus, Franscicella, Acinetobacter. Legionella, Actinobacillus, Coxiella, Kingella kingae, Haemophilus, Bifidobacteria, Mobiluncus, Prevotella, Akkermansia, Bilophila, Blautia, Coprococcus, Dorea, Eubacteria, Lactobacillus, Ruminococcus, Veillonella,* and/or *Enterococcus* genus.

Further preferred is the afore-mentioned method for identifying an antagonistic antibacterial effect of at least two drug compounds on a bacterium, wherein said second bacterium is a pathogenic bacterium, such as a member of the *Enterobacter, Escherichia, Shigella, Serratia, Proteus, Pseudomonas, Acinetobacter, Staphylococcus, Pseudomonas, Salmonella, Helicobacter, Citrobacter, Treponema, Mycobacterium, Bordetella, Borrelia, Brucella, Corynebacteria, Fusobacterium, Leptospira, Listeria, Pasteurella, Rickettsia, Faecalibacteria, Eggerthella. Lactonifactor, Coliform, Bacillus, Franscicella, Acinetobacter, Legionella, Actinobacillus, Coxiella, Bifidobacteria, Mobiluncus, Enterococcus, Actinomyces, Neisseria, Chlamydia, Vibrio, Diplococcus, Lactobacillus, Kingella, Yersinia,* and/or *Klebsiella* genus.

Importantly, said method for identifying an antagonistic antibacterial effect of at least two drug compounds on a bacterium is used to identify an antagonistic antibacterial effect of said at least two drug compounds in said first bacterium, wherein said first bacterium is a commensal bacterium and/or a probiotic bacterium, while said at least two drug compounds are having an antibacterial effect on a second bacterium, wherein said second bacterium is a pathogenic bacterium. Thus, the at least two drug compounds are having an antibacterial effect on a pathogenic bacterium, while preventing and/or relieving collateral damage to a commensal bacterium and/or a probiotic bacterium. The use of said at least two drug compounds is thus advantageous over using one of the compounds alone, since the combination of compounds is preventing the damage of said compound having an antibacterial effect on a commensal bacterium and/or a probiotic bacterium.

A further aspect of the present invention then relates to a method for developing a targeted therapy for use in the prevention and/or treatment of bacterial infections, the method comprising:
   a) performing the afore-described method;
   b) identifying a selective antibacterial effect of the combination of said at least two drug compounds on a bacterium, and
   c) selecting said at least two drug compounds as identified in step b).

A further preferred aspect of this invention is a method for producing an antibacterial pharmaceutical composition, comprising:
   a) performing the afore-described method, and
   b) formulating said combination as selected into an antibacterial pharmaceutical composition.

Yet another aspect of the present invention relates to an antibacterial pharmaceutical composition, produced according to the afore-mentioned method.

The present invention also relates to a method for preventing an adverse effect on a gut microbiome using the antibacterial pharmaceutical composition of this invention, wherein at least one of the components of said composition is having an antibacterial effect on at least a first bacterial species and a second bacterial species, and wherein at least one other component is preventing said antibacterial effect on said first bacterial species.

Further preferred is the afore-mentioned method for preventing an adverse effect on a gut microbiome using the antibacterial pharmaceutical composition of this invention, wherein said first bacterium to be tested for said antibacterial effect is a commensal bacterium and/or a probiotic bacterium, such as a member of the *Enterobacter, Staphylococcus, Streptococcus, Pseudomonas, Escherichia, Helicobacter, Neisseria, Campylobacter, Clostridia, Citrobacter, Vibrio, Treponema, Mycobacterium, Klebsiella, Actinomyces, Bacteroides, Bordetella, Brucella, Corynebacteria, Diplococcus, Fusobacterium, Leptospira, Pasteurella, Proteus, Rickettsia, Shigella, Parabacteroides, Odoribacter, Faecalibacteria, Collinsella, Eggerthella, Lactonifactor, Roseburia, Coliform, Bacillus, Franscicella, Acinetobacter, Legionella, Actinobacillus, Coxiella, Kingella kingae, Haemophilus, Bifidobacteria, Mobiluncus, Prevotella, Akkermansia, Bilophila, Blautia, Coprococcus, Dorea, Eubacteria, Lactobacillus, Ruminococcus, Veillonella,* and/or *Enterococcus* genus.

Said at least one first bacterial species can be 1 bacterial species, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 other bacterial species, or any number of commensal and/or probiotic bacterial species.

Additionally preferred is the afore-mentioned method for preventing an adverse effect on a gut microbiome using the antibacterial pharmaceutical composition of this invention, wherein said second bacterium is a pathogenic bacterium, such as a member of the *Enterobacter, Escherichia, Shigella, Serratia, Proteus, Pseudomonas, Acinetobacter, Staphylococcus, Streptococcus, Pseudomonas, Salmonella, Helicobacter, Citrobacter, Treponema, Mycobacterium, Bordetella, Borrelia, Brucella, Corynebacteria, Fusobacterium, Leptospira, Listeria, Pasteurella, Rickettsia, Faecalibacteria, Eggerthella, Lactonifactor, Coliform, Bacillus, Franscicella, Acinetobacter, Legionella, Actinobacillus, Coxiella, Bifidobacteria, Mobiluncus, Enterococcus, Actinomyces, Neisseria, Chlamydia, Vibrio, Diplococcus, Lactobacillus, Kingella, Yersinia,* and/or *Klebsiella* genus.

The invention is additionally solved by providing a method for preventing the development and/or spread of an antibacterial resistance using an antibacterial pharmaceutical composition of this invention.

An additional aspect of the present invention relates to an antibacterial pharmaceutical composition, comprising
   (i) vanillin or a pharmaceutically acceptable salt thereof, or a vanillin derivative or a pharmaceutically acceptable salt thereof, and
   (ii) at least one antibacterial drug compound or a pharmaceutically acceptable salt thereof.

Preferred is the afore-mentioned antibacterial pharmaceutical composition, wherein said at least one anti-bacterial drug compound or the pharmaceutically acceptable salt thereof is selected from an aminoglycoside, a macrolide, a penicillin, a tetracycline, a lincosamide, a quinolone, a fluoroquinolone, a beta-lactam, a polymixin, a monobactam, a glycylcycline, an ansamycin, a sulphonamide, an oxazolidinone, a carbacefem, a carbapenem, a cephalosporinc, a strepotgramin, a glycopeptide, a polypeptide, an arsphenamine, chloramphenicol, clindamycin, lincomycin, daptomycin, trimethoprim, novobiocin, ethambutol, fosfomycine, fusidic acid, furazolidone, isoniazid, linezolide, metronidazole, mupirocin, nitrofurantoin, platensimycine, pyrazinamide, quinupristine, dalfopristine, rifampine, a rifamycin, such as rifampicin, rifabutin, or rifaximin, tinidazole, viomycin, and capreomycin, or a pharmaceutically acceptable salt thereof, in particular an aminoglycoside selected from streptomycin, dihydrostreptomycin, amikacin, apramycin, arbekacin, astromicin, bekanamycin, dibekacin, framycetin, gentamicin, hygromycin, isepamicin, kanamycin, neomycin, netilmicin, paromomycin, rhodostreptomycin, ribostamycin, sisomycin, spectinomycin, tobramycin, vancomycin, and verdamicin, or a pharmaceutically acceptable salt thereof, preferably spectinomycin, or a pharmaceutically acceptable salt of spectinomycin.

The present invention also relates to an antibacterial pharmaceutical composition comprising (i) A polymixin selected from colistin and polymyxin B, or a pharmaceutically acceptable salt thereof, preferably colistin or a pharmaceutically acceptable salt of colistin, and (ii) At least one other drug compound or a pharmaceutically acceptable salt thereof, wherein said at least one other drug compound, or the pharmaceutically acceptable salt thereof, is selected from loperamide, a rifamycin, such as rifampicin, rifabutin, or rifaximin, a macrolide, an aminoglycoside, a penicillin, a tetracycline, a lincosamide, a quinolone, a fluoroquinolone, a beta-lactam, a polymixin, a monobactam, a glycylcycline, an ansamycin, a sulphonamide, an oxazolidinone, a carbacefem, a carbapenem, a cephalosporine, a strepotgramin, a glycopeptide, a polypeptide, an arsphenamine, chloramphenicol, clindamycin, lincomycin, daptomycin, trimethoprim, novobiocin, ethambutol, fosfomycine, fusidic acid, furazolidone, isoniazid, linezolide, metronidazole, mupirocin, nitrofurantoin, platensimycine, pyrazinamide, quinupristine, dalfopristine, rifampine, tinidazole, viomycin, and capreomycin, or a pharmaceutically acceptable salt thereof, preferably wherein said one other drug compound is loperamide, a rifamycin, such as rifampicin, rifabutin, or rifaximin, or a macrolide, such as erythromycin, azithromycin, clarithromycin, or roxithromycin, or a pharmaceutically acceptable salt thereof.

The invention is also solved by providing an antibacterial pharmaceutical composition, comprising (i) An antibacterial compound selected from an aminoglycoside, a macrolide, a penicillin, a tetracycline, a lincosamide, a quinolone, a fluoroquinolone, a beta-lactam, a polymixin, a monobactam, a glycylcycline, an ansamycin, a sulphonamide, an oxazolidinone, a carbacefem, a carbapenem, a cephalosporine, a strepotgramin, a glycopeptide, a polypeptide, an arsphenamine, chloramphenicol, clindamycin, lincomycin, daptomycin, trimethoprim, novobiocin, ethambutol, fosfomycine, fusidic acid, furazolidone, isoniazid, linezolide, metronidazole, mupirocin, nitrofurantoin, a rifamycin, such as rifampicin, rifabutin, or rifaximin, platensimycine, pyrazinamide, quinupristine, dalfopristine, rifampine, tinidazole, viomycin, and capreomycin, or a pharmaceutically acceptable salt thereof, and (ii) at least one other drug compound selected from an antibiotic, a human-targeted drug, a food additive, or a pharmaceutically acceptable salt thereof, preferably wherein said one other drug compound is procaine, metformin, benzalkonium, berberine, erythromycin, clarithromycin, aztreonam, loperamide, pyocyanin, phenazine methosulfate, clindamycin, a rifamycin, such as rifampicin, rifabutin, or rifaximin, paraquat, trimethoprim, doxycycline, curcumin, vanillin, caffeine, acetylsalisylic acid, epigallocatechin gallate, CHIR090, minocycline, spectinomycin, and fosfomycin, or a pharmaceutically acceptable salt thereof, optionally, wherein said antibacterial compound from (i) is having an antibacterial effect on at least a first bacterium and a second bacterium, and wherein said compound from (ii) is antagonizing said antibacterial effect of said compound from (i) on said at least one first bacterium, and wherein said compound from (ii) is not antagonizing said antibacterial effect of said compound from (i) on said second bacterium.

"Antagonizing", in the context of the present invention, refers to having an "antagonistic effect". Stated another way, antagonistic effect means that if at least one of the compounds is having an antibacterial effect against a bacterium or a bacterial species, this antibacterial effect is counteracted, i.e. "antagonized", by the at least one other compound.

Further preferred is the afore-mentioned antibacterial pharmaceutical composition, wherein said first bacterium is a commensal bacterium and/or a probiotic bacterium, such as a member of the *Enterobacter, Staphylococcus, Streptococcus, Pseudomonas, Escherichia, Helicobacter, Neisseria, Campylobacter, Clostridia, Citrobacter, Vibrio, Treponema, Mycobacterium, Klebsiella, Actinomyces, Bacteroides, Bordetella, Brucella, Corynebacteria, Diplococcus, Fusobacterium, Leptospira, Pasteurella, Proteus, Rickettsia, Shigella, Parabacteroides, Odoribacter, Faecalibacteria, Collinsella, Eggerthella, Lactonifactor. Roseburia, Coliform, Bacillus. Franscicella, Acinetobacter, Legionella, Actinobacillus, Coxiella, Kingella kingae, Haemophilus, Bifidobacteria, Mobiluncus, Prevotella, Akkermansia, Bilophila, Blautia, Coprococcus, Dorea, Eubacteria, Lactobacillus, Ruminococcus, Veillonella*, and/or *Enterococcus* genus.

Additionally preferred is the afore-mentioned pharmaceutical composition, wherein said second bacterium is a pathogenic bacterium, such as a member of the *Enterobacter, Escherichia, Shigella, Serratia, Proteus, Pseudomonas, Acinetobacter, Staphylococcus, Streptococcus, Pseudomonas, Salmonella, Helicobacter, Citrobacter, Treponema, Mycobacterium, Bordetella, Borrelia, Brucella, Corynebacteria, Fusobacterium, Leptospira, Listeria, Pasteurella, Rickettsia, Faecalibacteria, Eggerthella, Lactonifactor, Coliform, Bacillus, Franscicella, Acinetobacter, Legionella, Actinobacillus, Coxiella, Bifidobacteria, Mobiluncus, Enterococcus, Actinomyces, Neisseria, Chlamydia, Vibrio, Diplococcus, Lactobacillus, Kingella, Yersinia*, and/or *Klebsiella* genus.

Optionally, said compound from (ii) is antagonizing said antibacterial effect of said compound from (i) on 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 other bacterial species, or any number of other bacterial species.

The afore-mentioned compositions of compounds can generally be used in a wide variety of medical applications, in particular in the prevention and/or treatment of bacterial infections and/or dysbiosis. Preferred is the afore-mentioned composition, wherein said composition is for use in the prevention and/or treatment of a bacterial infection, wherein said bacterial infection is selected from an infection of the gastrointestinal tract, an infection of the urogenital tract, an infection of the upper and lower respiratory tract, rhinitis, tonsillitis, pharyngitis, bronchitis, pneumonia, an infection of the inner organs, nephritis, hepatitis, peritonitis, endo- carditis, meningitis, osteomyelitis, an infection of the eyes, an infection of the ears, a cutaneous infection, a subcutane- ous infection, an infection after burn, diarrhea, colitis, pseudomembranous colitis, a skin disorder, toxic shock syndrome, bacteremia, sepsis, pelvic inflammatory disease, an infection of the central nervous system, wound infection, intra-abdominal infection, intravascular infection, bone infection, joint infection, acute bacterial otitis media, pyelo- nephritis, deep-seated abscess, and tuberculosis.

Further preferred is the afore-mentioned composition, wherein said bacterial infection to be treated and/or pre- vented is caused by a Gram-negative bacterium, preferably wherein said Gram-negative bacterium is a gamma-proteo- bacterium, such as a member of the Enterobacteriaccae or the Moraxellaceae family, for example a member of the *Enterobacter, Escherichia, Salmonella, Klebsiella, Yersinia, Shigella, Serratia, Proteus, Pseudomonas,* and/or *Acineto- bacter* genus, or any related genus thereof, optionally wherein said bacterium is an antibiotic-resistant bacterium, in particular a multi drug resistant strain thereof.

Importantly, many bacterial species residing in a person's or a patient's body are commensal or probiotic bacterial species. Compounds having an antibiotic effect are often also effective against these commensal or probiotic bacterial species, thereby damaging e.g. the healthy gut microbiome. It is thus important to prevent such a damaging effect on commensal and/or probiotic bacteria, while simultaneously enabling an antibiotic effect on pathogenic bacteria that are responsible for an infection and/or a disease.

The term "microbiota" refers, collectively, to the entirety of microbes found in association with a higher organism, such as a human. Organisms belonging to a human's micro- biota may generally be categorized as bacteria, archaea, yeasts, and single-celled eukaryotes, as wells as viruses and various parasites.

The term "microbiome" refers, collectively, to the entirety of microbes, their genetic elements (genomes), and envi- ronmental interactions, found in association with a higher organism, such as a human.

The microbiome comprises many commensal and/or pro- biotic bacterial strains. The term "commensal" refers to organisms that are normally harmless to a host, and can also establish mutualistic relations with the host. The human body contains about 100 trillion commensal organisms, which have been suggested to outnumber human cells by a factor of 10.

The term "probiotic" as used herein means living micro- organisms, which when administered in adequate amounts, confer a health benefit on the host. Probiotics may be available in foods and dietary supplements (for example, but not limited to capsules, tablets, and powders). Examples of food containing probiotics are yogurt, fermented and unfer- mented milk, miso, tempeh, and some juices and soy bev- erages. Some bacterial strains of the microbiome are known to have a probiotic function, such as *Lactobacillus, Bifido- bacterium, Enterococcus, Streptococcus, Pediococcus, Leu- conostoc, Bacillus, Escherichia,* and *Lactococcus.*

The term "dysbiosis" (also called dysbacteriosis) shall refer to any kind of imbalance of the microbiome. For example, species that are normally underrepresented in the microbiome of a healthy human being become overrepre- sented during the condition of dysbiosis, whereas normally dominated species of a healthy human being become under- represented during the condition of dysbiosis. Most often, dysbiosis is a condition in the gastrointestinal tract, particu- larly during small intestinal bacterial overgrowth (SIBO) or small intestinal fungal overgrowth (SIFO). Dysbiosis has been reported to be associated with illnesses, such as inflam- matory bowel disease, bacterial vaginosis, and colitis.

Yet another embodiment of the invention pertains to the afore-described composition for use, wherein said compo- nents of said composition are administered to a subject simultaneously, separately or sequentially, wherein said sub- ject is a mammal, such as a human, preferably a human patient, optionally wherein said composition is in liquid, dry or semi-solid form, such as, for example, in the form of a tablet, coated tablet, effervescent tablet, capsule, powder, granulate, sugar-coated tablet, lozenge, pill, ampoule, drop, suppository, emulsion, ointment, gel, tincture, paste, cream, moist compress, gargling solution, plant juice, nasal agent, inhalation mixture, aerosol, mouthwash, mouth spray, nose spray, or room spray.

The invention will now be described further in the fol- lowing examples with reference to the accompanying fig- ures, nevertheless, without being limited thereto. For the purposes of the present invention, all references as cited are incorporated by reference in their entireties.

Figure 1:
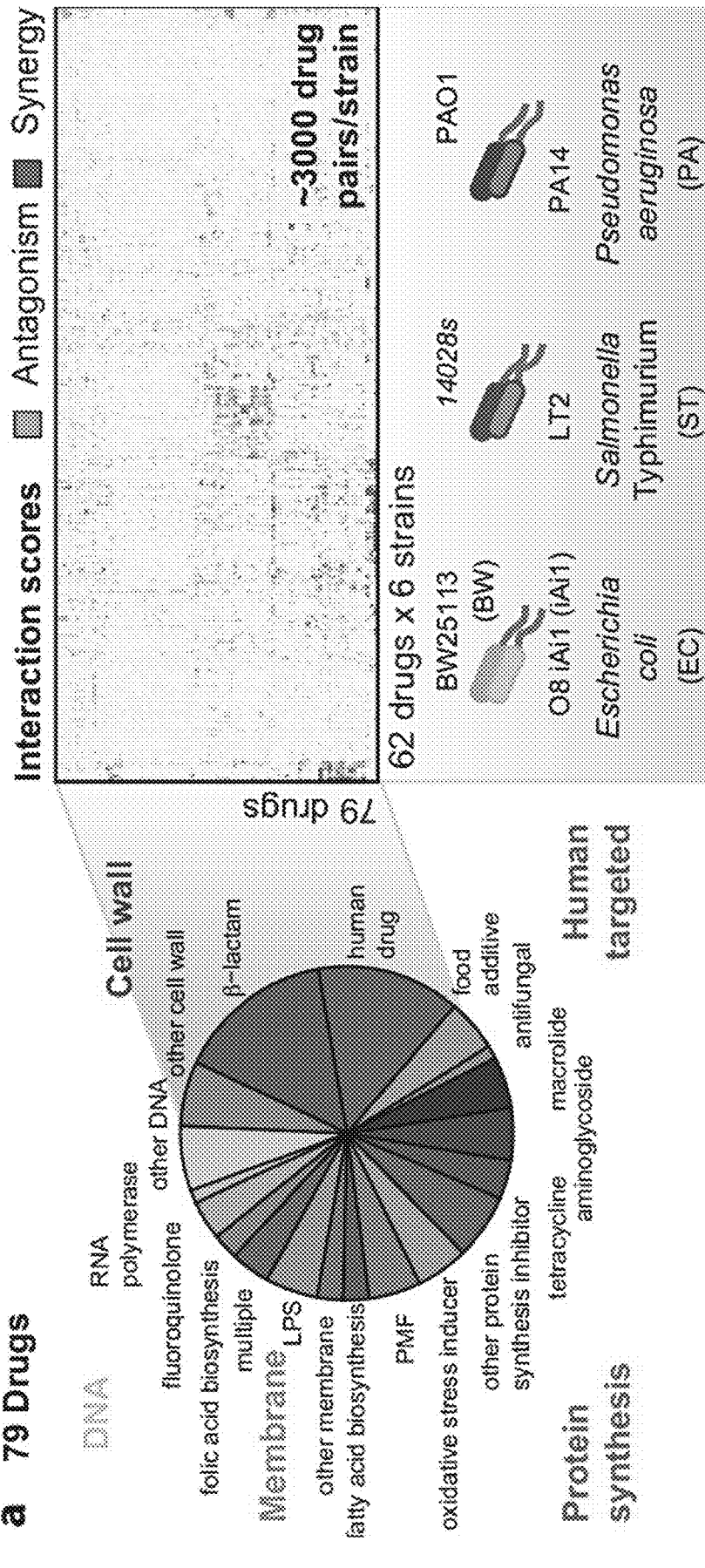
FIG. 1 shows high-throughput profiling of pairwise drug combinations in Gram-negative bacteria. a) Drug and spe- cies selection for the screen. The 79 drugs used in the combinatorial screen are grouped to categories. Antibacte- rials are grouped by target with the exception of antibiotic classes for which enough representatives were screened (>2) to form a separate category: ß-lactams, macrolides, tetracy- clines, fluoroquinolones and aminoglycosides. Classifica- tion of human-targeted drugs and food additives is not further refined, because the MoA is unclear for most. A subset of 62 arrayed drugs were profiled against the com- plete set of 79 drugs in 6 strains. Strains are color coded according to species. b) Quantification of drug-drug inter- actions. Growth was profiled by measuring optical density (OD595 nm) over time in the presence of no, single and both drugs. Interactions were defined according to Bliss indepen- dence. Significantly lower or higher fitness than expectation (fa*fq) indicates synergy or antagonism, respectively. Syn- ergy and antagonism were assessed by growth in 4×4 checkerboards.
Figure 1:
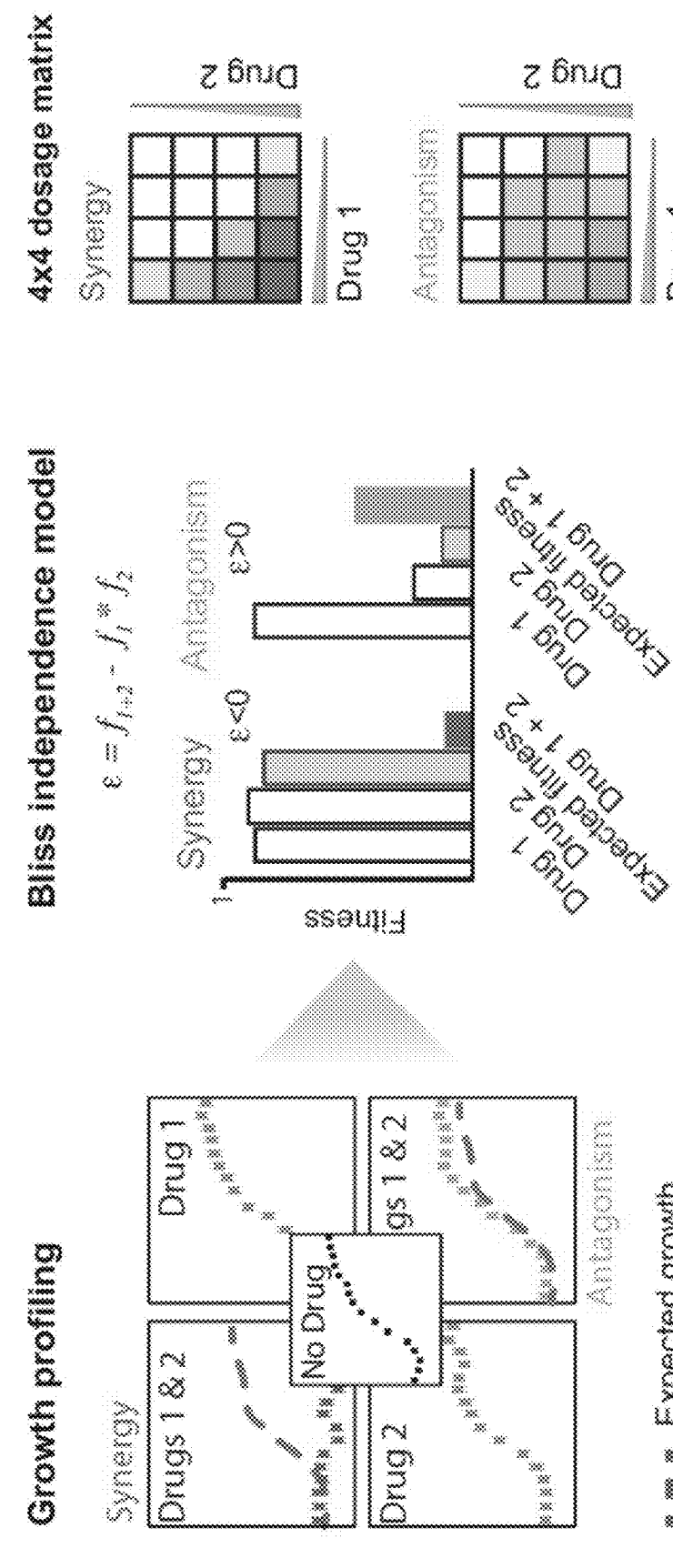

The term "infection", as used in the context of the present invention, relates to the presence of bacteria, viruses, fungi, protozoa or other microorganisms, in or on a subject as well as the invasion by bacteria, viruses, fungi, protozoa or other microorganisms. The invasion includes undesired prolifera-tion of pathogenic microbes in a host organism. More generally, a microbial infection can be any situation in which the presence of a microbial population(s) is damaging to a host animal. Thus, a microbial infection exists when exces-sive microorganisms are present in or on a mammal's body, or when the effects of the presence of a microbial population(s) is damaging the cells or other tissue of a mammal. Thus, the inhibition of the growth of such invading microorganisms results in a benefit to the subject that is infected by the microbial population(s). Examples of bac-terial infections are urinary tract infection (UTI), kidney infections (pyelonephritis), gynecological and obstetrical infections, respiratory tract infection (RTI), acute exacerba-tion of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, chlamydia, skin infections, bacteremia.

Said infection to be prevented and/or treated by the compositions of the present invention is preferably caused by a Gram-negative bacterium, wherein said Gram-negative bacterium is a gamma-proteobacterium, such as a member of the Enterobacteriaccae or the Moraxellaceae family, for example a member of the *Enterobacter, Escherichia, Salmonella, Klebsiella, Yersinia, Shigella, Serratia, Proteus, Pseudomonas,* and/or *Acinetobacter* genus, optionally wherein said bacterium is an antibiotic-resistant bacterium, in particular a multi drug resistant strain thereof.

The term "antibiotic", as used herein, relates to a chemical substance which at low concentrations kills or prevents the growth of certain microorganisms, generally bacteria, although some antibiotics are also used for the treatment of infections by fungi or protozoa. Antibiotics are used in human, animal or horticultural medicine to treat infections caused by microorganisms. Antibiotics included in the present invention are, without limitation, aminoglycoside antibiotics, polymyxins, oxazolidinones, strepotgramins, ansamycins, carbacefem, carbapenems, cephalosporins, glycopeptides, glycylcyclines, macrolides, monobactams, penicillins, polypeptides, quinolones, fluoroquinolones, sulphonamides, beta-lactams, tetracyclines and others such as vancomycin, daptomycin, trimethoprim, novobiocin, arsphenamine, chloramphenicol, clindamycin, lincomycin, ethambutol, fosfomycin, fusidic acid, furazolidone, isoniazid, metronidazole, mupirocin, nitrofurantoin, platensimycin, pyrazinamide, polymixins, quinupristin/dalfopristin, a rifamycin, such as rifampicin, rifabutin, or rifaximin, tinidazole, viomycin and capreomycin.

The term "pharmaceutical composition" refers to a preparation which is in such form as to permit the biological activity of an active ingredient contained therein to be effective, and which contains no additional components which are unacceptably toxic to a subject to which the composition would be administered. A pharmaceutical composition of the present invention can be administered by a variety of methods known in the art. As will be appreciated by the skilled artisan, the route and/or mode of administration will vary depending upon the desired results. Pharmaceutically acceptable diluents include saline and aqueous buffer solutions. A "pharmaceutically acceptable carrier" refers to an ingredient in a pharmaceutical formulation, other than an active ingredient, which is nontoxic to a subject. Pharmaceutically acceptable carriers include any and all solvents, dispersion media, coatings, antibacterial and antifungal agents, isotonic and absorption delaying agents, and the like that are physiologically compatible. The carrier can be suitable for intravenous, intramuscular, subcutaneous, parenteral, spinal or epidermal administration (e.g. by injection or infusion).

The pharmaceutical compositions according to the invention may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection, and infusion. Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient, which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, in one embodiment the carrier is an isotonic buffered saline solution. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. A typical dose can be, for example, in the range of 0.001 to 1000 μg; however, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. The compositions of the invention may be administered locally or systemically. Administration will generally be parenterally, e.g., intravenously; the pharmaceutical composition may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as interleukins or interferons depending on the intended use of the pharmaceutical composition.

In context of the present invention, the term "subject", as used in certain embodiments, preferably refers to a mammal, such as a mouse, rat, guinea pig, rabbit, cat, dog, monkey, or preferably a human. The term "patient" preferably refers to a mammal, such as a mouse, rat, guinea pig, rabbit, horse, cattle, cow, cat, dog, monkey, or preferably a human, for example a human patient, for whom diagnosis, prognosis, or therapy is desired. The subject of the invention may be at danger of suffering from a disease, such as a bacterial infection, a viral infection, a fungal infection, and a parasitic infection. A more detailed description of medical indications relevant in context of the invention is provided herein elsewhere.

The term "treating" as used herein means stabilizing or reducing an adverse symptom associated with a condition; reducing the severity of a disease symptom; slowing the rate of the progression of a disease; inhibiting or stabilizing the progression of a disease condition; or changing a metric that is associated with the disease state in a desirable way.

EXAMPLES

In order to consistently and systematically assess drug-drug interactions in clinically-relevant Gram-negative bacteria, the inventors screened 79 drugs alone and in pairwise combinations in six strains of three different species by using 4×4 checkerboards assays. The inventors obtained nearly 3,000 drug combinations per strain, which allowed the inventors to detect a number of general principles of drug-drug interactions. These included that: i) interactions are largely species specific with synergies being less frequent but more conserved; and ii) antagonisms occur exclusively between drugs targeting different processes, whereas synergies are common for drugs targeting the same process. The inventors further demonstrate that antagonisms are often caused by decreasing intracellular drug concentrations, and that a number of synergies are also effective against multi-drug and extensively-drug resistant (MDR and XDR) clinical isolates. Finally, the inventors used their data to investigate the interaction mechanisms of vanillin, which on its own has no antibacterial activity, but in combination antagonizes many drugs and specifically synergizes with spectinomycin against E. coli.

The inventors have profiled nearly 3,000 pairwise drug combinations in a dose-dependent manner in three different Gram-negative bacteria, all relevant for difficult-to-treat infections. In total, the inventors identified >2,500 synergies and antagonisms in the 6 strains tested, accounting for ~15% of the screened combinations. This quantitative and comprehensive dataset enabled the inventors to derive general principles behind drug-drug interactions, address conservation across species, and discover potent synergies that are also effective against MDR clinical isolates of the same or closely-related species.

Three general principles emerge from the inventors' data. First, drug-drug interactions are highly species-specific, even if the individual drugs have the same cellular targets across species. This is likely because the underlying mechanisms behind drug-drug interactions are not conserved. Such mechanisms are dependent both on the intracellular wiring between the targeted processes, and on modulating the uptake/efflux of the combined drugs. Inter-process wiring seems to be little conserved even among closely-related microbial species, and both uptake and drug efflux depend on the most diverse part of a bacterial cell: its envelope, harboring redundant transport systems, and assembly machineries/enzymes. Multiple consequences of the species-specificity of drug-drug interactions exist. For antibacterials, this means that narrow-spectrum therapies, constituting a major effort of current and future drug development, can come from synergistic combinations of already approved drugs. On the other hand, species-specific antagonisms can be used to mitigate the collateral damage of antibiotic therapies to the gut microbiota. As non-antibiotic drugs also take a high toll on the resident gastrointestinal flora, such antagonisms may be a more general antidote-strategy for minimizing the adverse impact of drugs on human gut microbiota.

Second, antagonisms and synergies have clearly separable properties. While antagonisms strictly occur between drugs targeting different processes, synergies are more likely for drugs targeting the same processes. This distinction has clear mechanistic bases at the drug target level. Disrupting chemically or genetically a process at different steps is known to result in synergistic effects across organisms. Some of the most robust antibacterial monotherapies come from multi-target drugs inhibiting the same or directly linked processes. On the other hand, combining drugs that target distinct core processes may help the organism reaching a more stable equilibrium, as in the case of DNA and protein synthesis inhibitors. Consistently, genetic interactions are more commonly alleviating when genes are part of distinct functional processes in yeast.

Third, antagonisms are more prevalent than synergies, demonstrating that if random or empirical mixing of drugs has an effect, this will most likely be a reduction of individual drug efficacies. Even commonly used drug combinations in the clinic, such as linezolid with meropenem in sepsis patients, can have strongly antagonistic effects for some pathogens. Although antagonistic interactions pose efficacy and potentially toxicity issues in the clinic, their use can counter-select resistant isolates. On the other hand, synergies are more conserved than antagonisms across pathogenic species, which is encouraging for clinical use of combinations.

Finally, although antibacterials of the same class had similar interactions with other drugs, most antagonisms the inventors tested were due to modulation of intracellular drug concentrations. This suggests that drug-drug interactions are only partially driven by MoA and should not be automatically translated as direct functional interactions of their primary targets. This is likely the reason for the low conservation of drug-drug interactions across bacterial species, although their primary targets are highly conserved. Moreover, many antibiotic classes exhibited further subdivisions or members with outlier behaviors. This exposes the risk of drawing general conclusions for an entire class by studying one of its members. Similarly, the inventors did not observe exclusive synergy or antagonism between bactericidal drugs and oxidative stress, suggesting that the interrelation of these different classes of antibiotics and reactive oxygen species may be more complex than previously thought. The interactions the inventors report here are at the growth inhibition level. Although the inventors did not probe systematically, 16/16 drug-drug interactions were also detectable at a killing level. More systematic profiling will be required in the future to assess how drug-drug interaction outcomes relate at different levels (inhibition, killing, persister formation).

Beyond unraveling general principles, the inventor's work provides an unparalleled number of drug drug interactions in Gram-negative species. The inventors demonstrated the potency of several synergistic pairs against MDR clinical isolates in vitro, and for two of them in vivo, employing an established insect infection-model. Many more drug pairs are still to be uncovered within the inventor's dataset. Interestingly, human-targeted drugs were among the most frequent antibiotic adjuvants in the inventor's screen, and although the inventors included only four food additives, the inventors identified 64 synergies, one of which inhibited the growth of MDR E. coli isolates. In this particular case, vanillin synergized with spectinomycin, because it increased its intracellular concentration, via MdfA, a specific enterobacterial transporter. Thus, profiling more human-targeted drugs and food additives in future combinatorial screening will not only increase the possible solution space, but may also lead to efficient treatment strategies against MDR pathogens. Since many more human-targeted drugs inhibit bacterial growth than previously appreciated, such adjuvant strategies are particularly relevant.

In summary, the inventors have generated a comprehensive resource of pairwise drug combinations in Gram-negative bacteria, illuminating key principles of drug-drug interactions and providing a framework for assessing their conservation across organisms or individuals. Such information can serve as basis for equivalent screens in other microbes, studies investigating the underlying mechanism of pairwise drug combinations and computational predictions of their outcomes. Moreover, some of the general principles of drug-drug interactions may hold true beyond anti-infectives and microbes. For antibacterial drug therapies, the inventor's study highlights the promise that non-antibiotic drugs hold as adjuvants, and offers a new path for narrow spectrum therapies.

Methods

Strains, Strain Cultivation and Drugs

For each of the three Gram-negative species profiled in this study, the inventors used two broadly used and sequenced strains: Escherichia coli K-12 BW25113 and O8 IAI1, Salmonella enterica serovar typhimurium LT2 and 14028s, Pseudomonas aeruginosa PAO1 and PA14. To validate selected synergies, the inventors profiled 6 MDR clinical Enterobacteriaceae isolates recovered from human patient specimens: E. coli 124, 1027, 1334 and Klebsiella pneumoniae 718, 929 and 980.

All mutants used in this study were made using the E. coli Keio Knockout Collection—after PCR-confirming and retransducing the mutation to wildtype BW25113 with the P1 phage. The kanamycin resistance cassettes was excised when necessary using the plasmid pCP20. The plasmid used for mdfA overexpression was obtained from the mobile E. coli ORF library.

Drugs used in this invention were purchased from Sigma Aldrich, except for metformin hydrochloride (TCI Chemicals), clindamycin and bleomycin (Applichem), CHIR-090

(MedChemtronica) and vanillin (Roth). Stocks were prepared according to supplier recommendations (preferably dissolved in water) and kept in the dark at −30° C. until arrayed into the plates. For all drug combination experiments, drugs were diluted to the appropriate working concentrations in transparent 384-well plates (Greiner BioOne GmbH), with each well containing 30 µl total volume of Lysogeny Broth medium. After the addition of drugs, cells were inoculated at initial OD595 nm of 0.01 from an overnight culture. Same starting OD was used for all strains. All liquid handling (drug addition, cell mixing) was done with a Biomek FX liquid handler (Beckman Coulter). Plates were sealed with breathable 14 membranes (Breathe-Easy®) and incubated at 37° C. in a humidity-saturated incubator (Cytomat 2, Thermo Scientific) with continuous shaking, but without lids to avoid condensation. OD595 nm was measured every 40 min for 12 hours by a Filtermax F5 multimode plate reader (Molecular Devices).

Minimal Inhibitory Concentration (MIC) Calculation

The inventors defined MIC as the lowest concentration required to inhibit growth of a microorganism after 8 hours of incubation in Lysogeny Broth at 37° C. with shaking (384 well plates, starting OD595 nm 0.01). MICs to all drugs were computed using a logistic fit of growth (OD595 nm for 8 h) over 2-fold serial dilutions of the antibiotic concentrations for all strains used for the high throughput screening and follow-up experiments.

High-Throughput Screening of Pairwise Drug Interactions

For all drug combination experiments, drugs were diluted to the appropriate working concentrations in transparent 384-well plates (Greiner BioOne GmbH), with each well containing 30 µl total volume of LB. After the addition of drugs, cells were inoculated at initial OD595 nm~0.01 from an overnight culture. The same inoculum size was used for all strains. All liquid handling (drug addition, cell mixing) was done with a Biomek FX liquid handler (Beckman Coulter). Plates were sealed with breathable membranes (Breathe-Easy®) and incubated at 37° C. in a humidity-saturated incubator (Cytomat 2, Thermo Scientific) with continuous shaking, but without lids to avoid condensation. OD595 nm was measured every 40 min for 12 hours by a Filtermax F5 multimode plate reader (Molecular Devices). A flowchart of the experimental and analytical pipeline is shown in FIG. 6a. Data analysis was implemented with R and networks were created with Cytoscape.

Experimental Pipeline

The drug-drug interaction screen was performed using 4×4 checkerboards. 62 drugs were arrayed in 384 well plates with the different concentrations in duplicates (array drugs). Each plate contained 12 randomly distributed wells without arrayed drug: 9 wells containing only the query drug, and 3 wells without any drug. One query drug at a single concentration was added in all wells of the 384-well plate, except for the 3 control wells. All drugs were queried once per concentration, occasionally twice. The inventors used 78 drugs as query in E. coli and S. typhimurium, and 76 in P. aeruginosa. In total 79 query drugs were screened, out of which 75 were common for all three species. The 62 array drugs were a subset of the 79 query drugs. The same drug concentrations were used in both query and array drugs. Three drug concentrations (2-fold dilution series) were selected based on the MIC curves, tailored to the strain and drug. The highest drug concentration (close to MIC whenever possible), and the lowest fitness obtained per single drug.

For drugs that did not inhibit growth on their own, the inventors selected concentrations according to sensitivity of other strains/species or according to their use in clinics or for research. *E. coli* and *S. typhimurium* exhibited largely similar single drug dosage responses within species and therefore, the same drug concentrations were used for both strains of each species. In contrast, MICs often differed by several fold in *P. aeruginosa*, and thus drug concentrations were adjusted between the two strains.

The drug-drug interaction screen was performed using 4×4 checkerboards. 62 drugs were arrayed in 384 well plates with the different concentrations in duplicates (array drugs). Each plate contained 12 randomly distributed wells without arrayed drug: 9 wells containing only the query drug, and three wells without any drug. One query drug at a single concentration was added in all wells of the 384-well plate, except for the 3 control wells. All drugs were queried once per concentration, occasionally twice. The inventors used 78 drugs as query in *E. coli* and *S. typhimurium*, and 76 in *P. aeruginosa*. In total 79 query drugs were screened, out of which 75 were common for all three species. The 62 array drugs were a subset of the 79 query drugs. Same drug concentrations were used in both query and array drugs.

Growth Curves Smoothing and Analysis

The Gompertz model was fitted to all growth curves (when growth was observed) by using the R package grofit version 1.1.1-1 for noise reduction. Quality of fit was assessed by Pearson correlation (R), which was >0.95 for ~95% of all 505 growth curves. R<0.95 was indicative of either non-sigmoidal-shaped growth curves, typical of some drugs such as fosfomycin, or of highly noisy data. In the first case, the original data was kept for further analysis. In the second case, noisy data was removed. Plate effects were corrected by fitting a polynomial to the median of each row and column. Background signal from LB was removed by subtracting the median curve of the non-growing wells from the same plate. These were wells in which either the single or the double drug treatments fully inhibited growth; each plate contained at least three such wells. Data was processed per strain and per batch to correct for systematic effects.

Fitness Estimation

The inventors used a single time-point OD595 nm measurement (growth) for assessing fitness. This corresponded to the transition to stationary phase for cells grown without perturbation, as this allows the inventors to capture the effect of drugs on lag-phase, growth rate or maximum growth. Thus, the inventors used OD595 nm at 8 hours for *E. coli* BW25113 and both *P. aeruginosa* strains, at 7 hours for the fast-growers *E. coli* iAi1 and *S. typhimurium* 14028s, and at 9 hours for the slower growing *S. typhimurium* LT2.

According to the Bliss independence model and assuming that drug-drug interactions are rare, for most drug combinations the fitness of arrayed drugs (fa) equals the fitness in the presence of both drugs (faq) divided by the fitness of the query drug alone (fq):

$$\varepsilon = f_{aq} - f_a * f_q \qquad \text{(Eq. 1)}$$

$$\text{if } \varepsilon = 0$$

$$f_a = \frac{f_{aq}}{f_q} \Leftrightarrow f_a = \frac{g_{aq}/g_0}{g_q/g_0} \Leftrightarrow f_a = \frac{g_{aq}}{g_q} \qquad \text{(Eq. 2)}$$

where $\varepsilon$ denotes the Bliss score, f denotes fitness, g denotes growth, a denotes an arrayed drug, q denotes a query drug and 0 denotes no drug. The fitness in the presence of both drugs (faq) was calculated by dividing the growth in the presence of both drugs (gaq) by the median of the growth of drug-free wells from the same plate (g0). The fitness of the single query drugs (fq) was obtained by dividing the top 5% growing wells across each batch by the median of the growth of drug-free wells of each plate (g0). This metric is more robust to experimental errors than using only the 9 wells containing the query drug alone. Nevertheless, both estimators for fq yield very similar results (Pearson correlation=0.98). In line with Eq. 2, the fitness of arrayed drugs (fa) was estimated by the slope of the line of best fit between gaq and gq across all plates (query drugs) within a batch:

$$\begin{bmatrix} g_{q_1} \\ \vdots \\ g_{q_n} \end{bmatrix}_{n \times 1} \cdot f_{a_m} = \begin{bmatrix} g_{a_m} q_1 \\ \vdots \\ g_{a_m} q_n \end{bmatrix}_{n \times 1}, \ 1 \le m \le nr \text{ arrayed drugs} \qquad \text{(Eq. 3)}$$

for a given well across n query drugs q within a batch (FIG. 6*b*).

For wells containing drugs that had many interactions (Pearson correlation-r-between gaq and gq<0.7), the inventors restricted the query drug points (minimum 18) to improve the correlation and allow for fa estimation. Wells where r was still below 0.7, even after restricting the number of plates, were removed from further analysis due to high noise (~2%). For wells exhibiting no growth for >75% of the plates within a batch fa was deemed as zero.

Interaction Scores

Bliss Independence

Figure 7:
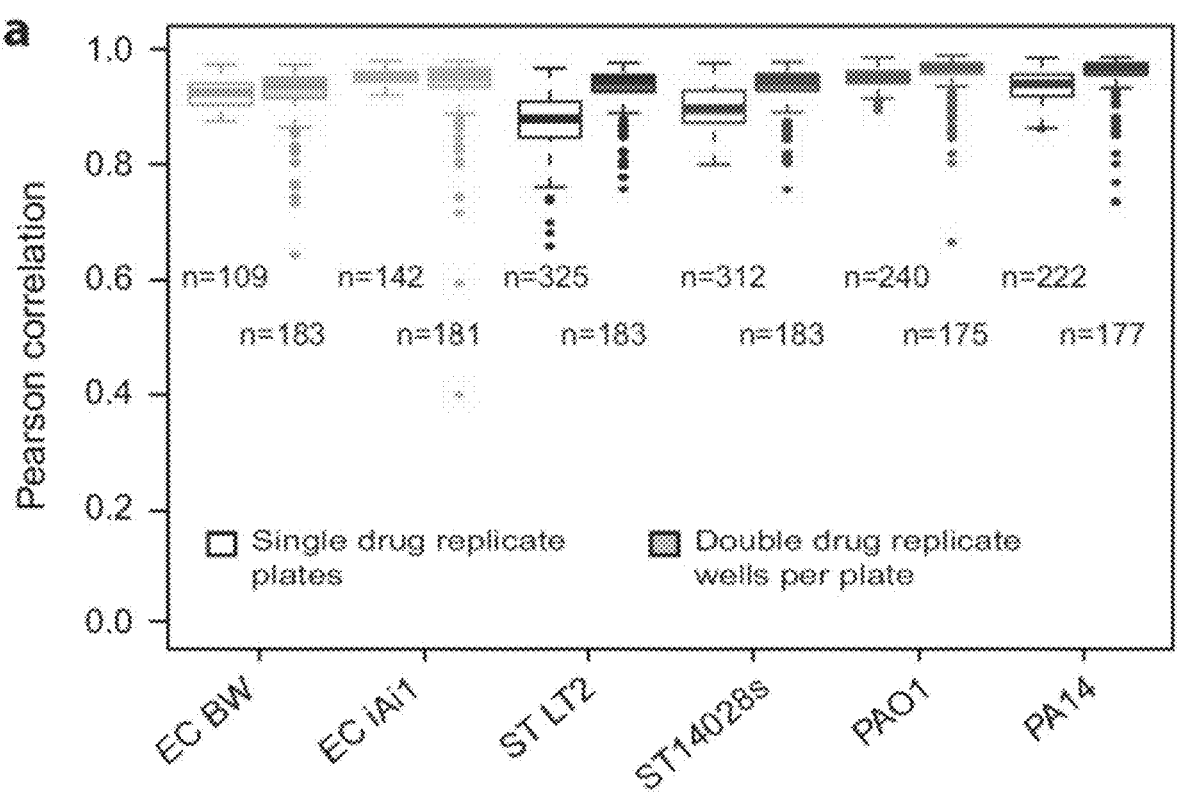
FIG. 7 shows data quality control. a) High replicate correlation for single and double drug treatments. Transparent boxplots contain Pearson correlation coefficients between plates of the same batch containing arrayed drugs only (LB was used instead of the second drug). n represents the total number of correlations. Full boxplots contain Pearson correlation coefficients between double drug replicate wells within the same plate, across all plates. n represents the number of wells used for correlation, $n_{max}$=(62 drugs+1 LB)×3 concentrations=189. Only wells with median growth above 20% were taken into account. b) Wells with lower median growth have lower replicate correlation. The double drug correlation coefficients used to generate the boxplot from a are plotted as function of the median growth of all wells across all plates for *E. coli* iAi1. Wells with overall lower growth (due to strong inhibition of arrayed drug) are less reproducible due to a combination of the lower spread of growth values and the sigmoidal nature of the drug dose response curves. c) Drug-drug interactions are rare. Density distributions of all Bliss scores (E) obtained per strain. d) The ability to detect synergies and antagonisms depends on the effects of single drug treatments. Bliss scores (ε) are plotted as function of expected fitness (fa*fq) for all drug concentration ratios for all combinations in *E. coli* BW (example). Boxplots summarizing both variables are shown besides the axes (n=101,322, the middle line corresponds to the median and the whiskers cover 1.5 times the IQR). Blind spots for detecting antagonism and synergy are indicated; they are both based on the expected fitness (see also FIGS. 8*c-d*) and thus dependent on the growth of the strain with the single drugs The number of drug combinations falling in the blind spot for antagonism is larger, due to the number of drugs used in the screen that do not inhibit *E. coli* on their own. e) Scatter plot of number of interactions per drug versus the minimum fitness of the drug alone (as obtained in screen). Strong and weak interactions are represented. n denotes the total number of interactions and R is the Pearson correlation coefficient. Strains are color coded as panels a & c. f) Density distributions of the number of interactions per drug for all strains.
Figure 7:
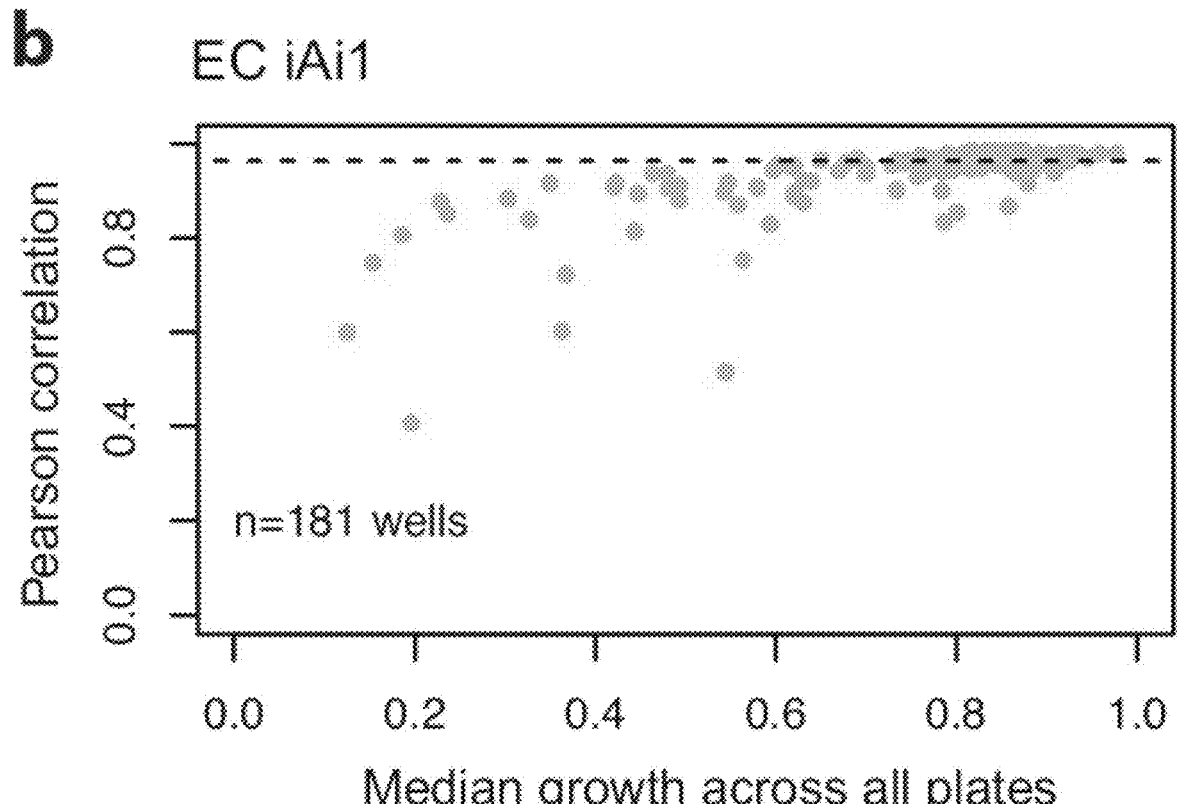
Figure 7:
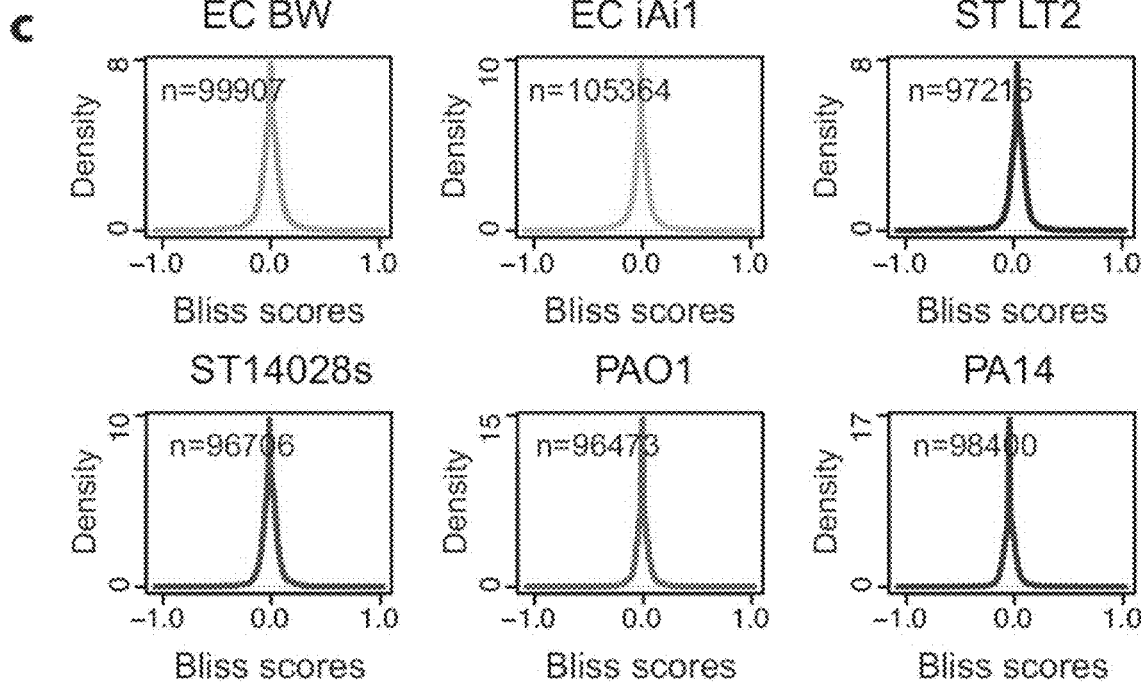
Figure 7:
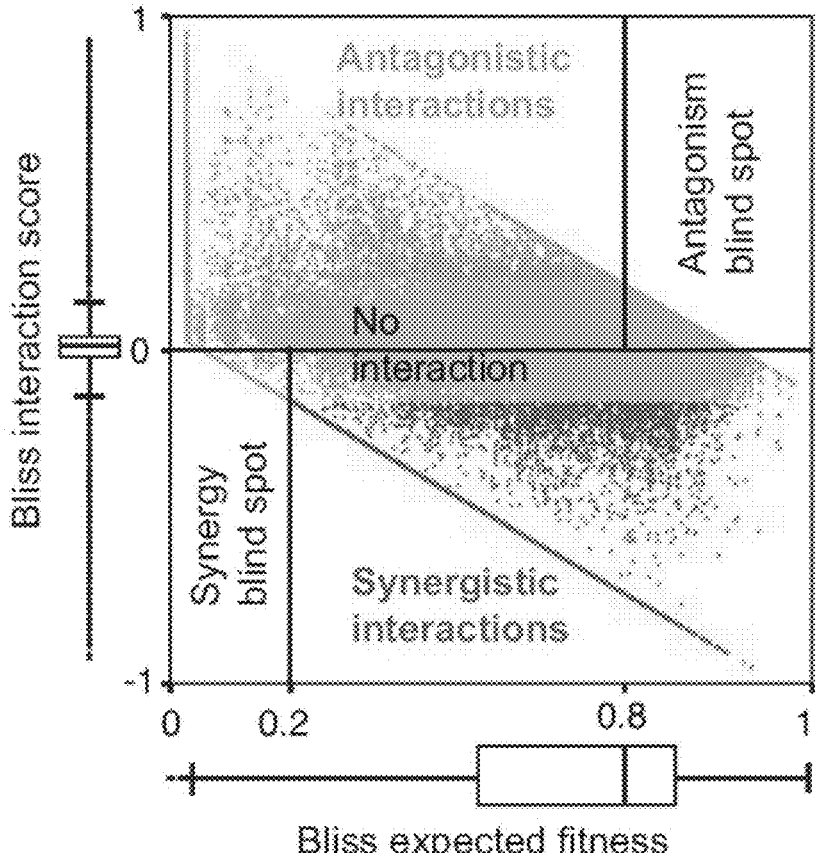
Figure 7:
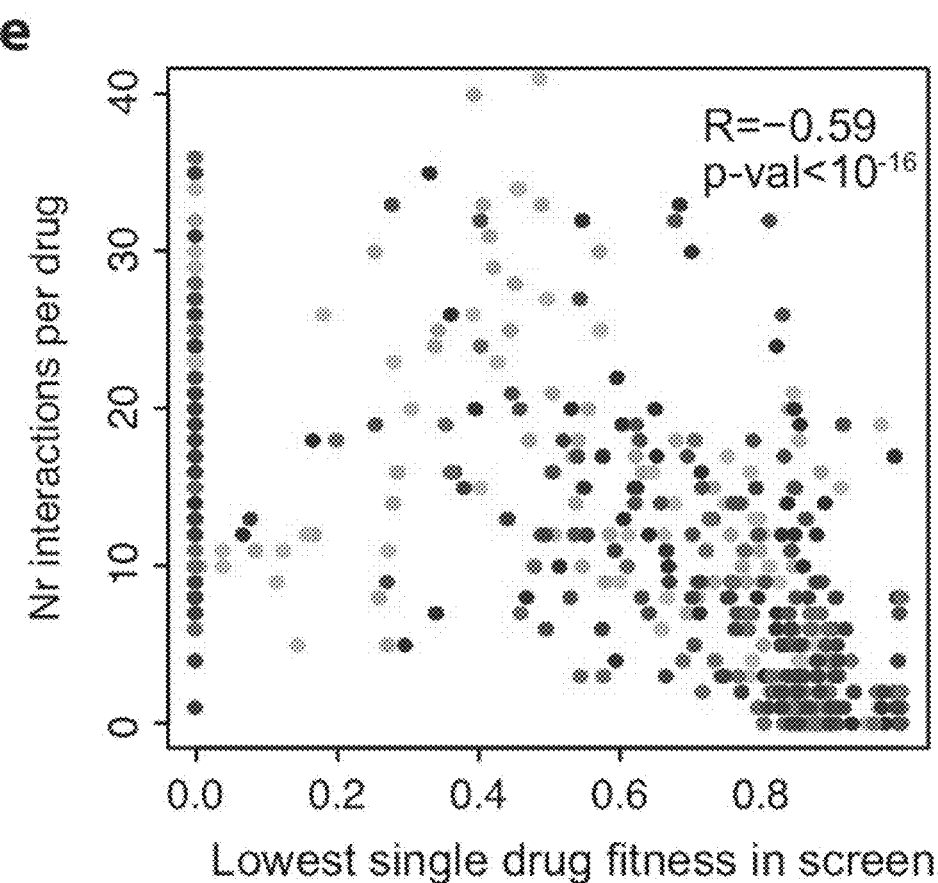
Figure 7:
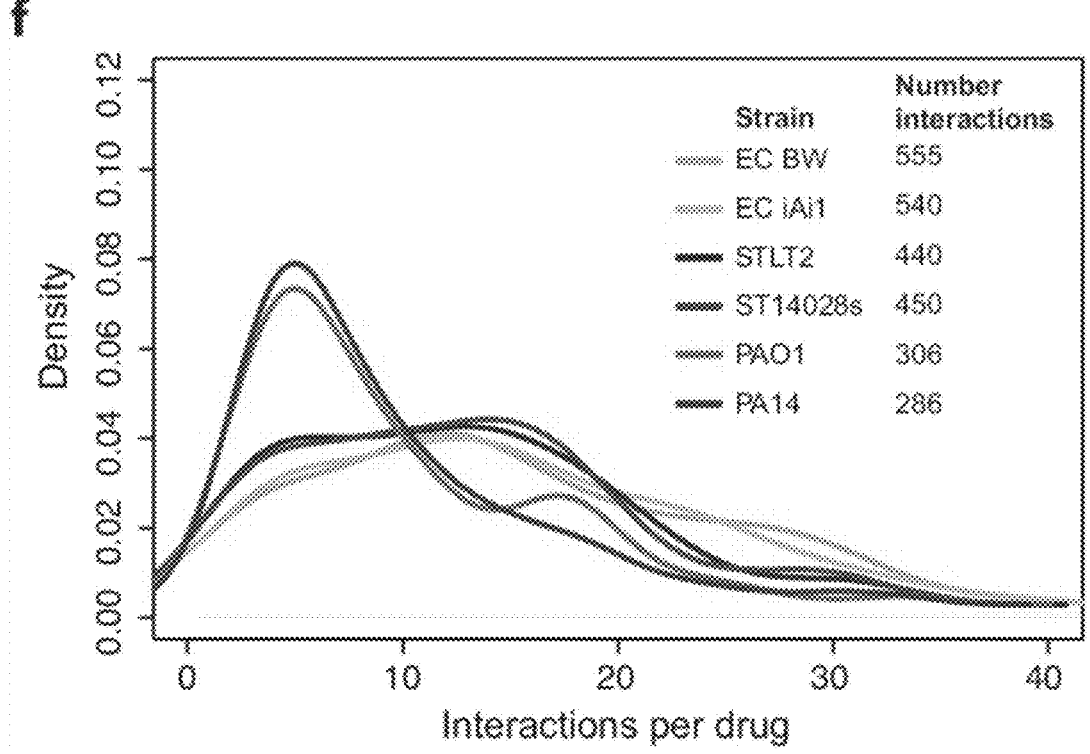
Figure 8:
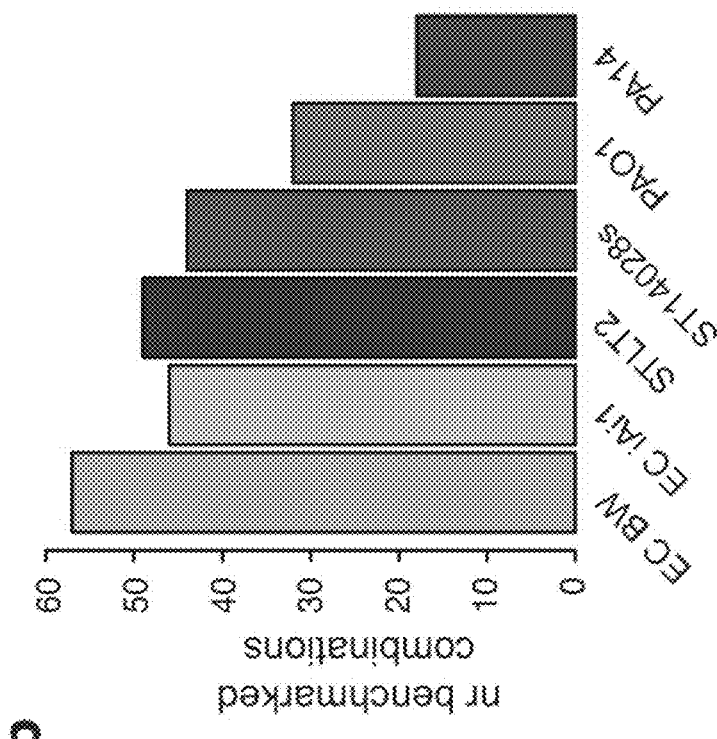
FIG. 8 shows benchmarking. a) Validation set is enriched in synergies and antagonisms to assess better true and false positives. Comparison of the interaction fractions between the screen and validation set. Both strong and weak interactions (FIG. 3*b*) are accounted for the screen tally. b) Number of benchmarked interactions per strain. c & d) Sensitivity analysis of the statistical thresholds for calling interactions. c) Total amount of interactions as function of the expected fitness (fa*fb) cutoff used for restricting the E distributions to relevant drug concentrations. Strong drug-drug interactions are classified according to the & distribution where they were significant: complete distribution only (i.e. all expected fitness wells), relevant wells only (i.e. all wells with fa*fb>cutoff for synergies and all wells with fa*fb<(1−cutoff) for antagonisms), or in both. Weak drug-drug interactions are independently assigned, and represented in white for completeness. The inventors selected an expected fitness cutoff of 0.2, as it resulted in the largest number of total interactions detected, with the highest precision and recall (91 and 74% respectively) after benchmarking against the validation dataset. d) Receiver operating characteristic (ROC) curve for the screen across different p-value thresholds (permutation test of Wilcoxon rank-sum) as a unique criterion for assigning interactions. The selected p-value (0.05) for screen threshold is indicated by a grey cross. Sensitivity to additional parameters for calling hits is shown: allowing interactions to be cither antagonisms or synergies but not both (1-sided); strong and weak interaction thresholds. True and false positive rates were estimated based on the validation dataset. Precision and recall for the final and best performing set of parameters, are shown: one-sided interactions, p<0.05, fa*fb cutoff=0.2 and |ε|>0.1 for strong interactions, |ε|>0.06 for weak interactions. TP, TN, FP and FN stand for True Positives, True Negatives, False Positives and False Negatives, respectively. n indicates the total number of benchmarked drug combination. e) Synergies between ß-lactams according to Loewe additivity interaction model. The results of 8×8 checkerboards for 3 combinations between ß-lactams in 4 strains are shown. The grey line in each plot represents null hypothesis in the Loewe additivity model, whereas the black line corresponds to the IC50 isobole, estimated by fitting a logistic curve to the interpolated drug concentrations (colored dots). Piperacillin did not reach 50% growth inhibition in *E. coli*, thus IC20 and IC40 isoboles were used for the amoxicillin+ piperacillin combination in *E. coli* BW and *E. coli* iAi1, respectively.
Figure 8:
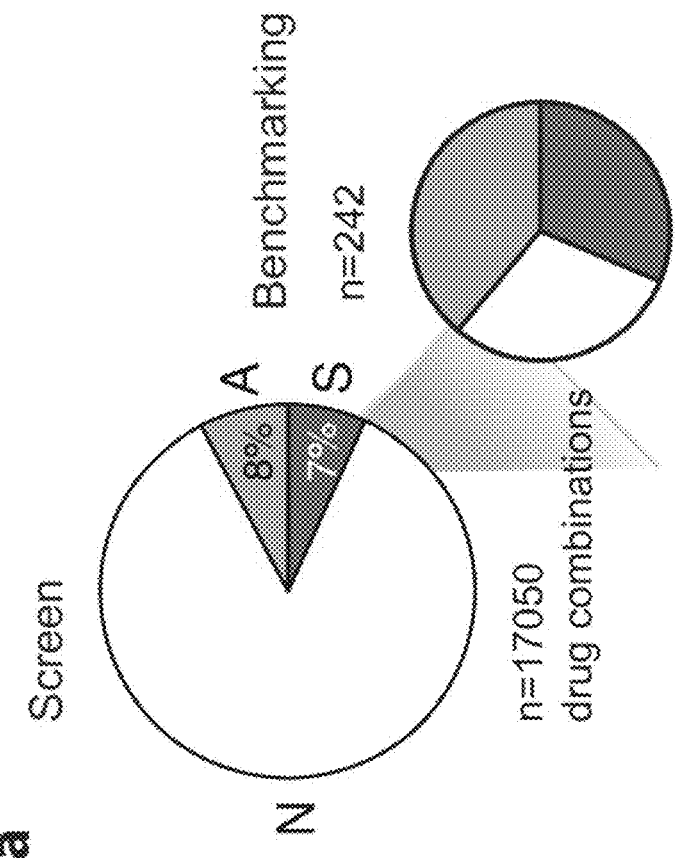
Figure 8:
Figure 8:
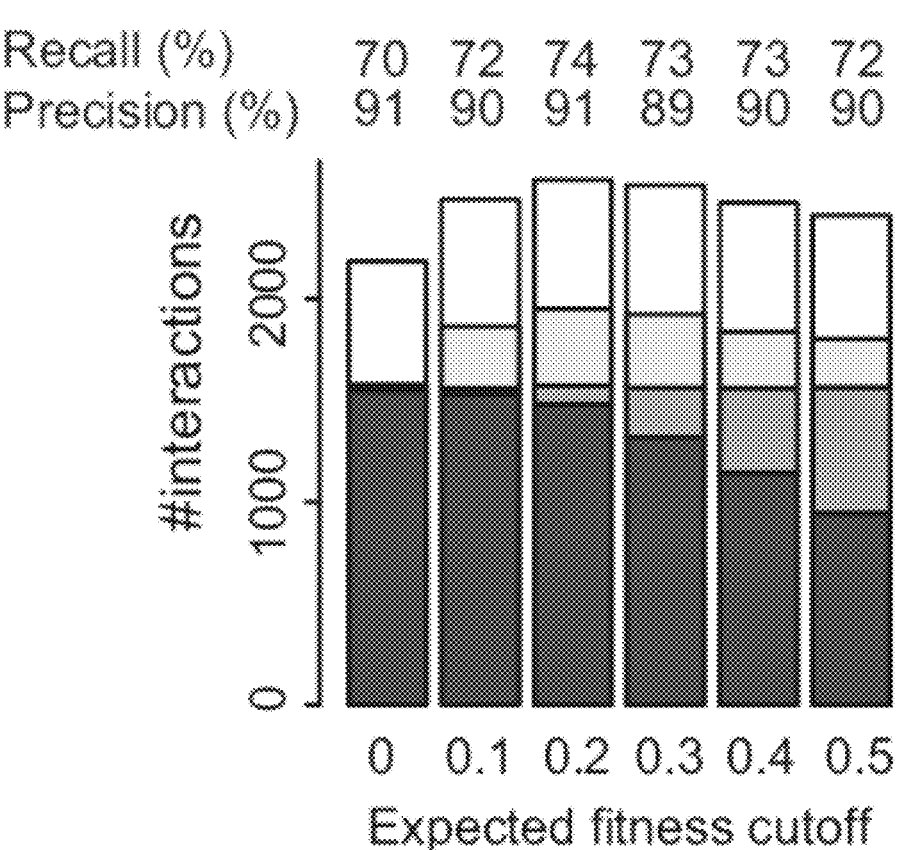
Figure 8:
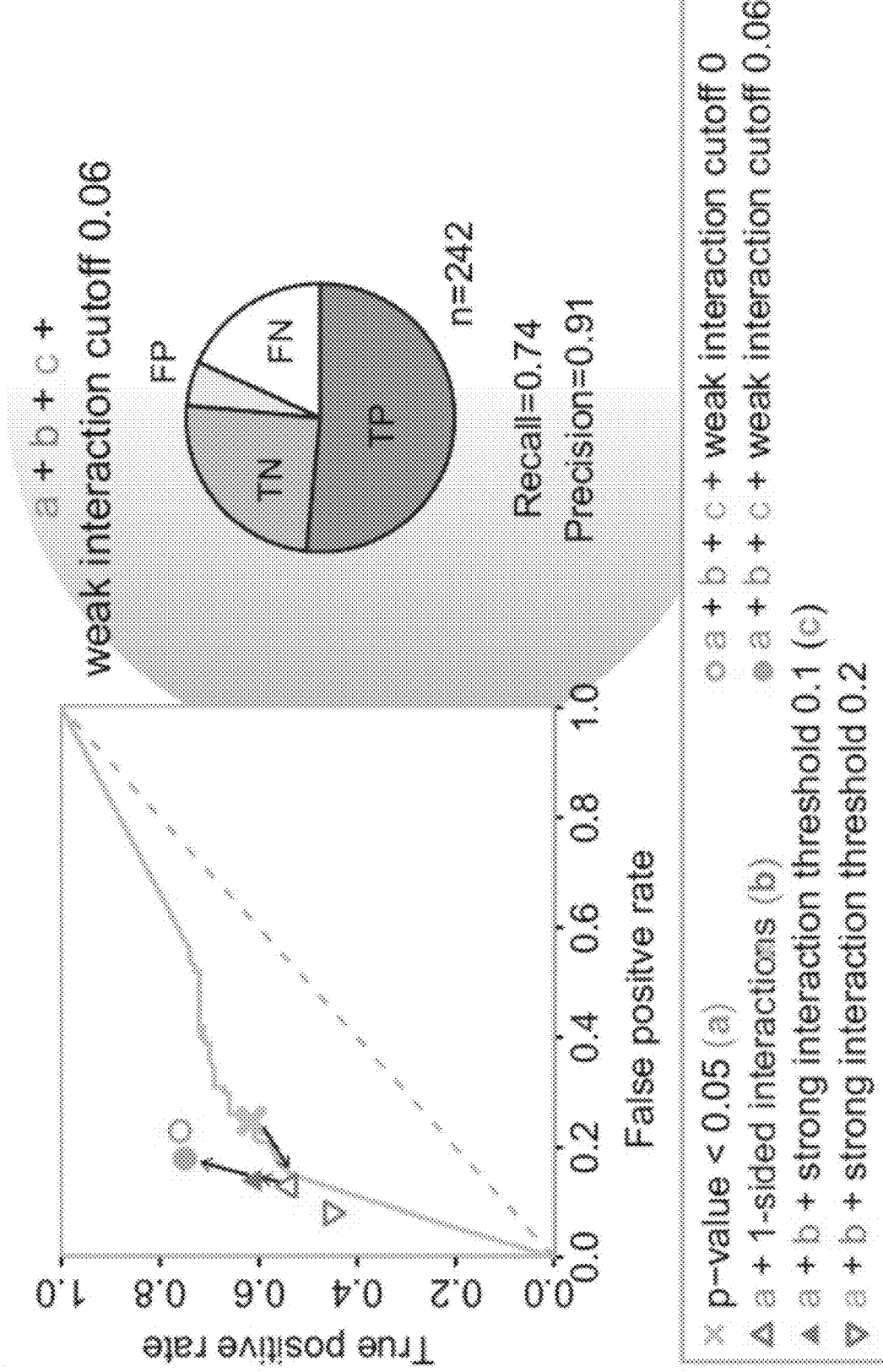
Figure 8:
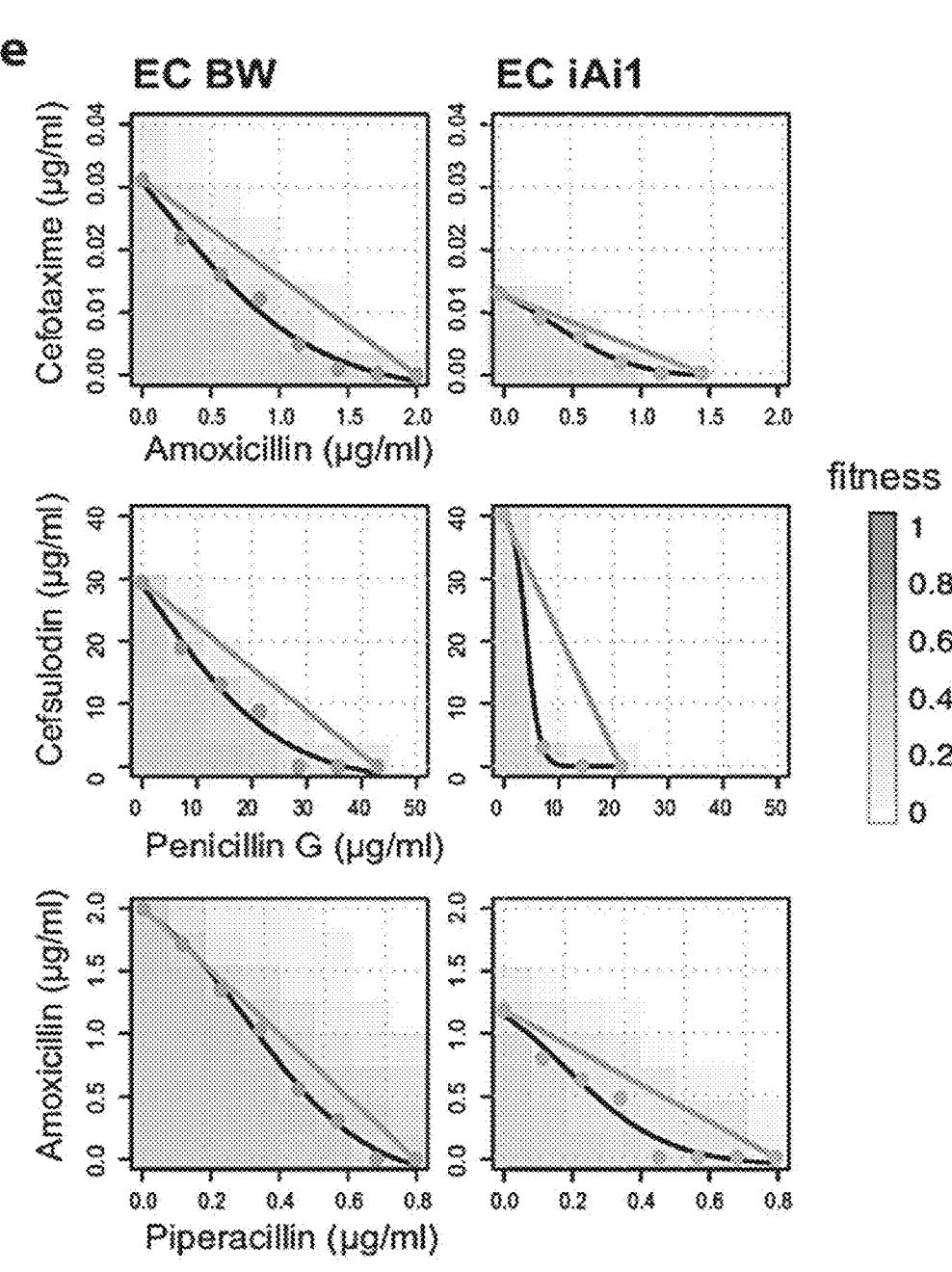
Figure 8:
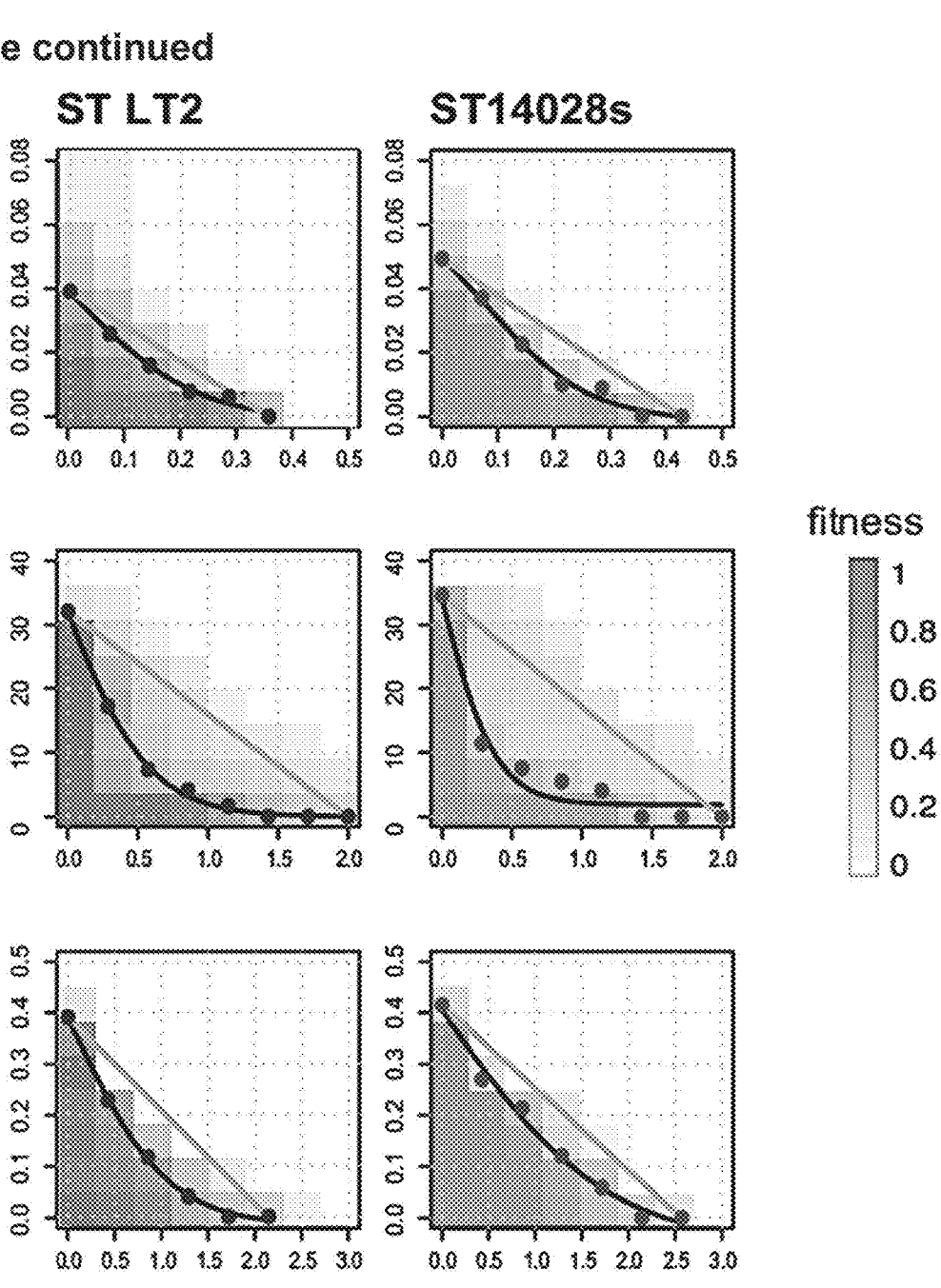

Bliss scores ($\varepsilon$) were calculated for each well as described above (Eq. 1). At least 3×3 drug concentrations×2 (duplicates)×2 (query and array drugs)=36, or 18 (only query drugs) scores were obtained per drug pair. Drug-drug interactions were inferred based on the Bliss independence model in three steps: a) strong interactions based on complete $\varepsilon$ distributions, b) strong interactions based on $\varepsilon$ distributions restricted to relevant drug concentrations and c) weak and conserved interactions within species. Cross-species comparison, drug-drug interaction networks and monochromaticity analysis shown in this study include all drug-drug interactions.

a) Strong Drug-Drug Interactions Based on Complete $\varepsilon$ Distributions 10,000 permutations of Wilcoxon rank-sum test (per drug pair, per strain) were performed. For every permutation, the $\varepsilon$ distribution of a given combination was compared to a $\varepsilon$ distribution of the same size randomly sampled from the complete $\varepsilon$ set for a given strain. Permutation p-values were calculated as follows:

$$p = \frac{\sum_{n=1}^{N} (p_n > 0.1) + 1}{N + 1} \qquad \text{(Eq. 4)}$$

where N is the total number of permutations (10,000) and pn is the p-value of the Wilcoxon rank-sum test obtained for the $n^{th}$ permutation. Strong drug-drug interactions were assigned to those drug pairs simultaneously satisfying two criteria: i) 1st or 3rd quartile of the $\varepsilon$ distribution below −0.1 or higher than 0.1, for synergies or antagonisms respectively, and ii) p<0.05 (after correcting for multiple testing, Benjamini-Hochberg). Only one-sided drug interactions were taken into account, thus those few interactions satisfying the criteria concurrently for synergy and antagonism were re-assigned as neutral (only n=1 for $\tilde{\varepsilon}>|0.1|$). The highest absolute ε value between 1st and 3rd quartile was used as single interaction score (ε̃) to reflect the strength of the drug-drug interactions.

b) Strong drug-drug interactions based on ε distributions restricted to relevant drug concentrations. Because drug interactions are concentration dependent, the same statistical procedure was repeated after restricting the drug concentration ratios to those relevant for either synergy or antagonism. This constraint was added by excluding ε values corresponding to concentration ratios where the expected fitness (product of the fitness on single drugs, fa*fb) was below 0.2 for synergy and above 0.8 for antagonism—blind spots for both interactions (FIG. 7D). These interactions are described by their p-value and ε obtained with restricted drug concentration ratios. Although most interactions were detected based on both full and restricted ε distributions, each of the different methods had uniquely identified interactions (FIG. 8C). With the expected fitness cutoff of 0.2, the inventors identified the highest number of strong interactions (1950) with 90 uniquely identified interactions from full ε distributions and 379 from restricted (see also sensitivity analysis).

Moreover, restricting ε values based on expected fitness also allows defining whether synergy or antagonism is detectable for any given drug pair. No significant p-value was found for drug pairs with less than 5 ε scores within the relevant expected fitness space, as their sample size is insufficient. Synergy and antagonism could not be detected for 1% and 25% of all interactions, respectively.

c) Weak and Conserved Drug-Drug Interactions within Species

For drug pairs with a strong drug-drug interaction in only one of the two strains per species, the criteria for assigning interactions for the second strain was relaxed to $|\tilde{\varepsilon}_{second\ strain}|>0.06$, provided that the interaction sign was the same. Interactions assigned with this approach are termed weak and conserved.

Loewe Additivity

For combinations between ß-lactams for which high-resolution 8×8 checkerboards with sufficient growth inhibition was available in the validation dataset, Loewe additivity was used to confirm the interactions. Drug-drug interactions were inferred by the shape of the isoboles (lines of equal growth) in two-dimensional drug concentration plots. Unless stated otherwise, all isoboles correspond to 50% growth inhibition (IC50) and were obtained by fitting a logistic model—with lines representing isoboles and dots IC50 interpolated concentrations. To interpolate IC50 concentrations (or other ICn %), a logistic model was used to fit the growth for each concentration of the first drug across different concentrations of the second drug. The null-hypothesis of this model is represented by the additivity line: a linear isobole connecting equal individual IC's by the two drugs.

Sensitivity Analysis

The inventors confirmed the adequacy of the main statistical parameters used to assign interactions by conducting a sensitivity analysis. Several expected fitness (fa*fb) cutoffs were tested, while keeping the other parameters constant (FIG. 8c). The added value of restricting the ε distributions to relevant drug concentrations (based on expected fitness) was strongly supported by the proportion of strong drug-drug interactions found exclusively using this criterion (~19% with the inventor's selected cutoff). The selected cutoff (0.2; disregarding wells with fa*fb<0.2 for synergies and with fa*fb>0.8 for antagonisms) resulted in the largest number of total interactions assigned, and the highest precision (91%) and recall (74%) after benchmarking against the validation dataset (FIG. 8c).

Figure 3:
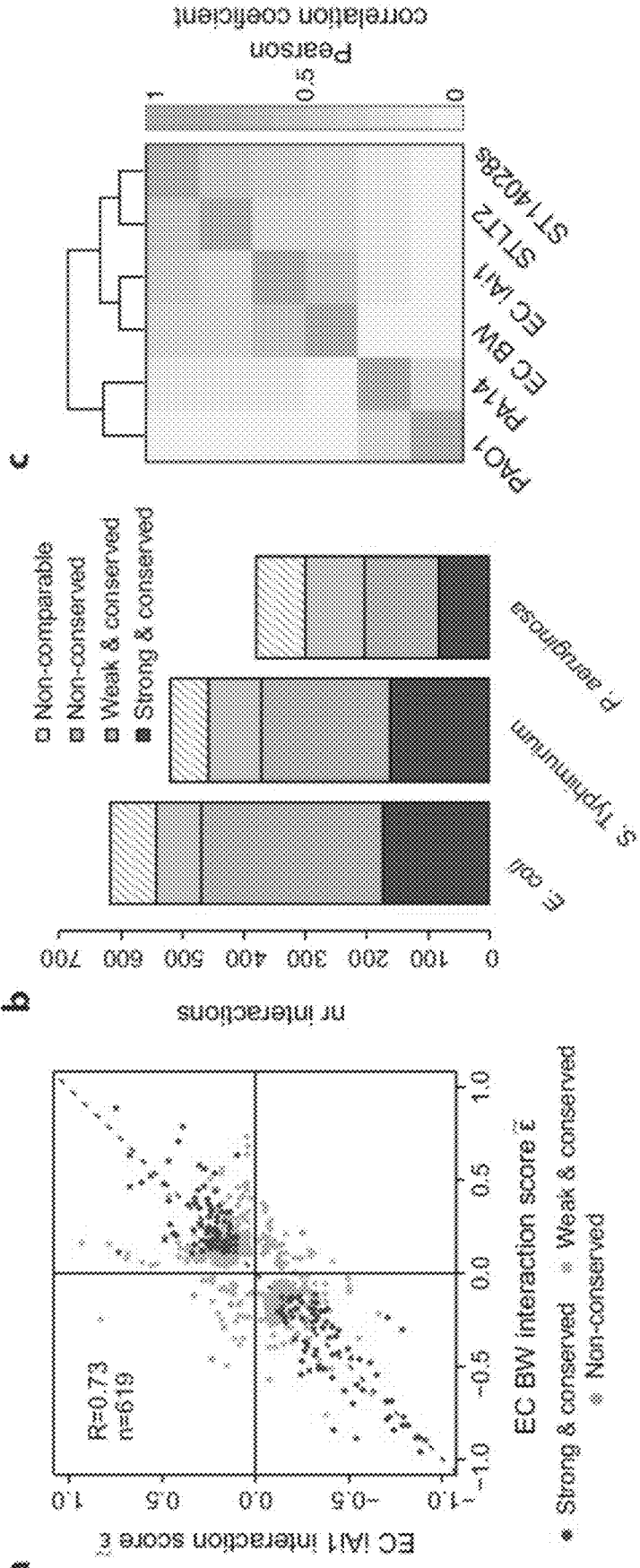
FIG. 3 shows the conservation of drug-drug interactions across strains and species. a) Drug-drug interactions are conserved in *E. coli*. Scatter plot of interaction scores from the two *E. coli* strains; significant interactions for at least one of the strains are shown. Dark blue: strong and conserved interactions in both strains; light blue: strong interactions in one strain and concordant behavior in other (weak and conserved); grey: interactions occurring exclusively in one strain or conflicting between strains (non-conserved). R denotes the Pearson correlation and n the total number interactions plotted. b) Drug-drug interactions are highly conserved within all three species. Significant interactions observed for at least one strain per species are presented. Colors as in a; non-comparable refers to combinations that have significantly different single drug dose responses between strains. c) Drug interaction profiles are phylogenetically driven. Clustering of strains based on Pearson correlation of their drug interaction profiles (taking into account all pairwise drug combinations). Strains of the same species cluster together, with the two enterobacterial species, *E. coli* and *S. typhimurium*, behaving more similar to each other than to the phylogenetically more distant *P. aeruginosa*. d) Drug-drug interactions are largely species-specific. The Venn diagram shows the overlap of interactions between the three species; n=total number of interactions; $n_c$=conflicting interactions between species (synergy in one species, antagonism in the other), not accounted for in the Venn diagram. e) Conserved drug-drug interaction network. Nodes represent individual drugs grouped and colored by targeted cellular process (as in FIG. 2*d*). Drug names are represented by 3 letter codes. Dashed and full edges correspond to conserved interactions between two or three species, respectively. f) Synergies are more conserved than antagonisms. Mosaic plots show the quantification of synergy and antagonism among conserved and non-conserved interactions between species. Chi-squared test p-values are shown.
Figure 3:
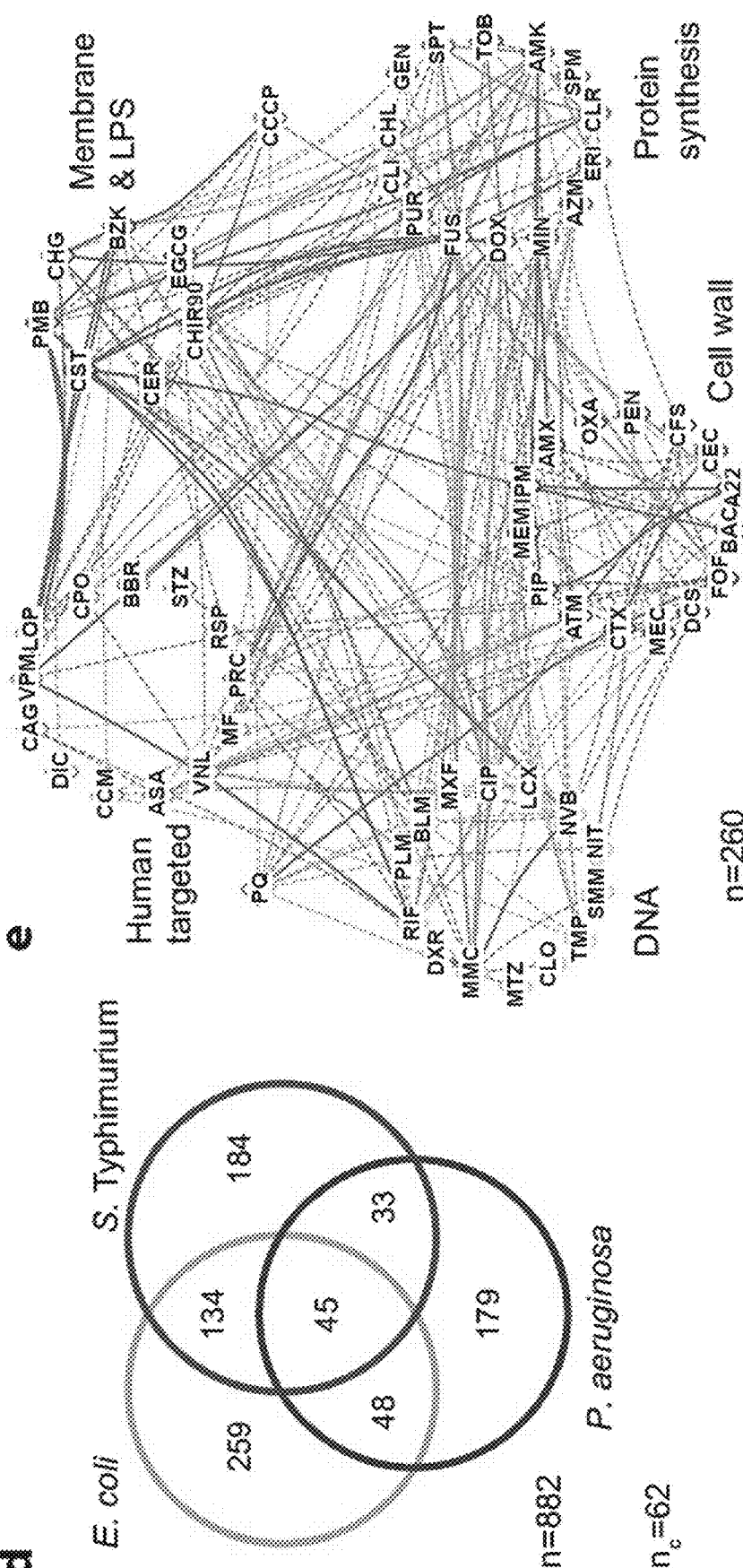
Figure 3:
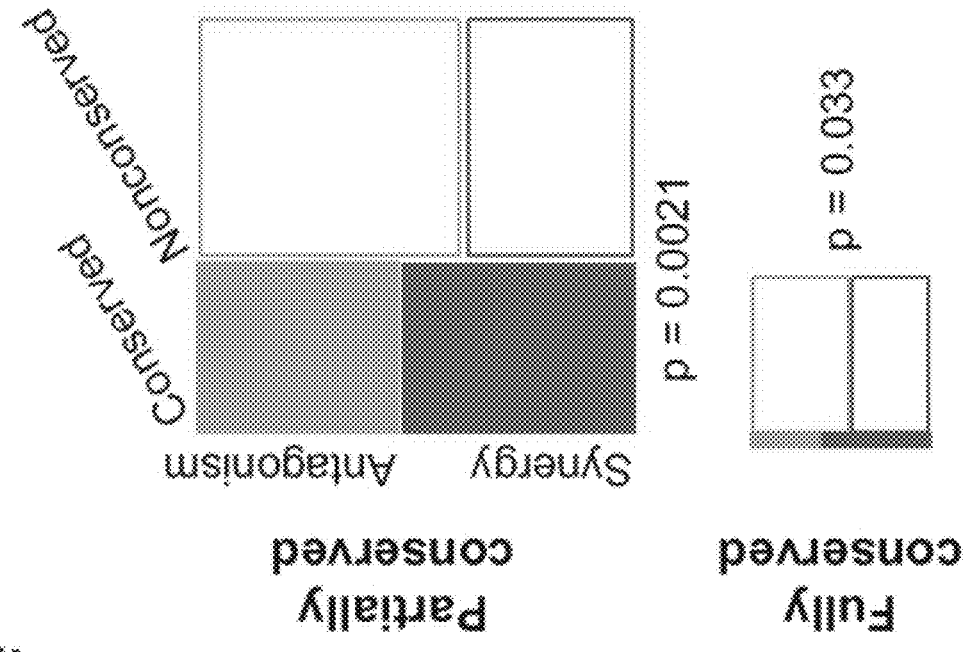
Figure 13:
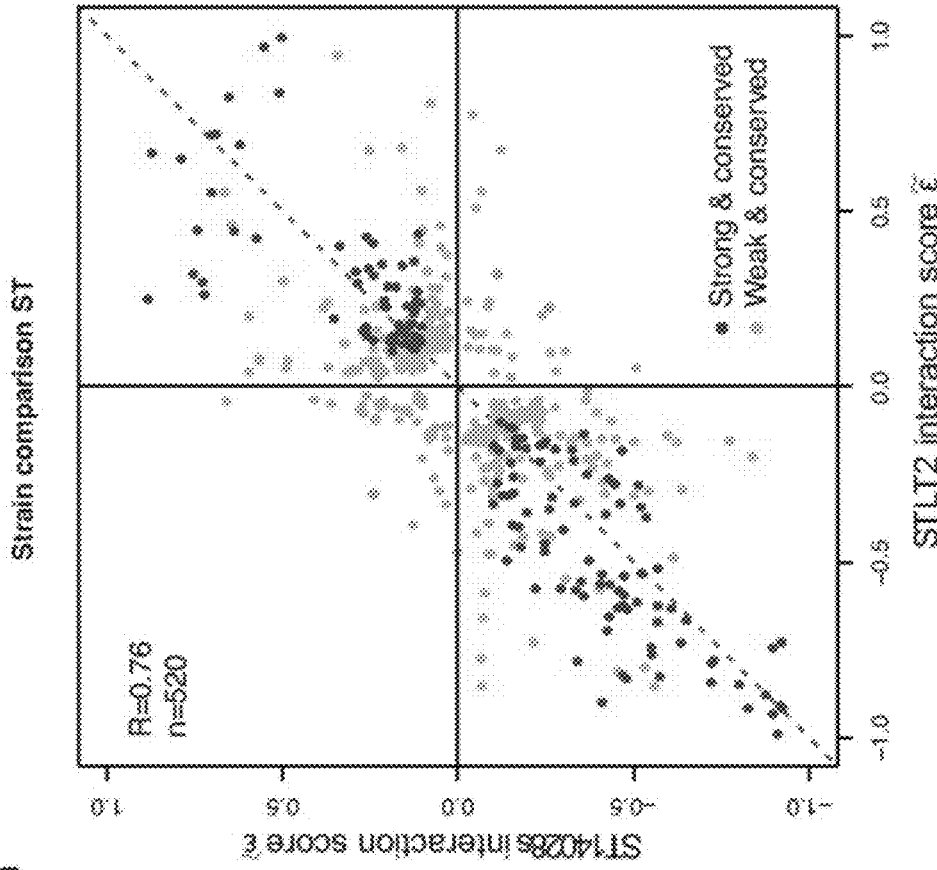
FIG. 13 shows that drug-drug interactions are largely conserved within species and only partially MoA-driven. a & b) Drug-drug interactions are conserved in S. typhimu-rium (a) and P. aeruginosa (b). Scatter plot of interaction scores in the two strains of each species; only significant interactions for at least one strain are shown. Colors and grouping as in FIG. 3a. R denotes the Pearson correlation and n the total number interactions plotted. Lower correla-tion in P. aeruginosa is presumably due to fewer and weaker interactions in total. c) Monochromaticity between all drug categories. The monochromaticity index (MI) reflects whether interactions between drugs of two categories are more synergistic (MI=−1) or antagonistic (MI=1) than the background proportion of synergy and antagonism. MI was calculated using all interactions from the 6 strains for all category pairs that had at least 2 interactions. White cells in the heat map correspond to category pairs for which no (or insufficient number of interactions were observed. d) Human-targeted drugs, and LPS or PMF inhibitors are strong and promiscuous adjuvants. Density distributions of the MIs per drug category from panel c are shown. n denotes the amount of drugs in category involved in i interactions.
Figure 13:
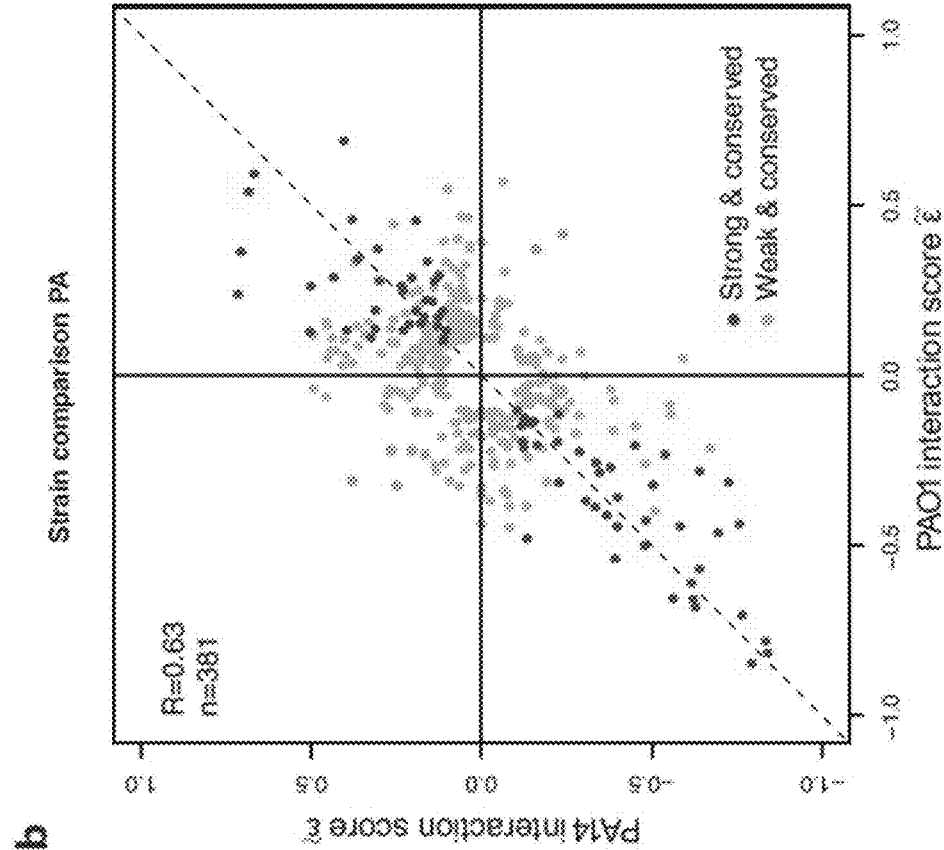
Figure 13:
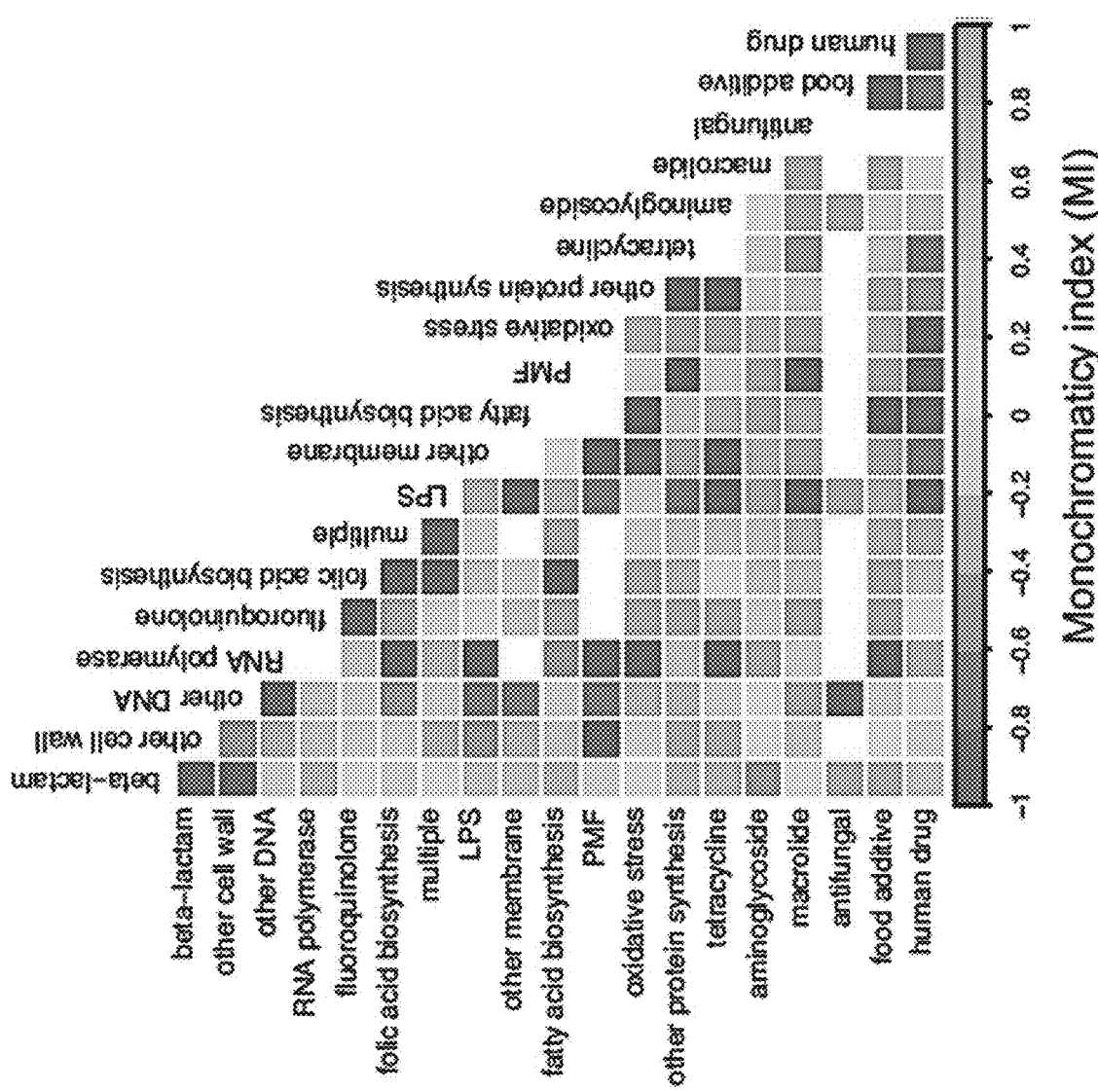
Figure 13:
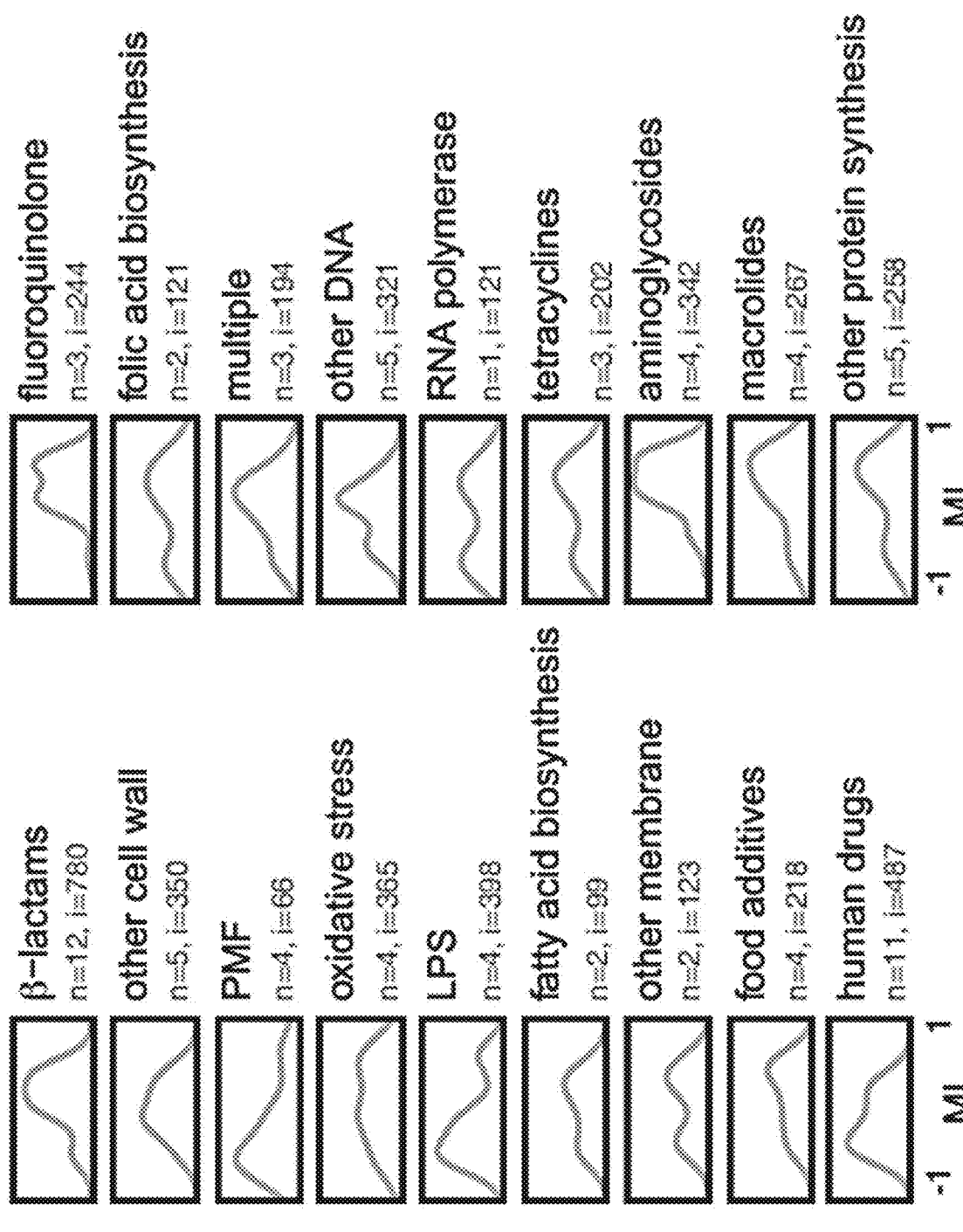

The suitability of the thresholds applied to define strong ($|\tilde{\varepsilon}|>0.1$) and weak ($|\tilde{\varepsilon}|>0.06$) interactions was assessed by their impact on the true and false positive rates (TPR and FPR respectively, FIG. 8d). A threshold of $|\tilde{\varepsilon}|>0.1$ is beneficial, as it imposes a minimum strength to assign interactions. 0.1 corresponds to ~3 times the median of the 1st and 3rd quartiles across all ε distributions (FIG. 6c). Lowering this threshold results in lower TPR, because several drug pairs are reassigned to neutral due to ambiguity in calling interaction. Increasing this threshold lowers the TPR, because only very strong interactions will be assigned (FIG. 8d). Drug-drug interactions are highly conserved within species, exhibiting high correlation of ε̃ observed for all species (FIG. 3a and FIG. 13a-b). This motivated the inventors to relax the interaction strength threshold for the second strain if interaction score |ε̃| was above 0.1 in first, dubbing these interactions weak and conserved. Including weak and conserved interactions in the inventor's analysis increased the TPR by 15%. Adding a threshold for weak interactions of $|\tilde{\varepsilon}|>0.06$ (~2 times the median of the 1st and 3rd quartiles of all ε distributions) is key for maintaining a suitable FPR (FIG. 8d).

Benchmarking and Clinical Isolates Checkerboard Assays

Figure 5:
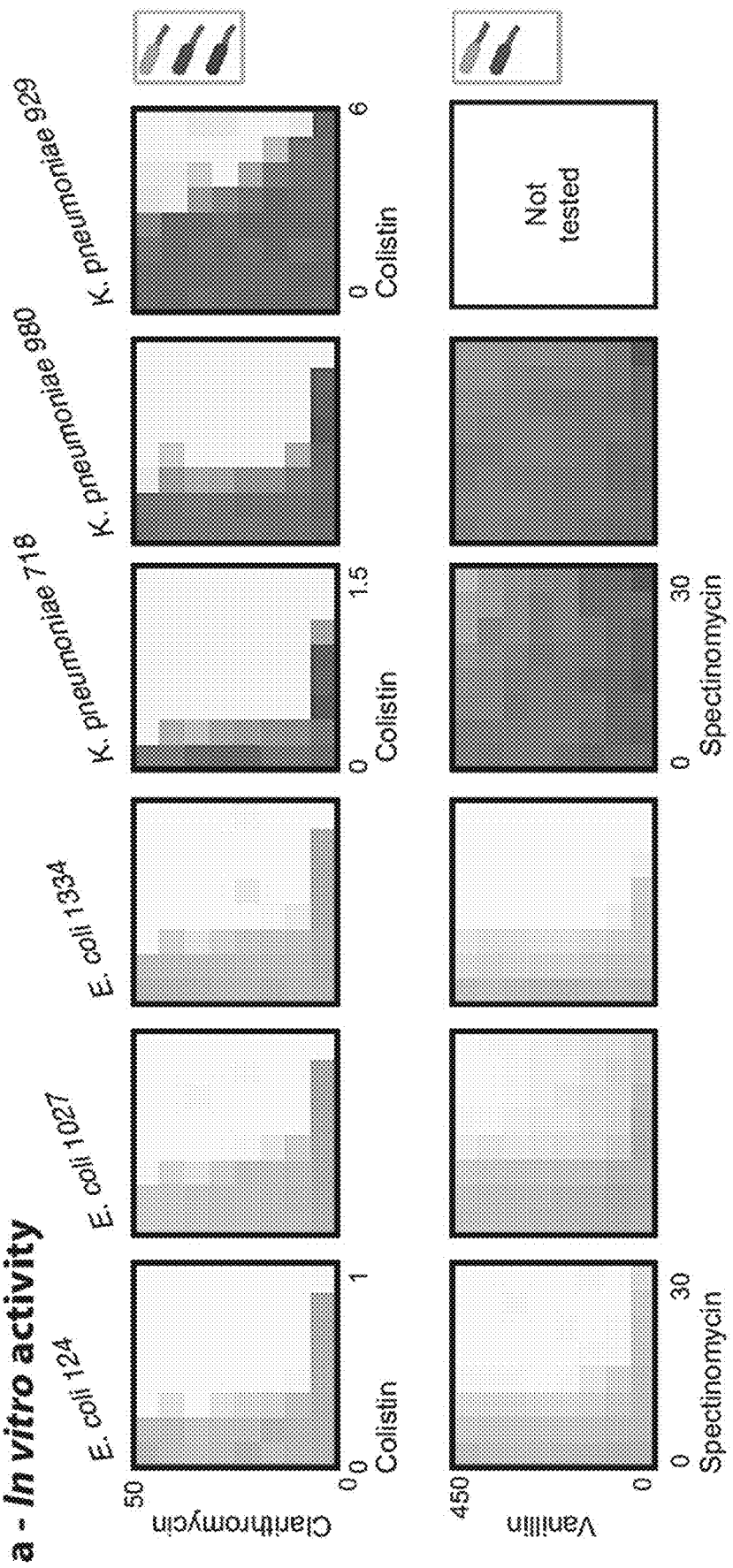
FIG. 5 shows potent synergistic combinations against Gram-negative MDR clinical isolates. a) In vitro synergies, shown as 8×8 checkerboards. The vanillin-spectinomycin combination acts synergistically only against MDR *E. coli* strains. Drug pairs are the same per line and indicated at the first checkerboard. The species in which interaction was detected in screen are indicated after the last checkerboard. Concentrations increase on equal steps per drug (see key); only minimal and maximal concentrations are shown in µg/ml for first strain of each species. Except for colistin, the same concentration ranges were used. As indicated, higher colistin concentration was used for the colistin-resistant *K. pneumoniae* 929. One of two biological replicates is shown. b) Drug synergies against the same MDR strains in the *Galleria mellonela* infection model. Larvae were infected by *E. coli* and *K. pneumoniae* MDR isolates (106 and 104 CFU, respectively) and left untreated, or treated with single drugs or combination. % larvae survival was monitored at indicated intervals after infection, n=10 larvae per treatment. Shown is the average of 3-4 biological replicates; error bars depict standard deviation.
Figure 5:
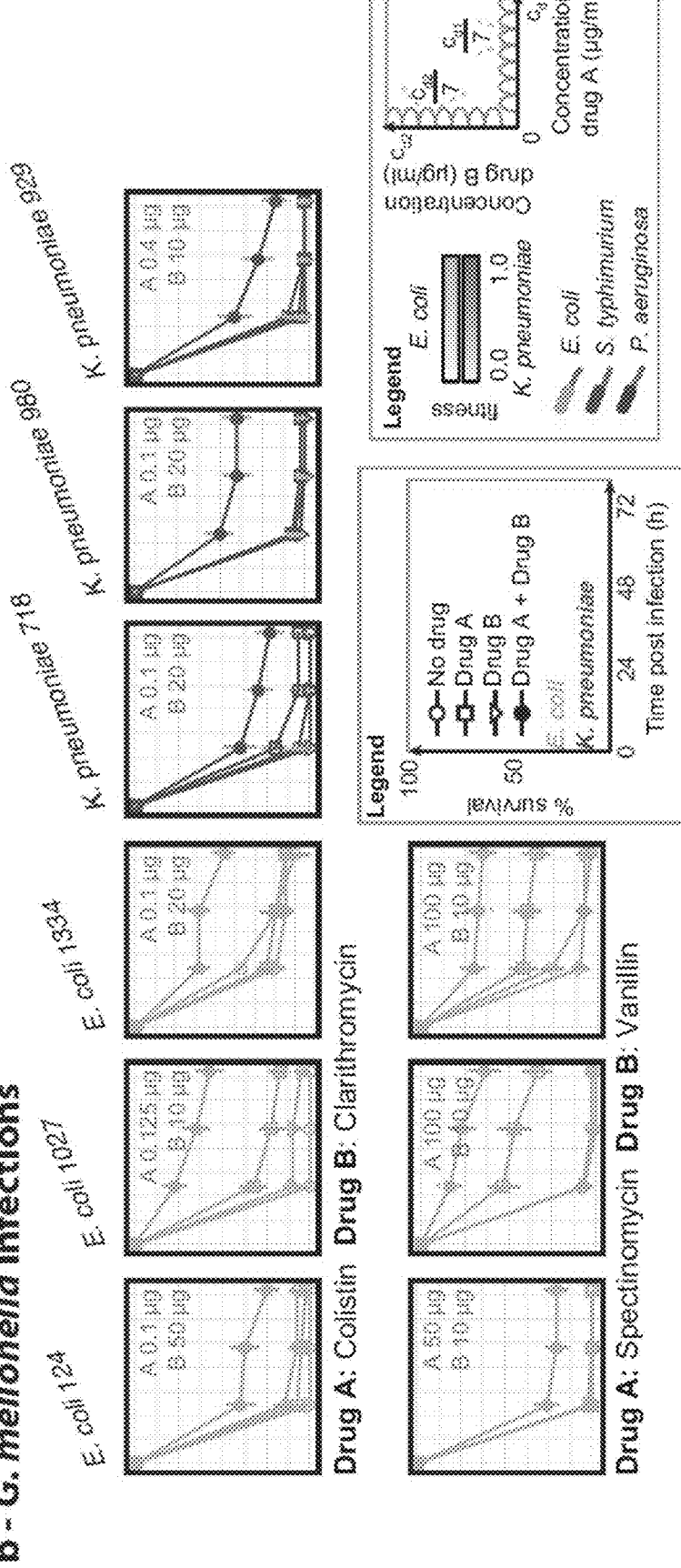

8×8 checkerboard assays were performed for post-screen validation experiments, as well as to test selected synergies against the MDR clinical isolates (FIG. 5). As in the screen, growth was assessed based on OD595 nm at early stationary phase for the no drug controls. The time-points used in the screen were used again here for screen strains, whereas 8 hours were used for all E. coli and K. pneumoniae MDR isolates. Fitness was calculated by dividing OD595 nm after single or double drug treatment by no drug treatment for each individual checkerboard. Bliss scores (ε) were calculated for all concentration ratios tested per drug combination, resulting in 49 ε values per drug pair. Drug combinations were analyzed based on ε distributions, after removing wells in which one of the drugs alone and its subsequent combinations with the second drug completely inhibited growth. Antagonism was called when the median of the ε distribution was above 0.1 or the Q3 was above 0.15. All experiments were done in biological duplicates, and interactions were considered effective when duplicates agreed.

Similarly, synergies were called when the median of the ε distribution was below –0.1 or the Q1 was below –0.15. Finally, all interactions were manually inspected and 10 drug pairs for which interactions only occurred in a small concentration window, but still resulted in median and quartiles just below the cutoffs were recovered and assigned the appropriate drug interaction.

Assessing Conservation of Drug-Drug Interactions

Conservation of drug-drug interactions between strains of the same species was assessed by Pearson correlation of the interactions scores ε. For potentially non-conserved drug-drug interactions, the expected fitness distributions of the two strains were taken into account. When the two distributions were significantly different according to a Wilcoxon rank-sum test (p-value <0.05 after BH correction for multiple testing), the drug pairs were deemed as non-comparable between the two strains.

To assess the cross-species conservation of drug-drug interactions, the inventors took into account only drug pairs that were probed in all three species. Drug-drug interactions were defined as being detected within a species, when detected in at least one of the two strains and no change of interaction sign was observed for the other strain. Interactions were then compared across the three species. Cases in which an interaction between drugs changed sign across species (conflicting interactions; ~7% of all interactions) were excluded from the comparative "across-species" Venn diagram (FIG. 3D). Note that with current analysis a given drug-drug interaction may be conserved across species, but not conserved within the species.

Conservation at the single drug level was defined based on shared resistance and sensitivity. A strain was considered sensitive to a given drug if one of the drug concentrations inhibited growth for at least 30%. In line with conservation of drug-drug interactions across species, single drug responses are conserved across species when at least one strain of both species has the same sign (sensitive or resistant).

Monochromaticity Index

The monochromaticity index (MI) between drug pairs was defined according to Szappanos et. al:

$$\text{if } r_{ij} > b, MI_{ij} = \frac{(r_{ij} - b)}{1 - b} \qquad \text{(Eq. 5)}$$
$$\text{fir}_{ij} = b, MI_{ij} = 0$$
$$\text{if } r_{ij} < b, MI_{ij} = \frac{(r_{ij} - b)}{b}$$

where rij denotes the ratio of antagonism to all interactions between drugs from classes i and j, and b denotes the ratio of antagonism to all interactions. The inventors set a minimum of 2 interactions between drugs from classes i and j in order to calculate the MI. MI equals 1 if only antagonisms occur between drugs from classes i and j, and −1 if only synergies occur. MI equals zero if the fraction of antagonism reflects the background ratio b. Both strong and weak drug interactions were taken into account across all species, in order to obtain one MI index per drug category pair.

Assessment of Drug Combinations in the *Galleria mellonella* Infection Model

Larvae of the greater wax moth (*Galleria mellonella*) at their final instar larval stage were used as an in vivo model to assess efficacy of drug combinations. Larvae were purchased from UK Waxworms (Sheffield, UK) and TZ-Terraristik (Cloppenburg, Germany). Stock solutions of vanillin (in 20% DMSO), spectinomycin (Aqua dest.), colistin (Aqua dest.) and clarithromycin (20% DMSO/0.01% glacial acetic acid) were freshly prepared and diluted in PBS to the required concentration. Drugs and bacterial suspensions were administered by injection of 10 μL aliquots into the hemocoel via the last left (drugs) and right (antibiotic) proleg using Hamilton precision syringes. Controls included both uninfected larvae, and larvae which were injected into both last prolegs with the solvent used for the drugs. Drug toxicity was pre-evaluated by injection of serial dilutions of either single drugs or drug combination, and drugs were used at amounts that caused little/no toxicity. Similarly, time kill curves were generated by inoculating the larvae with 10 μl of serial diluted bacterial suspensions (1×102 to 1×107 colony forming units [CFU]) to identify an optimal inoculum. For final experiments, groups of ten larvae were injected per strain/drug combination and placed into Petri dishes and incubated at 37° C. Larvae were infected with a (sub)lethal dose of 106 and 104 CFU for *E. coli* and *K. pneumoniae* isolates, respectively, and subsequently injected with the drugs, 1-hour post infection. Larvae survival was monitored at the indicated time points by two observers independently. Each strain/drug combination was evaluated in 3-4 independent experiments.

Cell Viability Assays and Intracellular Antibiotic Concentration

Ciprofloxacin

Overnight cultures of *E. coli* BW25113 were diluted 1:1,000 into 50 ml LB and grown at 37° ° C. to OD595 nm~0.5. Paraquat (50 μg/ml), Vanillin (150 μg/ml), Benzalkonium (5 μg/ml), Caffeine (200 μg/ml), Doxycycline (0.5 μg/ml), Rifampicin (5 μg/ml), Trimethoprim (5 μg/ml) or Curcumin (100 μg/ml), were added to the cultures and incubated at 37° C. for 30 minutes prior to the addition of 2.5 μg/ml final concentration ciprofloxacin. The cultures were incubated at 37° C. for 1 hour in the presence of both drugs. Cell viability was determined by counting CFUs after 16 hours incubation of washed cell pellets plated onto drug-free agar petri dishes. Intracellular ciprofloxacin was quantified using liquid chromatography coupled to tandem mass spectrometry (LC-MS/MS), as previously described. Non-washed cell pellets were directly frozen and lysed with 350 μl of acetonitrile, followed by three freeze thaw cycles (thawing was performed in an ultrasonic bath for 5 min). Cell debris was pelleted at 16,000 g and the supernatant was filtered through a 0.22 μm syringe filter prior to injection. Chromatographic separation was achieved on a Waters BEH C18 column (2.1×50 mm; 1.7 μm) at 40° C., with a 2 min gradient with flow rate of 0.5 mL/min: (i) 0-0.5 min, 1% mobile phase B; (ii) 0.5-1.2 min, linear gradient from 1 to 95% mobile phase B; (iii) 1.2-1.6 min, 95% mobile phase B; and (iv) 1.6-1.7 min, return to initial conditions (mobile phase A consisted of 0.1% formic acid in water, and mobile phase B consisted of 0.1% formic acid in acetonitrile). Samples were kept at 4° C. until analysis. Sample injection volume was 5 μL. Detection of ciprofloxacin was performed on a Waters Q-Tof premier instrument with electrospray ionization in positive mode. The transition 332>314 was monitored, with cone voltage set at 8 and collision energy set at 20. Intracellular ciprofloxacin was normalized to CFU at the time of ciprofloxacin addition.

Gentamicin

Intracellular gentamicin was quantified by measuring [3H]-gentamicin (1 mCi/ml; Hartmann Analytic Corp.), as previously described. Overnight cultures of *E. coli* MG1655 (ther parental stain of BW25113) were diluted 1:1,000 into 5 ml LB and grown to OD595 nm~0.1. [3H]-gentamicin was diluted in cold gentamicin to get a 5 mg/ml (0.1 mCi/ml) stock solution, which was then added to the culture at a final concentration of 5 μg/ml (0.1 μCi/ml), simultaneously with the second drug: Berberine (200 μg/ml), Erythromycin (15 μg/ml), Metformin (13000 μg/ml), Procaine (6000 μg/ml), Loperamide (400 μg/ml), Benzalkonium (5 μg/ml). Rifampicin (5 μg/ml) or Clindamycin (200 μg/ml). Cultures were then incubated at 37° C. on a rotary shaker. At 0, 0.5, 1, 1.5 and 2 h time-points, 500 μl aliquots were removed and applied to a 0.45 μm-pore-size HAWP membrane filter (Millipore) pretreated with 1 ml of unlabeled gentamicin (250 μg/ml). Filters were washed with 10 ml of 1.5% NaCl, placed into counting vials, and dried for 30 min at 52° C. 8 ml of liquid scintillation were then added to the dried filters and vials were incubated overnight at room temperature before being counted for 5 min. Gentamicin uptake efficiency is expressed as total accumulation of gentamicin (ng) per 108 cells, and plotted here for the final timepoint (2 h) for simplicity. Cell viability was determined by CFUs.

Spectinomycin

Intracellular spectinomycin was quantified by measuring [3H]-spectinomycin (1 μCi/mg; Hartmann Analytic Corp.).

Overnight cultures of *E. coli* BW25113 were diluted 1:1,000 into 1 ml LB with and without vanillin (150 μg/ml) and grown to OD595 nm~0.5. 50 μg/ml [3H]-spectinomycin: spectinomycin 1:100 was added and the cultures were incubated for 1 h. Cultures were pelleted, washed twice with PBS with 50 μg/ml non-labeled spectinomycin, re suspended in 1% SDS and incubated for 20 min at 85° C. The lysate was mixed with 8 ml liquid scintillation (Perkin Elmer ULTIMA Gold) and counted for 1 min using a Perkin Elmer Tri-Carb 2800TR. Measured radioactivity was normalized to cell number as measured by OD595 nm.

RNA Isolation, cDNA Preparation and Quantitative RT-PCR

Overnight cultures of *E. coli* BW25113 and the marR deletion mutant were diluted 1:2,000 into 20 ml LB and grown at 37° C. to OD595 nm~0.2. Aspirin or vanillin were added to the cultures to 500 and 150 μg/ml final concentration respectively (DMSO was added in the control), followed by a 30 min incubation period at 37° C. with agitation. Cells were harvested and RNA extraction was done with the RNeasy Protect Bacteria Mini Kit (Qiagen) according to manufacturer's directions. cDNA was prepared for qRT-PCR using SuperScript™ III Reverse Transcriptase (Thermo Fisher Scientific). marA and mdfA expression levels were estimated by quantitative RT-PCR using SYBR™ Green PCR master mix following the manufacturer's instructions (Thermo Fisher Scientific). Primer sequences for marA and recA are previously described. All experiments were conducted in at least three biological replicates, and relative expression levels were estimated according to Livak et al., using recA expression as reference.

Immunoblot Analysis for Protein Quantification

Overnight cultures of *E. coli* BW25113 and the ΔmarA mutant were diluted 1:1,000 into 50 ml LB containing 500 μg/ml aspirin, 150 μg/ml vanillin or DMSO (drugs solvent control), followed by growth with agitation at 37° C. to OD595 nm~0.5. Cells were washed in PBS containing corresponding drugs or DMSO, then resuspended to match OD595 nm=1. Cell pellets were resuspended in Laemmli buffer and heated to 95° C. for 3 minutes followed by immunoblot analysis with a-AcrA polyclonal antiserum (gift from K. M. Pos) at 1:200,000 dilution. Primary antiserum was detected using anti-rabbit HRP (A0545 Sigma) at 1:5, 000 dilution. Pixel densities of bands were quantified using ImageJ. At least five different biological replicates were blotted and summarized by their mean and standard deviation.

Screening the *E. coli* Keio Knockout Collection for Identifying MoA of Drug Interactions The *E. coli* Keio Knockout Collection (two independent clones per mutant) was arrayed in 1536-format in LB agar plates using a Rotor HDA (Singer Instruments) as previously described. The growth of each mutant was estimated by colony opacity after 13 hours incubation at 37° C. in the absence and presence of vanillin (200 μg/ml), spectinomycin (4 μg/ml), and their combination. All plates were imaged under controlled lighting conditions (spImager S&P Robotics) using an 18-megapixel Canon Rebel T3i (Canon). Experiments were done in triplicates. Fitness of each mutant was calculating by dividing the growth in condition (vanillin, spectinomycin or both) by the growth in LB, after correcting for outer-frame plate effects. Bliss scores were calculated as per Eq. 1 per replicate and then averaged.

Results

High-Throughput Profiling of Drug Combinations in Gram-Negative Bacteria

Gram-negative bacteria cause some of the most difficult-to-treat infections in humans. The inventors selected three γ-proteobacterial species, *E. coli, Salmonella enterica* serogroup *typhimurium*, and *P. aeruginosa*, all belonging to the highest risk group according to the World Health Organization, to study drug-drug interactions and their conservation across closely related species.

Since drug responses can vary between strains of the same species, the inventors selected two strains per species (FIG. 1*a*). The inventors probed each of the strains in up to 79 compounds alone and in pairwise combinations. The drugs consisted of 59% antibiotics from all major drug classes, 23% human-targeted drugs and food additives, most with reported antibacterial and/or adjuvant activity, and 18% of other compounds with known bacterial targets or genotoxic effects—e.g. proton motive force (PMF) inhibitors or inducers of oxidative stress, due to their potential relevance for antibiotic activity and/or uptake (FIG. 1*a*). In total, the inventors profiled up to 2,883 pairwise drug combinations in each of the 6 strains.

Figure 6:
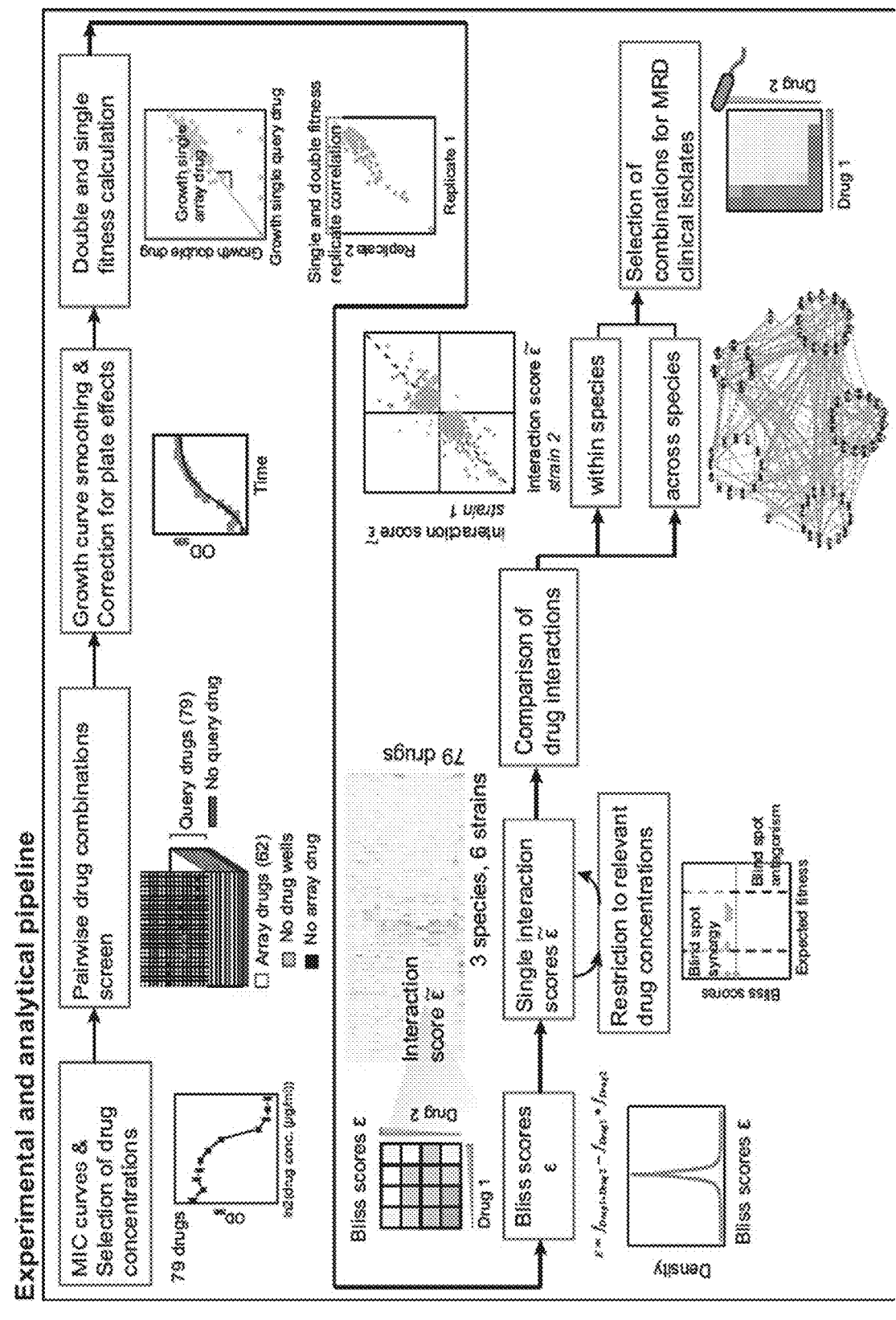
FIG. 6 shows the data analysis pipeline. a) Flowchart of the data analysis pipeline. b) Estimating single drug fitness of arrayed drugs. As drug-drug interactions are rare, the slope of the line of best fit between gaq (growth with double drug) and gq (growth with query drug alone—deduced from average of the top 5% growing wells across plates) across np query drugs (plates) corresponds to a proxy of the fitness of the arrayed drug alone, fa (Eq 3). R denotes the Pearson correlation coefficient between gaq and gq across np plates. Well A9 from *E. coli* BW25113 containing 3 µg/ml spectinomycin is shown as an example of arrayed drugs with several interactions; several query drugs (plates) deviate from the expected fitness (light grey points), therefore only half of the plates corresponding to the interquartile range of fa were used to estimate fa. c) Density distributions of quartiles 1, 2 and 3 of Bliss scores (ε) distributions for *E. coli*. Q1, Q2 and Q3 denote the median of quartiles 1, 2 and 3 of ε distributions, respectively. n denotes the number of drug combinations used.
Figure 6:
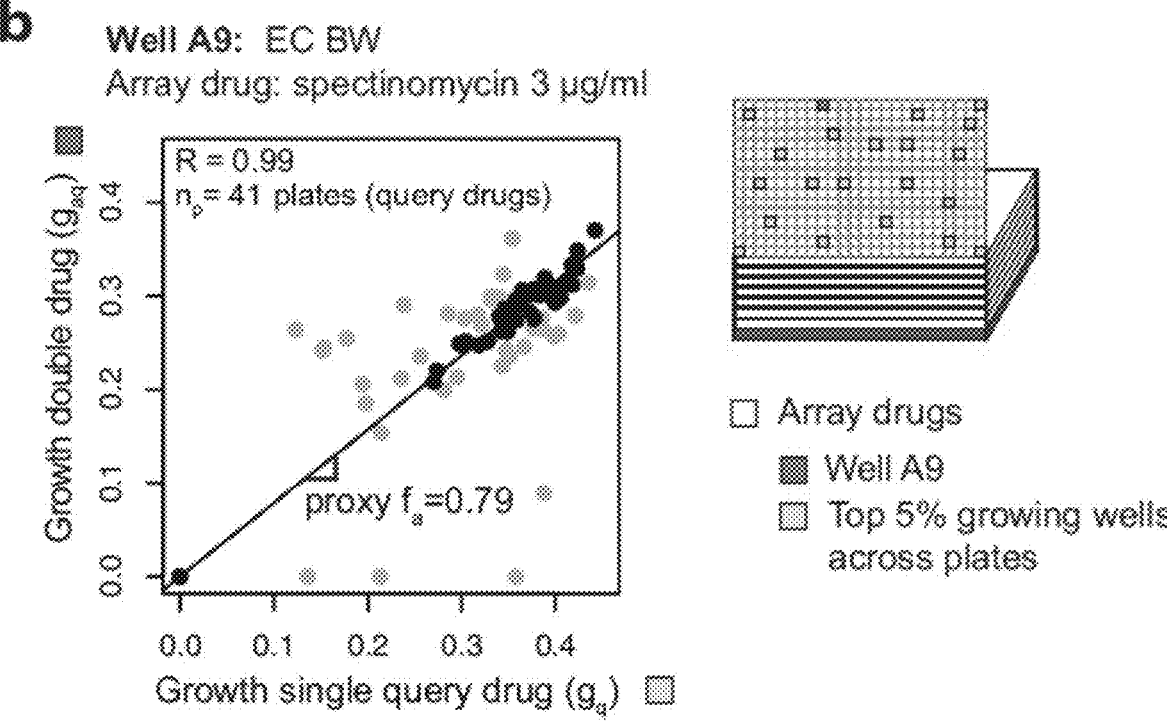
Figure 6:
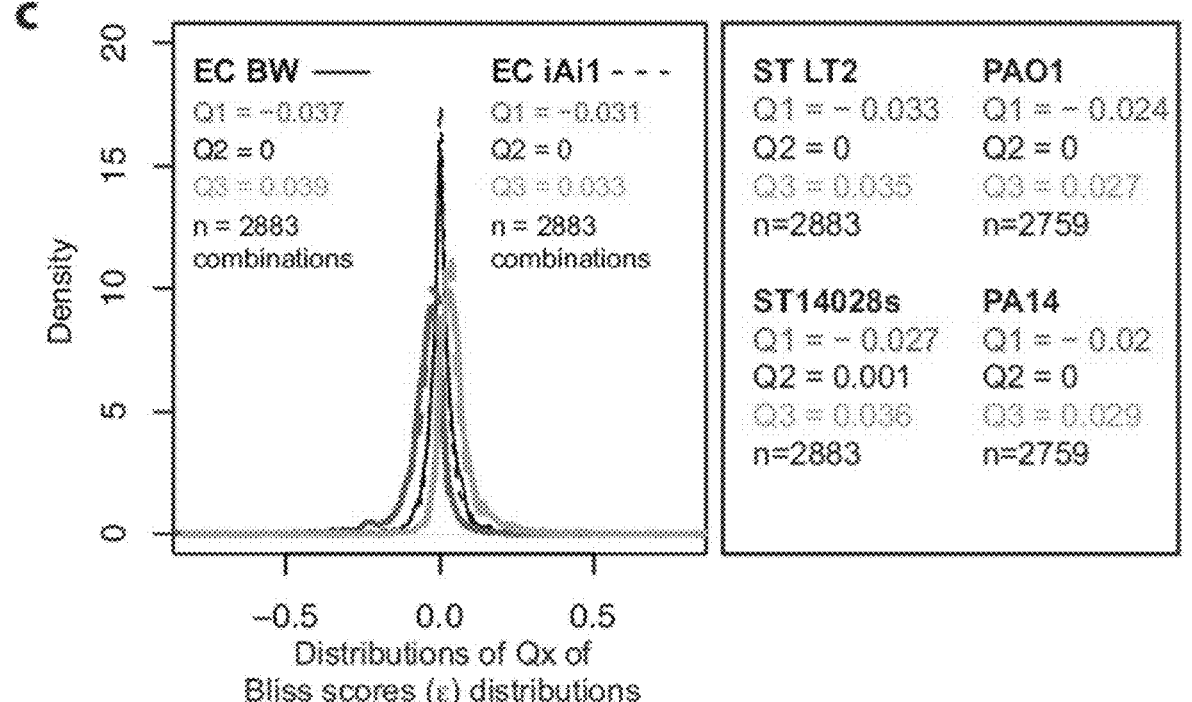

The drugs were pretested in all strains to select appropriate strain-tailored concentrations for the combinatorial screen. The inventors selected three subinhibitory concentrations for each drug: nearly full, moderate, and mild/no growth inhibition—on average, corresponding to 50-100%, 25-50% and 0-25% of the Minimal Inhibitory Concentration (MIC), respectively. Together with the no and single drug controls, the inventors assessed each drug combination in a 4×4 dose matrix using optical density as growth readout, and calculated fitness as the growth ratio between drug treated and untreated cells (FIG. 1, FIG. 6). All experiments were done at least twice and on average 4×, with excellent replicate correlation (average Pearson Correlation=0.93; FIG. 7*a-b*).

The inventors quantified all drug-drug interactions using the Bliss independence model (FIG. 1*b*). In contrast to Loewe additivity, the alternative model for assessing combination therapies, the Bliss model can accommodate drugs that alone have no effect, but potentiate the activity of other drugs (adjuvants). This feature is especially relevant for the inventors' screen, in which the inventors probe intrinsically antibiotic-resistant microbes (*P. aeruginosa* and MDR clinical isolates) and human-targeted drugs or food additives lacking antibacterial activity. Consistent with the null hypothesis of the model, Bliss scores are zero-centered for all species (FIG. 7*c*). From all the Bliss scores (ε) obtained per combination (4×4 dose matrix), the inventors derived a single interaction score & ranging from −1 to 1. This score & reflected the first and third quartile of all Bliss scores within the drug pair. Synergies and antagonisms were considered significant if p-value <0.05 (after Benjamini-Hoch­berg correction of 10,000 permutations of Wilcoxon rank-sum test). Strong interactions had an additional effect size requirement for |ε|>0.1, whereas weak interactions were allowed to satisfy the effect size threshold for one of the two strains of the same species, but be just below for the other (|ε|>0.06; FIG. 3*a*).

In total the inventors detected ~19% of interactions (strong/weak synergies and antagonisms) for *E. coli*, ~16% for *S. typhimurium*, and ~11% for *P. aeruginosa*. This is in between the >70% hit rate for a limited set of antibiotics tested in *E. coli* and the <2% for a larger set of antifungals tested in different fungi. Discrepancies are likely due to: (i) drug selection biases, (ii) single drug concentrations used in previous studies (which can drastically increase false negative and positive rates), and (iii) different data analysis and parameter settings. For example, the inventors observed drugs that do not inhibit growth on their own engage in fewer interactions in the inventor's screen (FIG. 7e). Out of 79 drugs tested here, 69 had at least one interaction in each strain, with a median of 12-13 interactions per drug in *E. coli*, 11 in *S. typhimurium* and 5-6 in *P. aeruginosa* (FIG. 7f).

Figure 9:
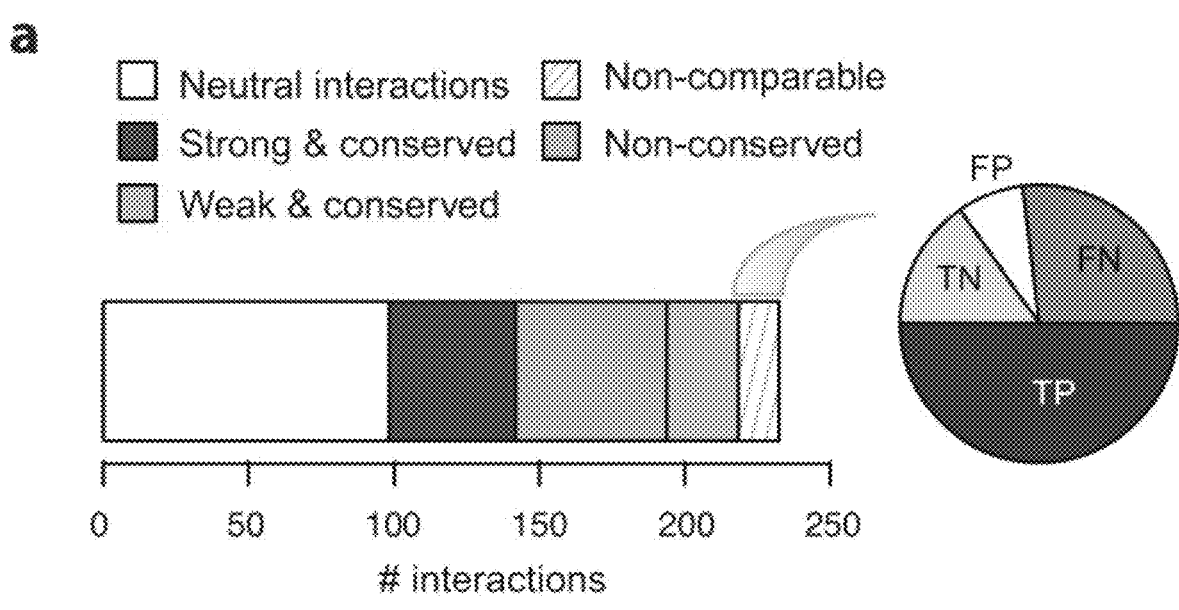
FIG. 9 shows benchmarking of non-comparable drug-drug interactions. a) The barplot illustrates the division of benchmarked drug combinations according to their degree of conservation within species. The pic chart shows the proportion of False and True Positive (FP & TP) and False and True Negatives (FN & TN) within non-comparable drug drug interactions. b) Combination of amoxicillin with cefotaxime in *P. aeruginosa*: an example of a non-comparable drug-drug interaction. The results of the screen are presented on the upper box. Bliss scores as function of expected fitness for both strains are presented on the left hand side, while a density distribution of the Bliss scores is shown on the right hand side. n denotes the total number of Bliss scores, Q1 and Q3 indicate the Bliss score for quartiles 1 and 3, respectively. Antagonism was detected only for PAO1 (Q3>0.1). PA14 was highly resistant to both drugs (upper left panel), rendering detection of antagonism impossible. The benchmarking results indicate that interaction is antagonistic in both strains (lower box), albeit weaker at PA14 and visible mostly at higher concentrations. Color on checkerboard reflects fitness and black dots correspond to drug-ratios where the Bliss score is above 0.1.
Figure 9:
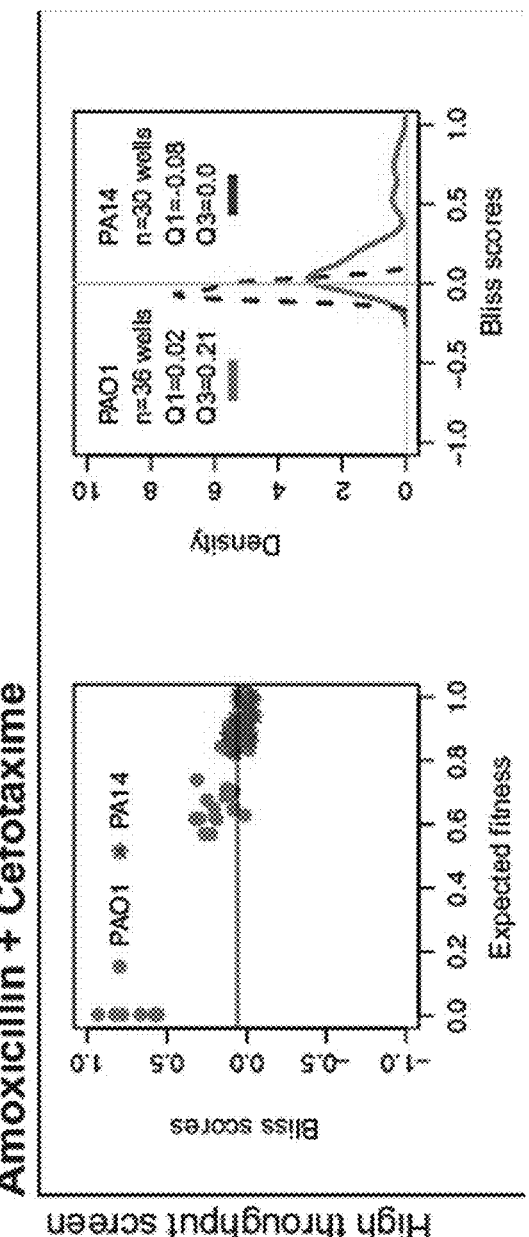
Figure 9:
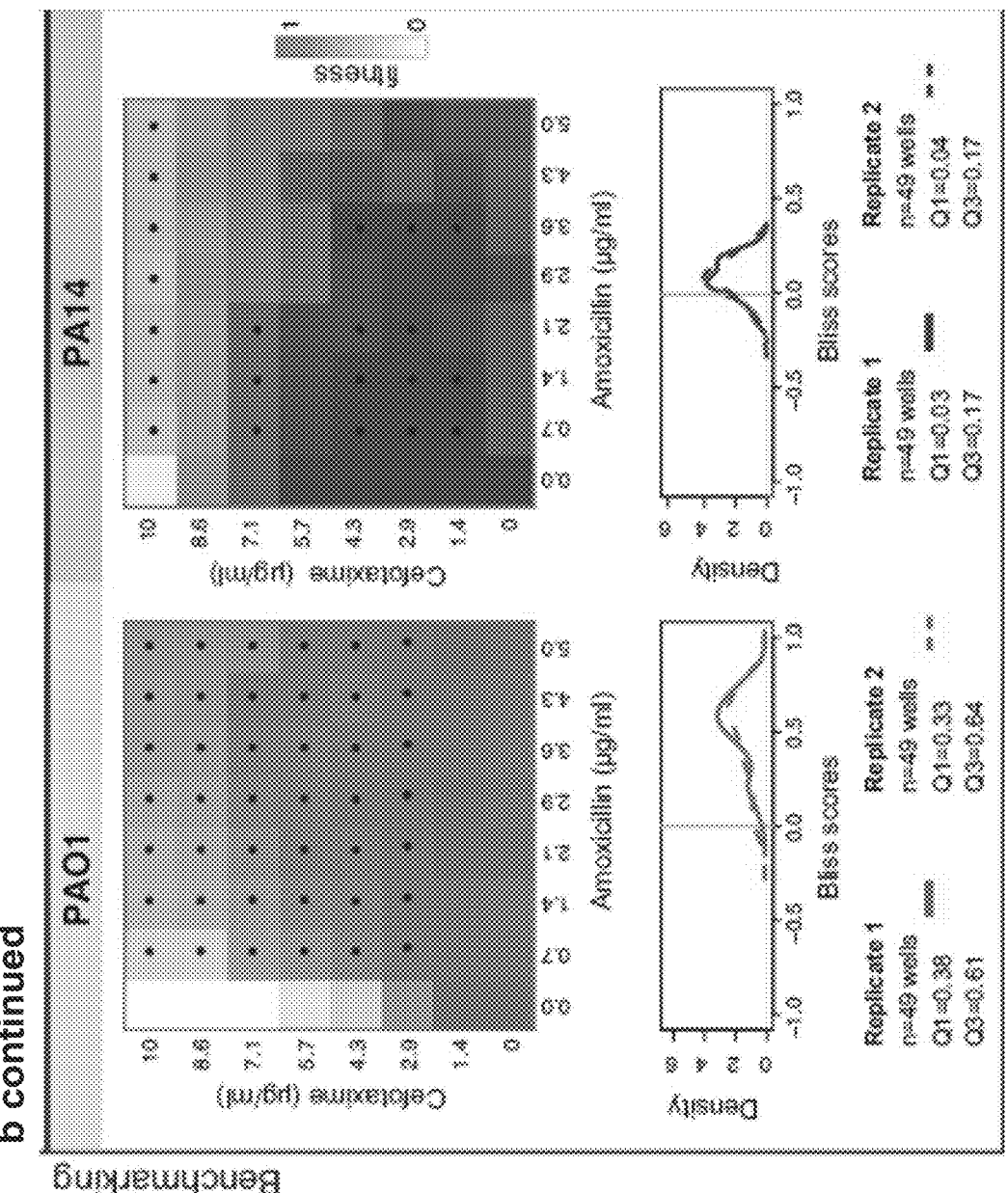
Figure 10:
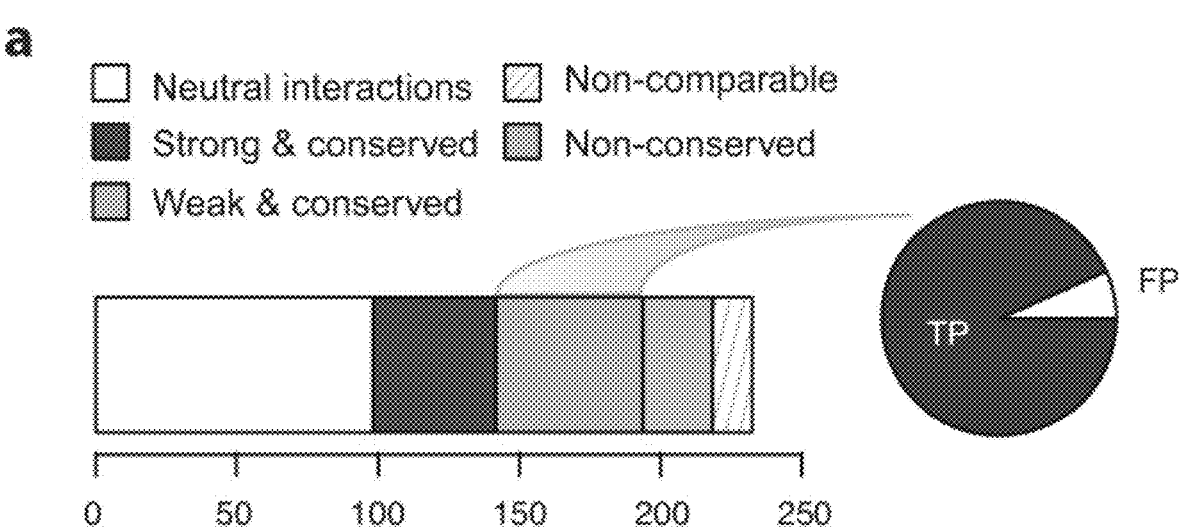
FIG. 10 shows benchmarking of weak conserved drug-drug interactions. a) The barplot illustrates the division of benchmarked drug combinations as in FIG. 9*a*. The pie chart shows the proportion of False Positives (FP) and True Positives (TP) within weak conserved interactions. b) Combination of doxycycline with amikacin in *S. typhimurium*: an example of a weak conserved drug-drug interaction. The results of the screen are presented on the upper box. Bliss scores as function of expected fitness for both strains are presented on the left hand side, while a density distribution of the Bliss scores is shown on the right hand side. n denotes the total number of Bliss scores, Q1 and Q3 indicate the Bliss score for quartiles 1 and 3, respectively. A strong synergy was detected only for ST14028 (Q1<−0.1), and then a weak conserved synergy was assigned afterwards to ST LT2 (Q1<−0.06). The benchmarking results, presented on the box below, confirm that the interaction is synergistic in both strains. Color on checkerboard reflects fitness and black dots correspond to drug ratios where the Bliss score is below −0.1.
Figure 10:
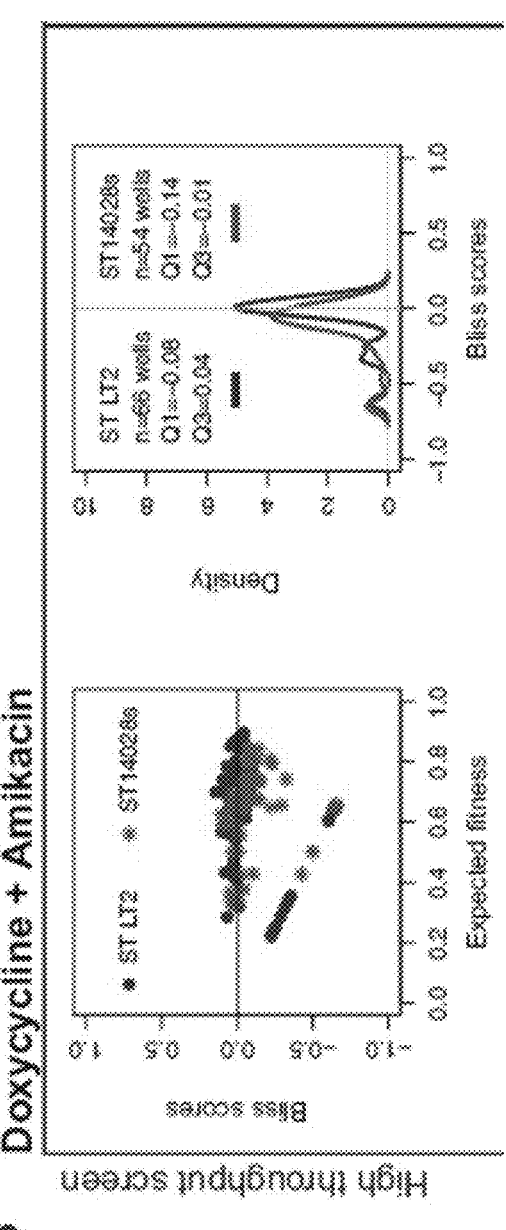
Figure 10:
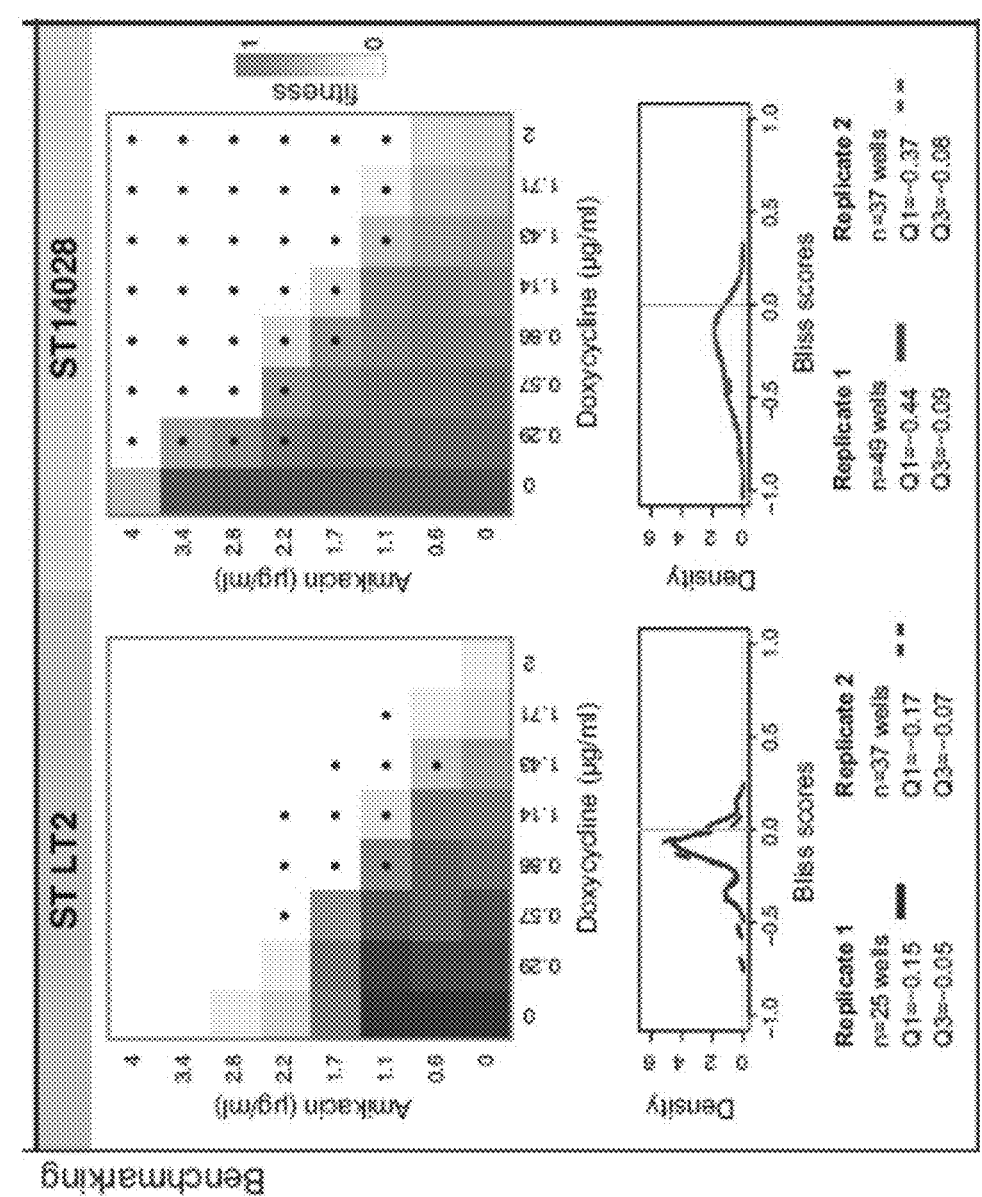

Since drug combinations have not been systematically probed in different bacteria before, the inventors lacked a ground truth for benchmarking their dataset. To overcome this limitation, the inventors selected 242 combinations across the 6 strains, and created a validation set using higher precision 8×8 checkerboard assays (FIG. 8a-b). The inventors used this validation set to both assess the performance of the inventor's interaction identification approach and to benchmark their screen (FIG. 8c-d). Overall, the inventors had precision and recall of 91% and 74%, respectively. The slightly lower recall (inflicted by false negatives) can be partially explained by the larger coverage of drug concentration range in the validation experiments, which increases the inventor's ability to detect interactions (FIG. 9). The inventors further confirmed 90% of all weak interactions they tested (n=46; FIG. 10), validating the rationale of the inventor's interaction identification approach. Indeed, including weak interactions in the inventor's hits contributes to higher recall (FIG. 8d). For a handful of the synergies observed between antibiotics of the same class (ß-lactams), the inventors confirmed the interactions using the Loewe additivity model (FIG. 8e), which is more suitable for assessing interactions between drugs with the same target.

Overall, the inventors had generated a large, high-quality dataset of drug-drug interactions in Gram negative bacteria, probing 17,050 drug combinations in a dose-dependent manner. Having this rich dataset in hand, the inventors looked for general principles governing drug-drug interactions.

Antagonisms and Synergies have Distinct Preferences

Figure 2:
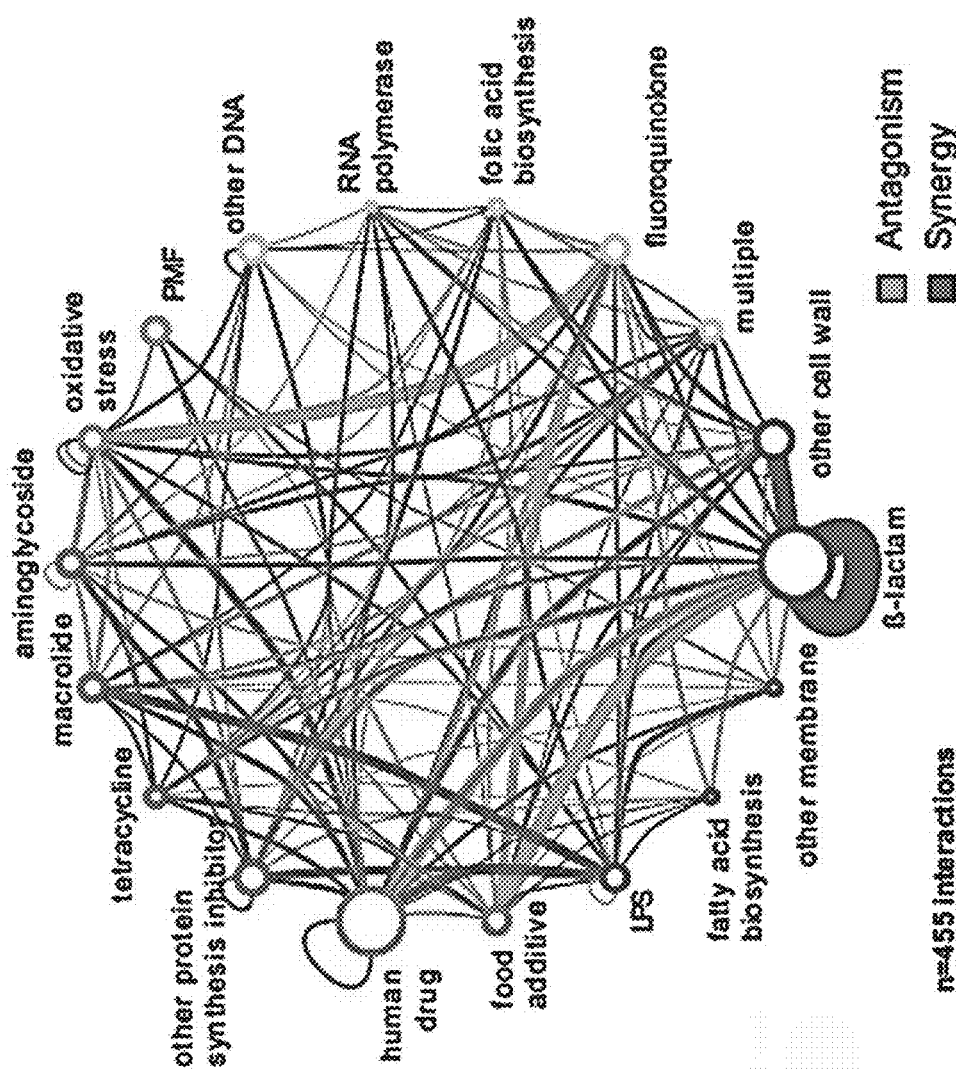
FIG. 2 shows the principles of drug-drug interaction networks. a) Antagonism is more prevalent than synergy. Fraction of observed over detectable synergies and antago- nisms in the 6 strains. The inventors detect more antagonis- tic (1354) than synergistic (1230) interactions, although their ability to detect antagonisms is lower: 12,778 combi- nations versus 16,920 combinations. b & d) Drug-drug interaction networks in *E. coli.* Nodes represent either drug categories (b) or drugs grouped according to the general cellular process they target (d). Node color indicates targeted cellular process according to FIG. 1*a,* and node size reflects the number of drugs within category/group. Edges represent synergy (blue) and antagonism (orange), with thickness reflecting number of interactions between drugs of each category/group. Interactions between drugs of the same category or general cellular target are represented by self- interacting edges. Conserved interactions, including weak, are presented. c & e) Antagonisms occur almost exclusively between drugs belonging to different categories (c) or targeting different cellular processes (e), whereas synergies are also abundant between drugs within the same category (c) or targeting the same process (e). Quantification from *E. coli* drug-drug interactions shown in b and d. Chi-squared test p-values are shown.
Figure 2:
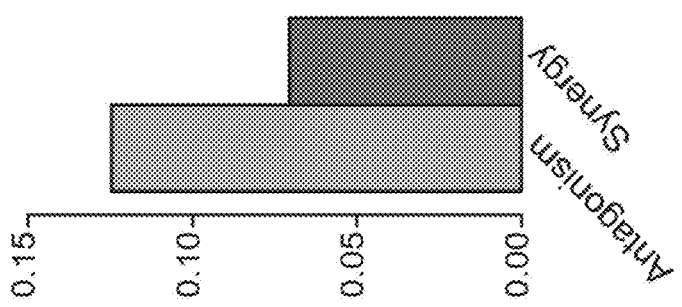
Figure 2:
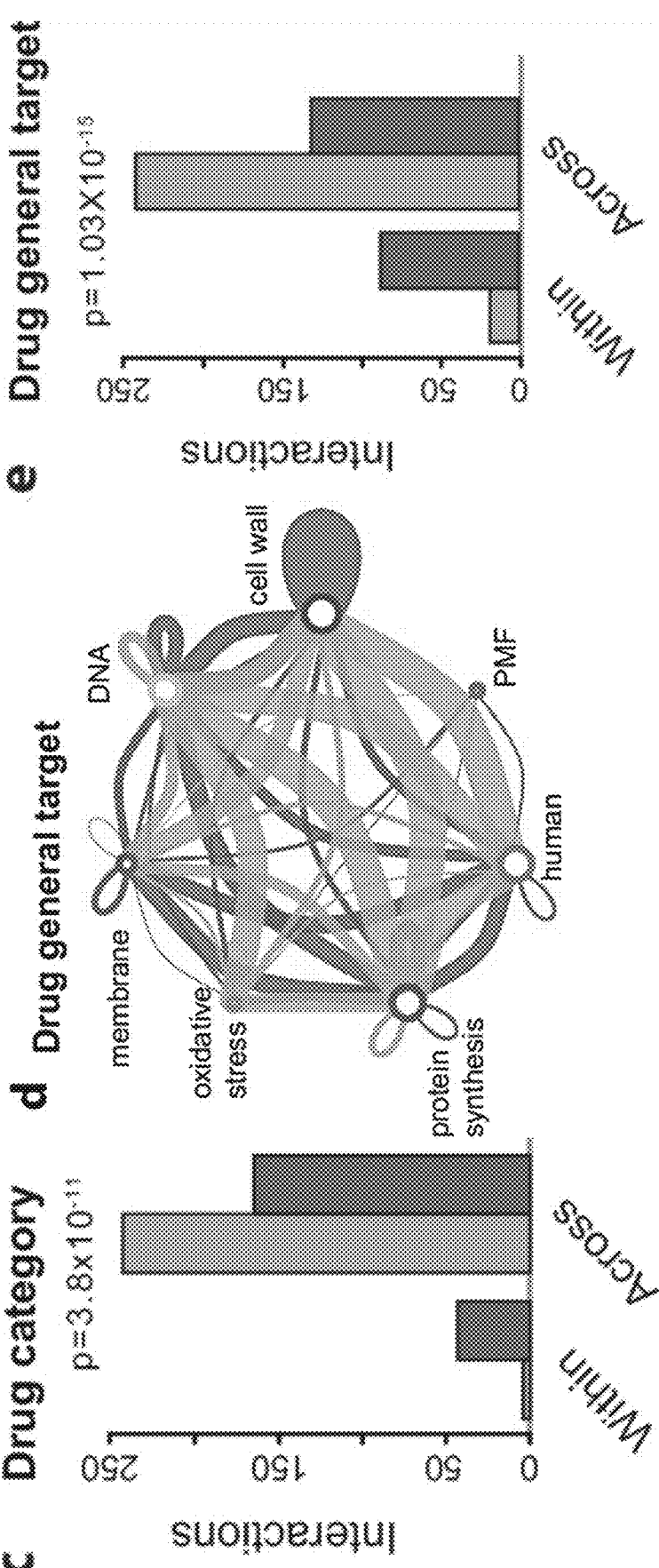

The inventors detected 1354 antagonistic and 1230 synergistic drug-drug interactions across the 6 strains, suggesting that the two occur with similar frequencies. However, antagonisms are nearly 50% more prevalent than synergies, when correcting for the ability to detect both types of interactions (FIG. 2a). This is because the inventors can detect antagonisms only for 75% of combinations (those drug pairs in which at least one individual drug inhibits growth; FIG. 7d), whereas synergies are detectable for nearly all combinations (99%). Higher prevalence of antagonisms has also been reported for antifungals.

Strikingly, antagonisms and synergies exhibited a clear dichotomy in the inventor's data. Antagonism occurred almost exclusively between drugs targeting different cellular processes for all species, while synergies were also abundant for drugs of the same class or targeting the same process (FIG. 2b-e & FIG. 11). Mechanistically, antagonism could be explained by interactions at the drug target level, with the two inhibitors helping the cell to buffer the distinct processes perturbed. DNA and protein synthesis inhibitors act this way in bacteria (FIG. 2b). Consistent with this being a broader phenomenon, in genome-wide genetic interactions studies in yeast, alleviating interactions (antagonisms) are enriched between essential genes (the targets of anti-infectives), which are part of different functional processes. However, antagonism can also arise from cross-protection, e.g. one drug inducing the expression of a pump required for removing a second drug from the cell. The inventors tested 16 antagonistic interactions of different drugs with gentamicin or ciprofloxacin in *E. coli* to investigate to what extent are antagonisms driven by modulation of intracellular drug concentrations (FIG. 12a). Although initially detected at a growth inhibition level, all antagonisms held true at a killing level, with 14/16 decreasing the intracellular gentamicin or ciprofloxacin concentrations (FIG. 12b). In several cases tested, this likely occurred because the second drug either decreased the PMF-energized uptake of gentamicin or increased efflux of ciprofloxacin by inducing the expression of the major efflux pump in enterobacteria, AcrAB-TolC, as antagonisms were neutralized in the respective mutant backgrounds (FIG. 12c). Overall, the inventor's results suggest that a large fraction of antagonisms is due to modulation of intracellular drug concentrations, rather than due to direct interactions of the primary drug targets (FIG. 12d-e).

Figure 11:
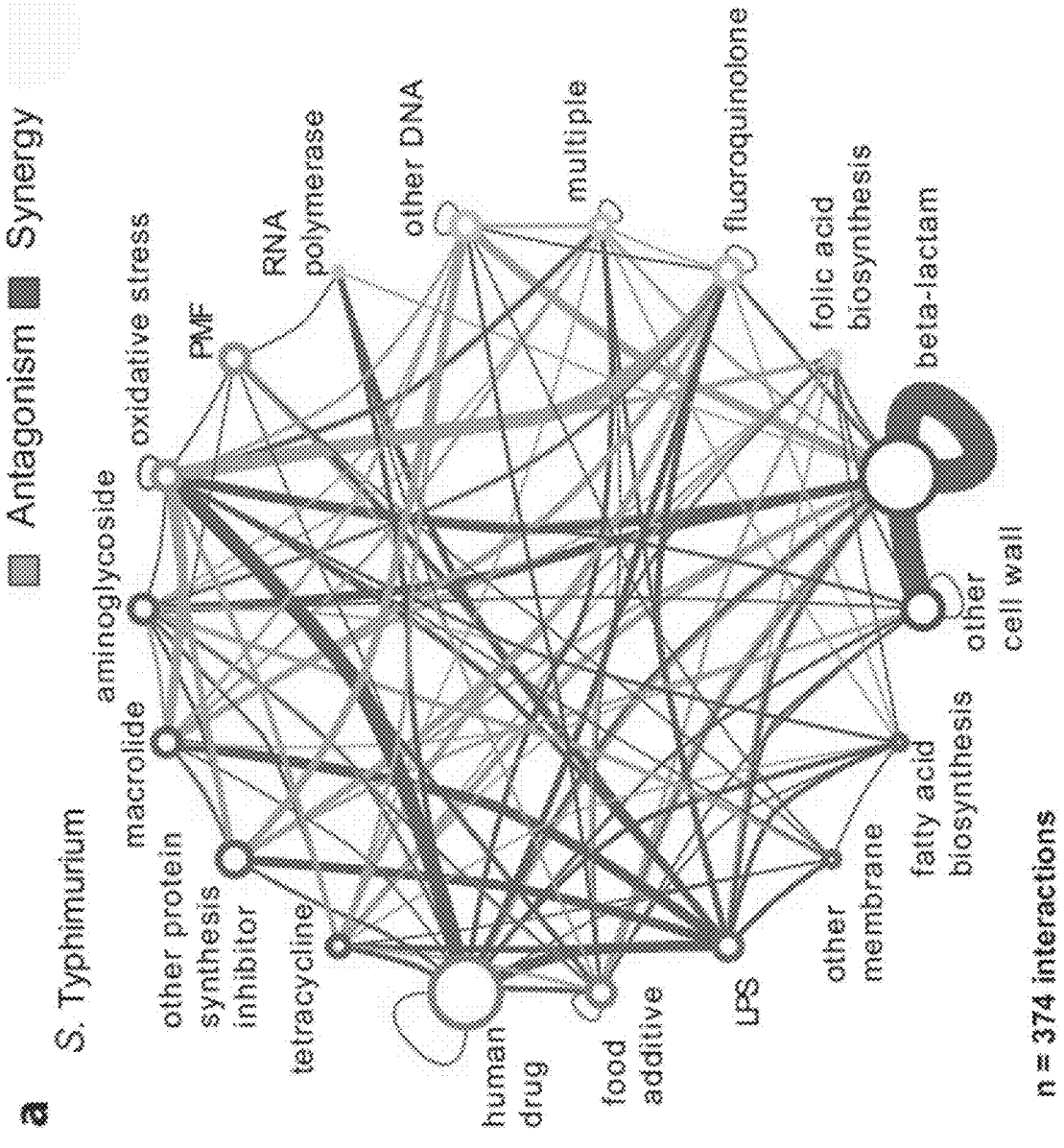
FIG. 11 shows *Salmonella* and *Pseudomonas* drug-drug interaction networks. a & b) Drug category interaction networks. Nodes represent drug categories according to FIG. 1*a*. Node color/size and edge color/thickness are plotted as in FIG. 2*b*. Conserved interactions, including weak conserved, are shown here. c & d) Drug-drug interactions across cellular processes. Representation as in a & b, but drug categories targeting the same general cellular process are grouped here. e) Quantification of synergy and antagonism in the networks from a & b. Chi-squared test p-value is shown. As in *E. coli*, antagonism occurs more frequently than synergy and almost exclusively between drugs belonging to different categories in *S. typhimurium* and *P. aeruginosa*. In *P. aeruginosa*, there are very few interactions occurring between drugs of the same category.
Figure 11:
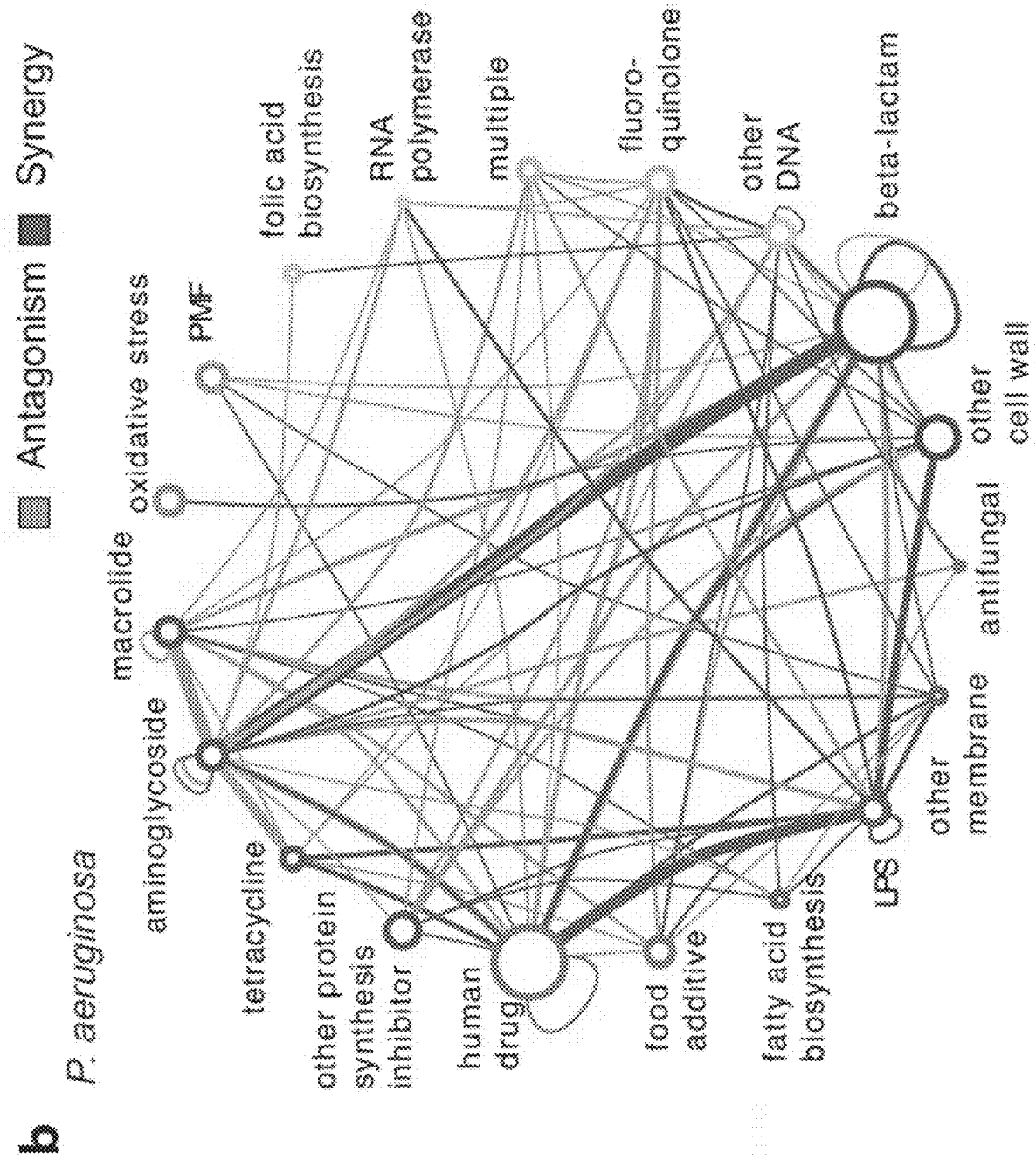
Figure 11:
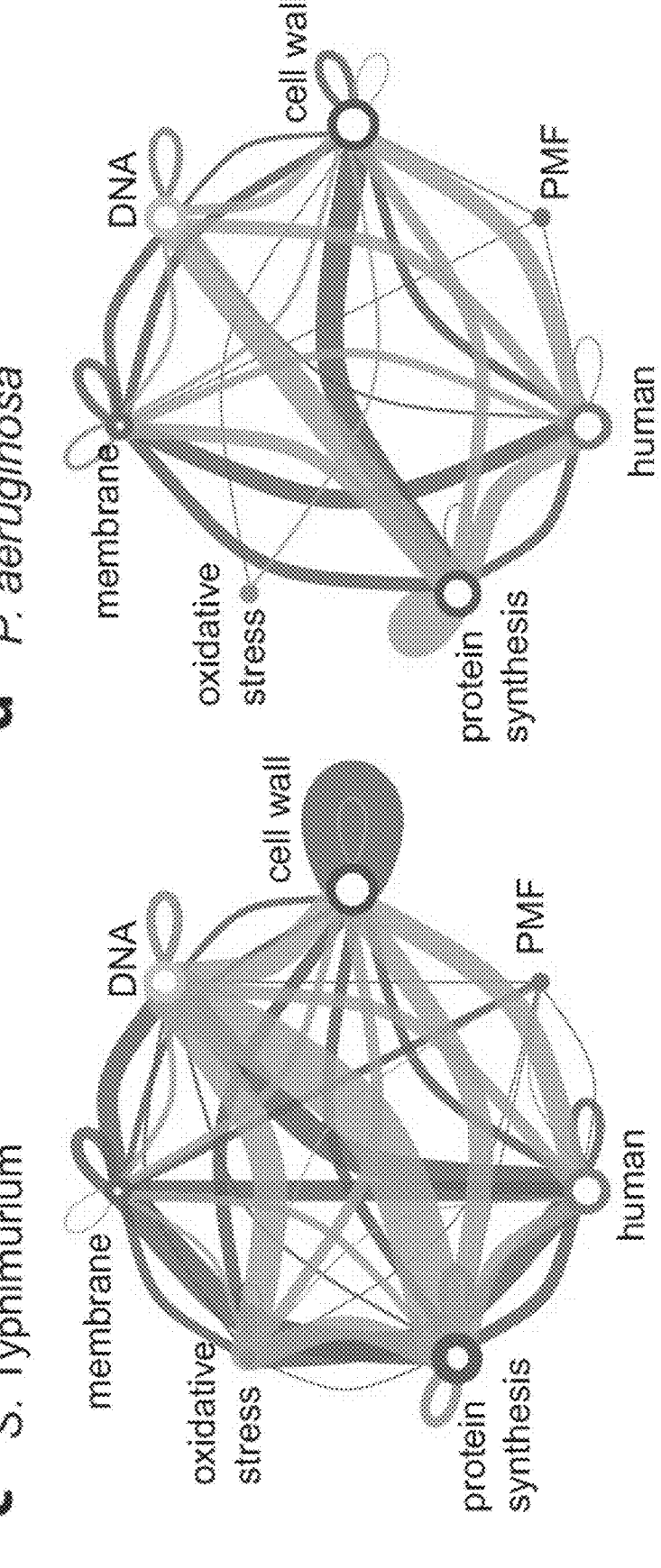
Figure 11:
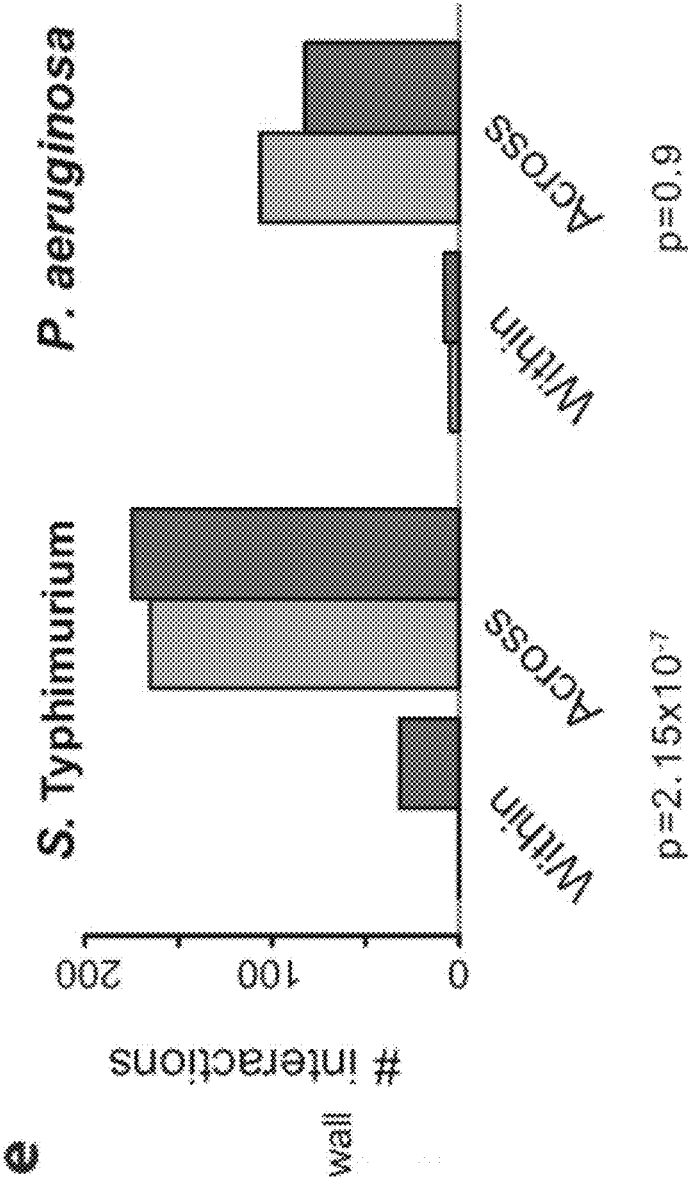
Figure 12:
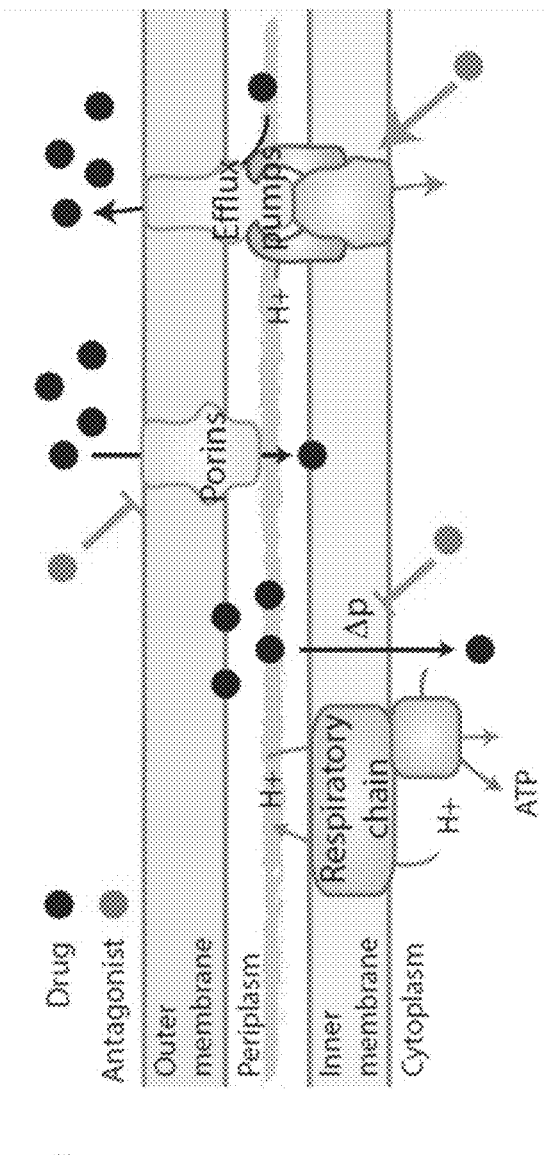
FIG. 12 shows that drug antagonisms are often due to decrease in intracellular drug concentrations. a) Schematic representation of MoA for decreasing intracellular drug concentration (black) via decreased uptake or increased efflux upon addition of a second drug (antagonist; blue). b) Different antagonists of gentamicin (red—5 μg/ml) and ciprofloxacin (gold—2.5 μg/ml) identified in the inventor's screen for *E. coli* BW also rescue the killing effect of the two bactericidal drugs in the same strain or its parental MG1655 (top right and left panels, respectively). With the exception of clindamycin (for gentamicin) and curcumin (for ciprofloxacin), all other antagonists decrease the intracellular concentration of their interacting drug (bottom panels)— gentamicin detected by using radiolabeled compound and ciprofloxacin with LC-MS/MS. The degree of rescue (upper panel) mirrors the decrease of intracellular concentration (lower panel), implying that most of these interactions depend to a large extent on modulating the intracellular concentration of the antagonized drug. c) Antagonisms are resolved in *E. coli* BW mutants lacking key components controlling the intracellular concentration of the antagonized drug. Aminoglycosides depend on PMF-energized uptake and thus respiratory complexes; ciprofloxacin is effluxed by AcrAB-TolC. For gentamicin, most interactions are resolved when respiration is defected, even the one with clindamycin (not modulating intracellular gentamicin concentration—see panel (b)) presumably because MoA and import of amino-glycosides are linked in a positive feedback loop. For ciprofloxacin, antagonisms with paraquat and caffeine are resolved in the ΔacrA mutant, implying that both com-pounds induce the AcrAB-TolC pump (known for paraquat). In contrast, interactions with curcumin, benzalkonium and doxycycline remain largely intact in the ΔacrA mutant. First is expected as curcumin does not modulate intracellular ciprofloxacin concentration (see panel b). In other two cases, other component(s) besides AcrAB-TolC are likely respon-sible for the altered ciprofloxacin import/export. Ciprofloxa-cin and gentamicin concentrations were adjusted in all strains according to MIC (70% and 100% MIC for cipro-floxacin and gentamicin, respectively). Bliss interaction scores ($\varepsilon$) were calculated as in the screen and are repre-sented by the mean and standard deviation across 3-8 replicates. d) Gentamicin and ciprofloxacin antagonism net-works for E. coli BW. Nodes represent drugs colored accord-ing to targeted cellular process (as FIG. 1a). Full and dashed edges represent antagonistic drug-drug interactions for which intracellular antibiotic concentration was and was not measured, respectively. Drug interactions that result in decreased intracellular concentration of the antagonized drug are represented by black edges. e) Quantification of antagonistic drug-drug interactions from the networks in (d). The bars for fluoroquinolones and aminoglycosides account for an extrapolation of antagonistic interactions to all other members of the two classes, assuming they behave the same as ciprofloxacin and gentamicin, respectively.
Figure 12:
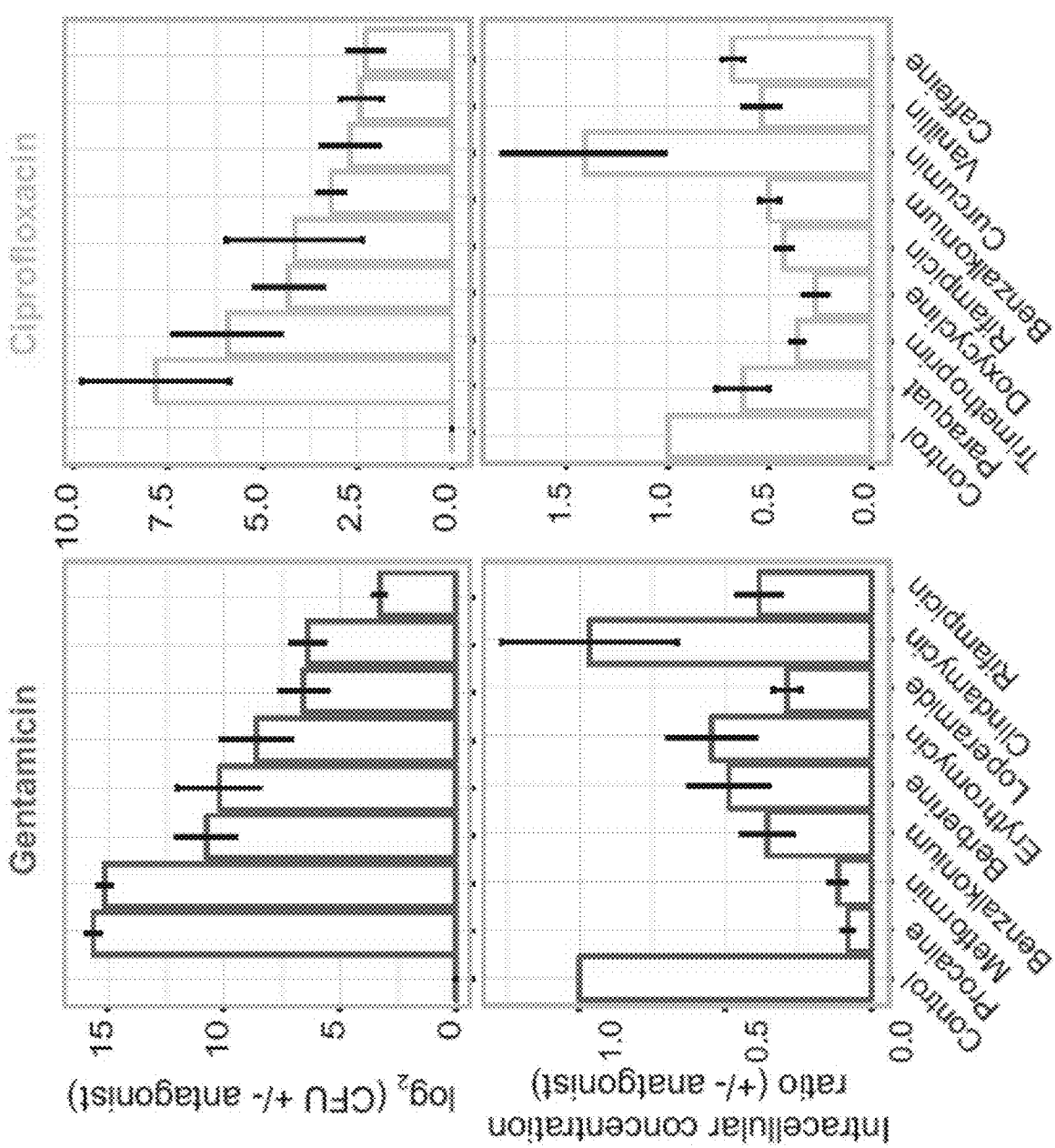
Figure 12:
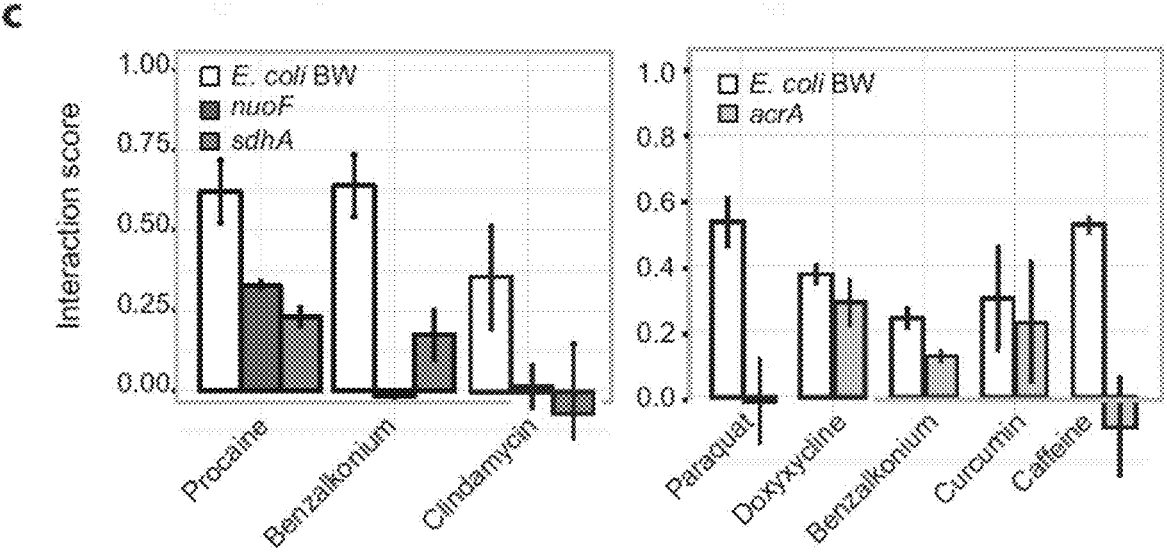
Figure 12:
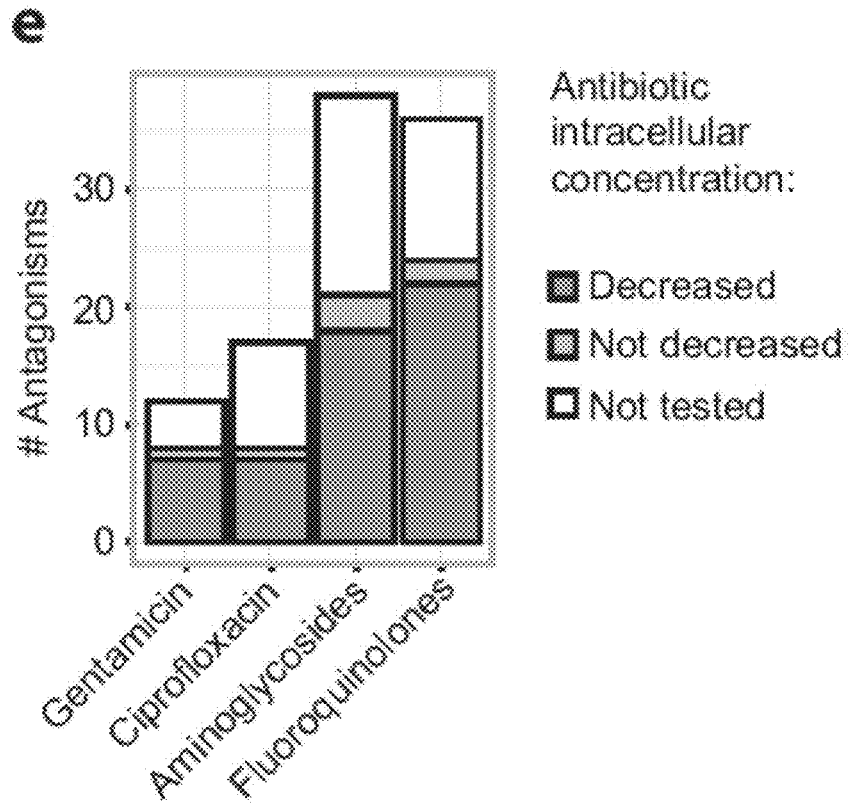
Figure 12:
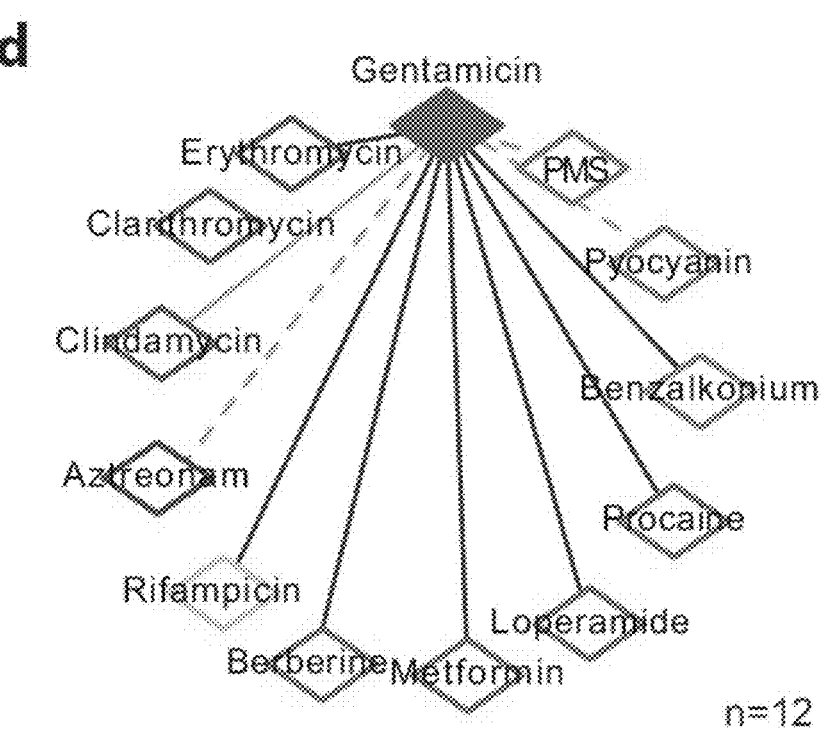
Figure 12:
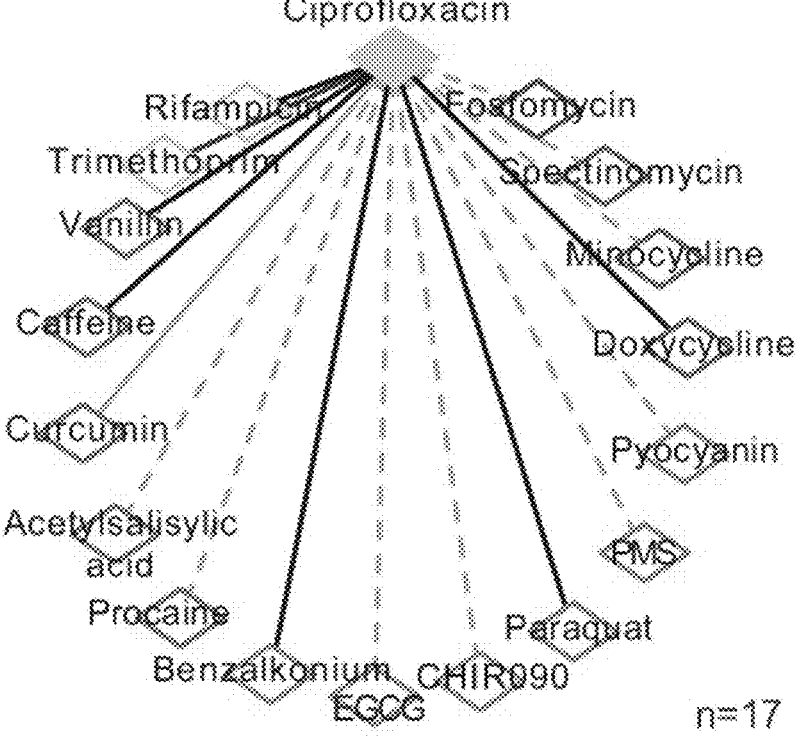

Unlike antagonistic interactions, synergies often occurred between drugs targeting the same cellular process (FIG. 2b-c & FIG. 11). In fact, synergies are significantly enriched within drugs of the same category across all three species (p-value <10-16, Fischer's exact test), given that there are ~15-fold more possible drug combinations across drug categories in the inventor's dataset. Mechanistically, targeting the same functional process at different steps could tease apart its redundancy. For example, ß-lactams have different affinities to the numerous and often redundant penicillin-binding-proteins (PBPs), likely explaining the many synergies between them (FIG. 2b, FIGS. 8e & 11a-b).

Like antagonisms, synergies can also occur due to modulation of intracellular drug concentrations. Consistent with a general permeabilization role of membrane-targeting compounds in many organisms, and with drug uptake being a major bottleneck for Gram-negative pathogens, one fourth of all detected synergies contain at least one out of eight membrane-targeting drugs in the inventor's screen (Wilcoxon rank-sum test, p-value=0.044). For example, hydrophobic macrolides have difficulties in passing the negatively charged surface of the outer membrane (OM), but can be potentiated by polymyxins, which disrupt the OM by binding to lipopolysaccharide (LPS). However, membrane-targeting compounds account also for ~16% of antagonisms, suggesting that perturbations in membrane integrity can also decrease intracellular drug concentrations. Consistently, benzalkonium decreases the intracellular concentration of both gentamicin and ciprofloxacin, likely because it interferes with their import in the cell (FIG. 12b-c). One of the most well-known and broadly used synergies is that of aminoglycosides and ß-lactams. Consistent with its use against *P. aeruginosa* in clinics, the inventors detected multiple strong synergies between specific members of the two antibiotic classes in *P. aeruginosa*, but fewer interactions in the other two species (FIG. 2b, FIG. 11a-b).

Drug-Drug Interactions are Largely Species-Specific

The inventors examined the conservation of drug-drug interactions. Interactions within species were highly correlated (FIG. 3a & FIG. 13a-b), with conservation ranging from 53% to 76%, depending on the species (FIG. 3b). Conservation is actually higher (68-87%, and on average 80%), if the inventors disregard the non-comparable interactions for which the concentration range tested preclude detecting synergy or antagonism for both strains (FIG. 3b & FIG. 7d). High conservation of drug-drug interactions within species is in agreement with the finding that such interactions are generally robust to simple genetic perturbations. Despite the overall high-degree conservation within species, 13-32% of the interactions were strain-specific, with the majority being neutral in the second strain. Very few drug combinations synergized for one strain and antagonized for the other (16 interactions), but such strain differences persisted in the inventor's validation set.

While conservation is relatively high within species, it is very low across species (FIG. 3c-d). The vast majority (70%) of interactions occurred in one out of three species, and only 5% of the drug-drug interactions were conserved in all three phylogenetically close-related species. Since conservation is much higher at the single drug level for the three species (sharing resistance/sensitivity to 73% of the drugs), this indicates that drug combinations can impart species specificity to the drug action. Such specificities can be beneficial for creating narrow spectrum therapies with low collateral damage, by using synergies specific for pathogens and antagonisms specific for abundant commensals.

The inventors then explored the conserved drug-drug interaction network at the individual drug level for all three species (FIG. 3e). This exposed conserved Achilles heels of Gram-negative bacteria, such as the strong synergy of colistin with macrolides, but also revealed that known antibiotic classes often behave non-uniformly. For example, the known synergy between ß-lactams and aminoglycosides is confined to potent aminoglycosides used in the inventor's screen (amikacin and tobramycin) and ß-lactams that target specifically the cell-division related PBPs (piperacillin, aztreonam, cefotaxime), in agreement with previous reports. Moreover, many of the human-targeted drugs, such as loperamide, verapamil and procaine exhibit a general potentiating effect, similar to that of membrane-targeting drugs, suggesting that they may also facilitate drug uptake or impair efflux, consistent with previous reports on the role of loperamide in *E. coli* and verapamil in *Mycobacterium tuberculosis*.

Finally, the inventors found that synergies are significantly more conserved than antagonisms (FIG. 3f), despite being less prevalent (FIG. 2a). This is presumably because: i) synergies are enriched between drugs of the same category, and interactions within functional processes have been previously shown to be conserved across evolution; ii) membrane-targeting drugs have a general potentiation role across Gram-negative bacteria—helping drugs cross the OM, and iii) antagonisms often depend on drug import/ uptake (FIG. 12), which are controlled by less conserved envelope machineries.

Drug-Drug Interaction Profiles Reveal Drug Mode-of-Action & Chemical Properties

Pairwise drug interactions have been considered to be Mode-of-Action (MoA)-driven, with drug classes interacting purely synergistic or antagonistic with each other. Since drug members of the same category exhibited distinct interactions in the inventors' conserved drug-drug interaction network (FIG. 3e), the inventors decided to address this more systematically by calculating a monochromaticity index (MI) for all drug category pairs across all species, and independently of whether interactions were conserved. MI equals zero when interactions between two drug categories have the same proportion of synergy and antagonism as all interactions together. For highly monochromatic category pairs, MI approaches 1 and −1 for antagonism and synergy, respectively. MI is overall high, especially between well-defined antibiotic classes. Yet, a number of them, including ß-lactams, tetracyclines and macrolides, have mixed antagonisms and synergies with other antibiotic classes (FIG. 13c). While ß-lactams have diverse affinities to their multiple PBP targets (potentially explaining the mixed interactions with other classes), the same does not apply to protein synthesis inhibitors, which have unique targets. In this case, non-uniform class behavior may be due to different chemical properties of the class members, and thus different dependencies on uptake and efflux systems. Aggregating the MI per drug category reinforced the view that broader categories exhibit less concordant interactions (FIG. 13d). Interestingly, human-targeted drugs were the largest category exhibiting predominantly synergies, supporting the hypothesis that many human-targeted drugs may act as adjuvants.

Figure 4:
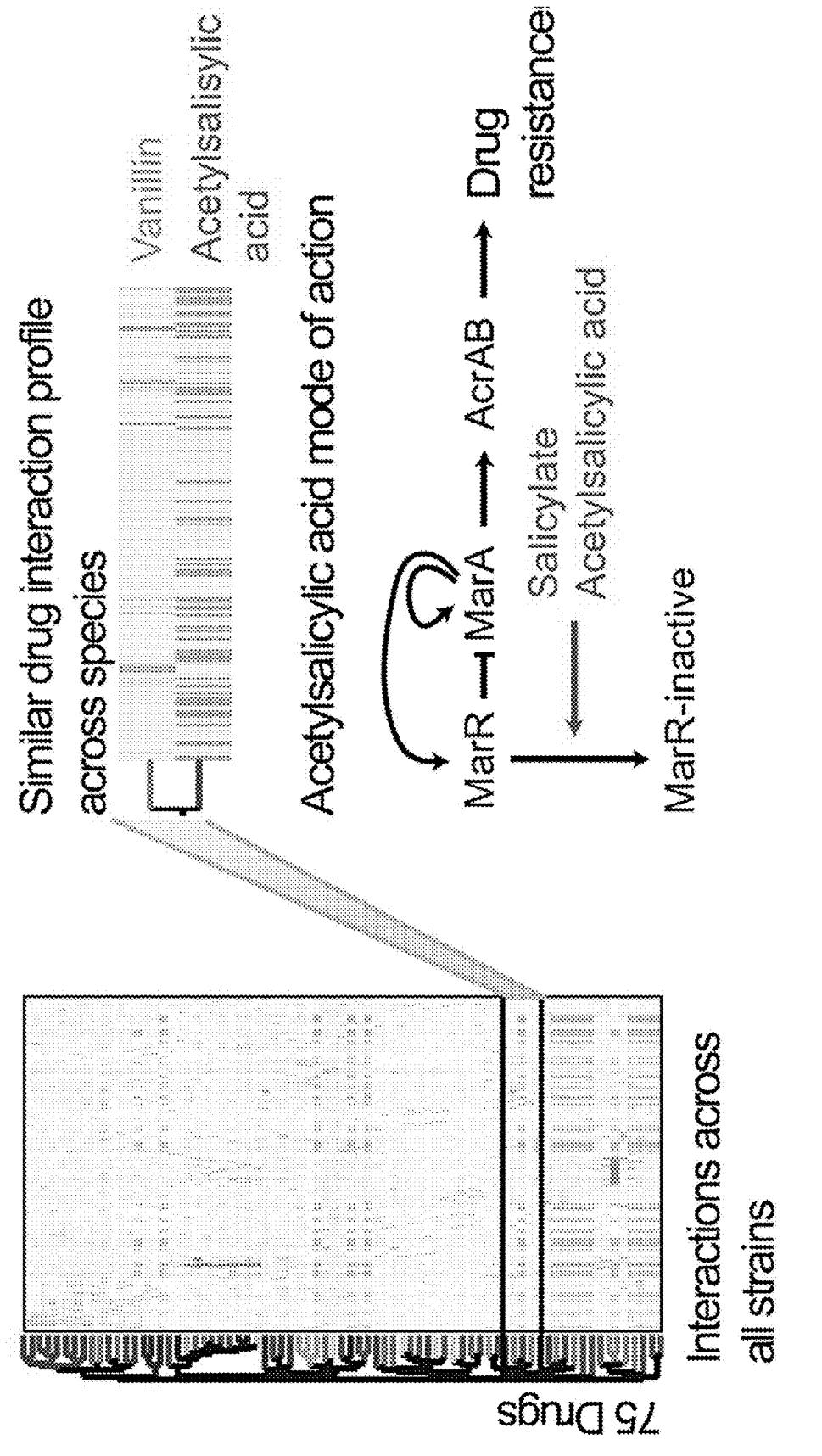
FIG. 4 shows that Vanillin induces a multi-antibiotic-resistance (mar) phenotype. a) Vanillin and aspirin (acetyl-salicylic acid) have similar drug-drug interaction profiles (see FIG. 14), suggesting common MoA's. A schematic representation of the mar response induction via deactivation of the MarR repressor by salicylate/aspirin is illustrated. b) Vanillin increases AcrA protein levels in a marA-dependent manner. A representative immunoblot of exponentially growing cells, untreated or after treatment with vanillin (150 µg/ml) or aspirin (500 µg/ml) is shown—loading controlled by cell density and constitutively expressed RecA. Barplots depict AcrA protein level quantification; n=5-6. c) marA expression levels upon vanillin (150 µg/ml) or aspirin (500 µg/ml) treatment are stronger in wildtype than in ΔmarR mutant. Expression is measured by RT-qPCR and normalized to no-drug treatment in wildtype; n=4. d & e) Vanillin (150 µg/ml) and aspirin (500 µg/ml) increase the MIC of chloramphenicol (d) or ciprofloxacin (c). Antagonism is weaker and abolished in ΔmarA and ΔacrA mutants, respectively; n=3. Error bars depict standard deviation (b-e).
Figure 4:
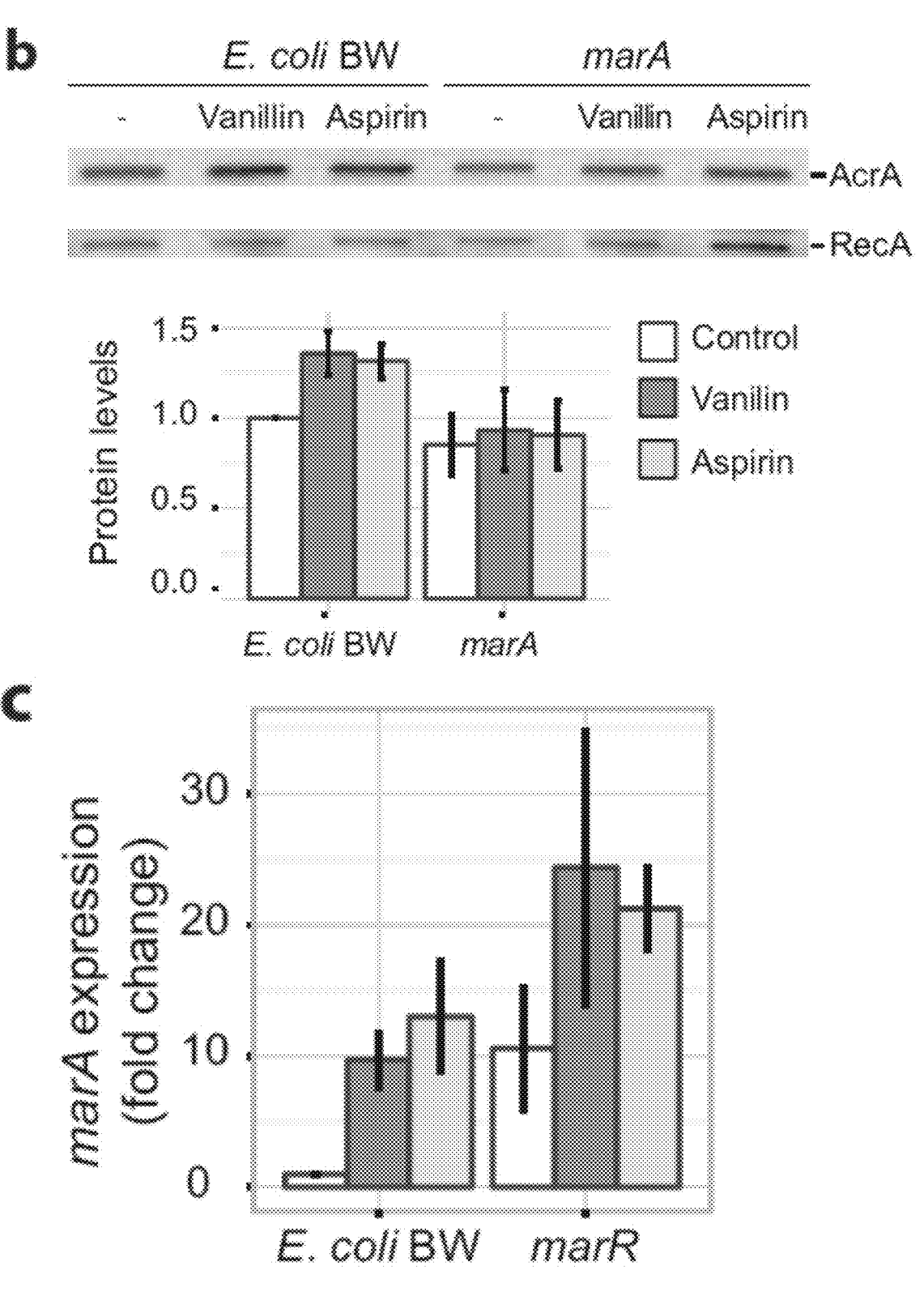
Figure 4:
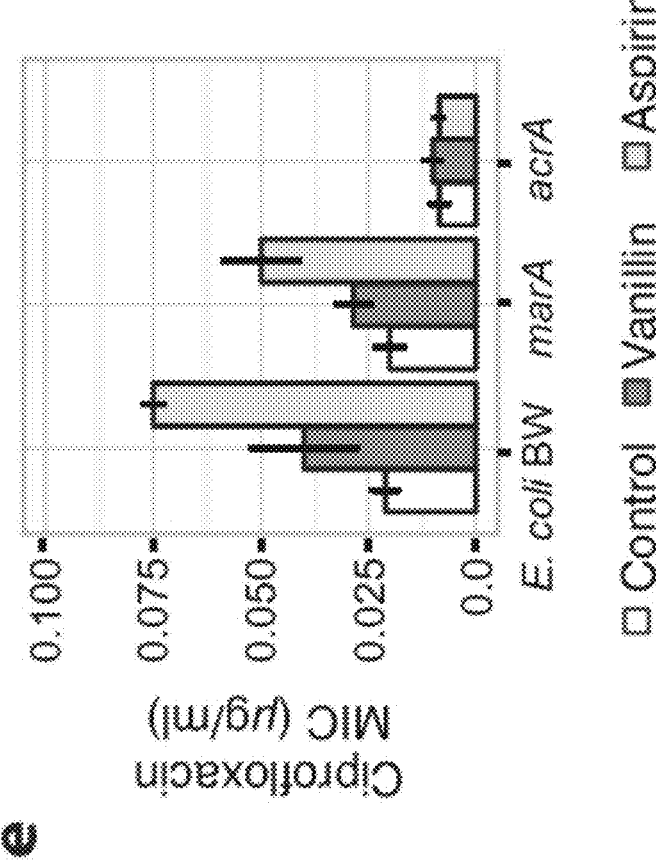

Among the drugs tested, the inventors selected the flavoring compound vanillin, which clusters together with the structurally related acetylsalicylic acid (aspirin). Salicylate and aspirin induce the expression of the major efflux pump in enterobacteria, AcrAB-TolC via binding and inactivating the transcriptional repressor MarR (FIG. 4a). Consistent with a similar action, vanillin treatment increased AcrA protein levels in *E. coli*, due to marA overexpression (FIG. 4b-c). Higher AcrA levels upon vanillin or aspirin treatment led to higher chloramphenicol and ciprofloxacin MICs (FIG. 4d-e). As previously reported for salicylate, vanillin exerts an additional minor effect on drug resistance in a MarR/A-independent manner, presumably via the MarA homologue, Rob (FIG. 4c-e).

Overall, the inventor's data suggest that drug-drug interactions can be used for MoA identification, although interactions depend not only on drug target, but also on drug uptake and efflux, which are tightly linked to drug chemical properties. This is consistent with studies on the mechanism of drug-drug interactions or on computationally predicting their outcome.

Effective Drug Synergies Against MDR Clinical Isolates

Figure 14:
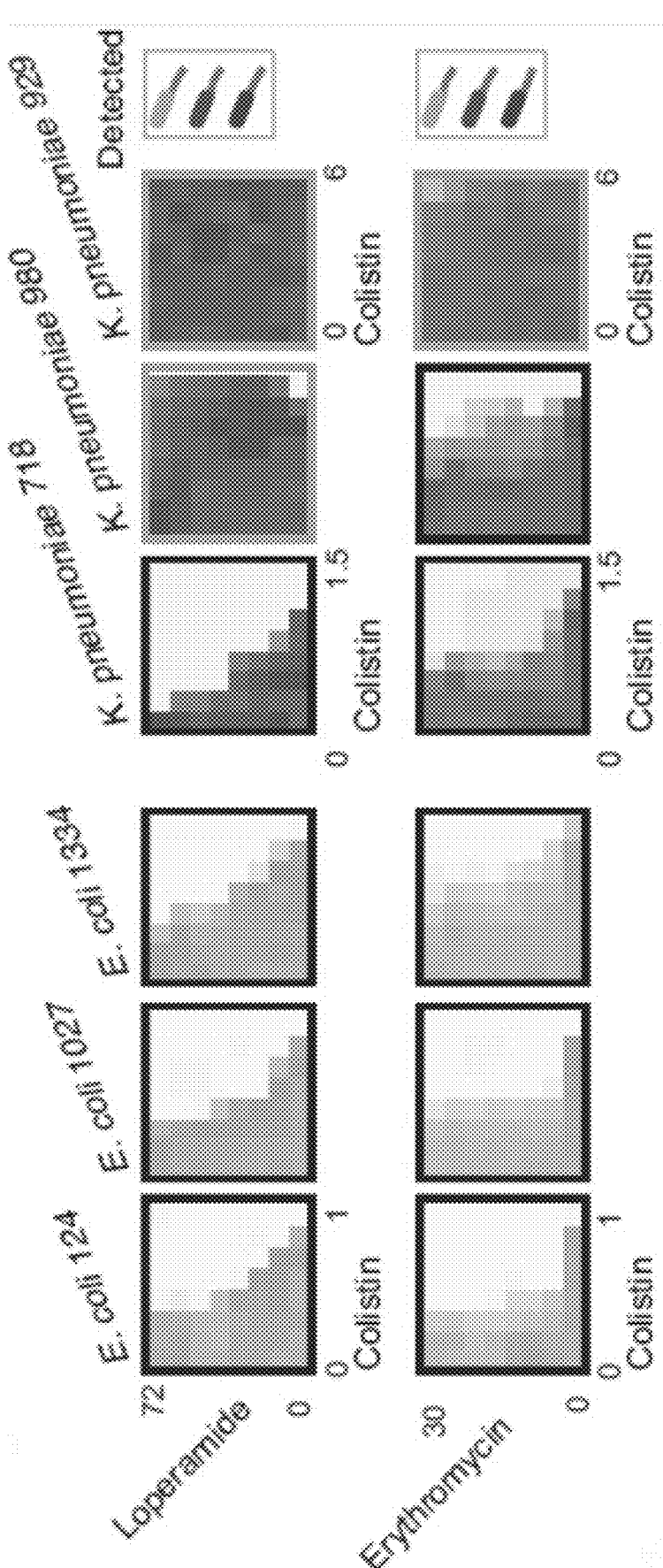
FIG. 14 shows active synergies against Gram-negative MDR clinical isolates. a) Additional drug combinations against MDR E. coli and K. pneumoniae clinical isolates (related to FIG. 5a). Interactions are shown as 8×8 check-erboards and synergies have a black bold border. Drug pairs are the same per line and indicated at the first checkerboard. The species in which interaction was detected in the screen are indicated after the last checkerboard. Concentrations increase on equal steps per drug (sec key); only minimal and maximal concentrations are shown in μg/ml for the first strain of each species. Apart from colistin, the same concentration ranges were used for all E. coli and K. pneumo-niae MDR strains. One of two replicates is shown.
Figure 14:
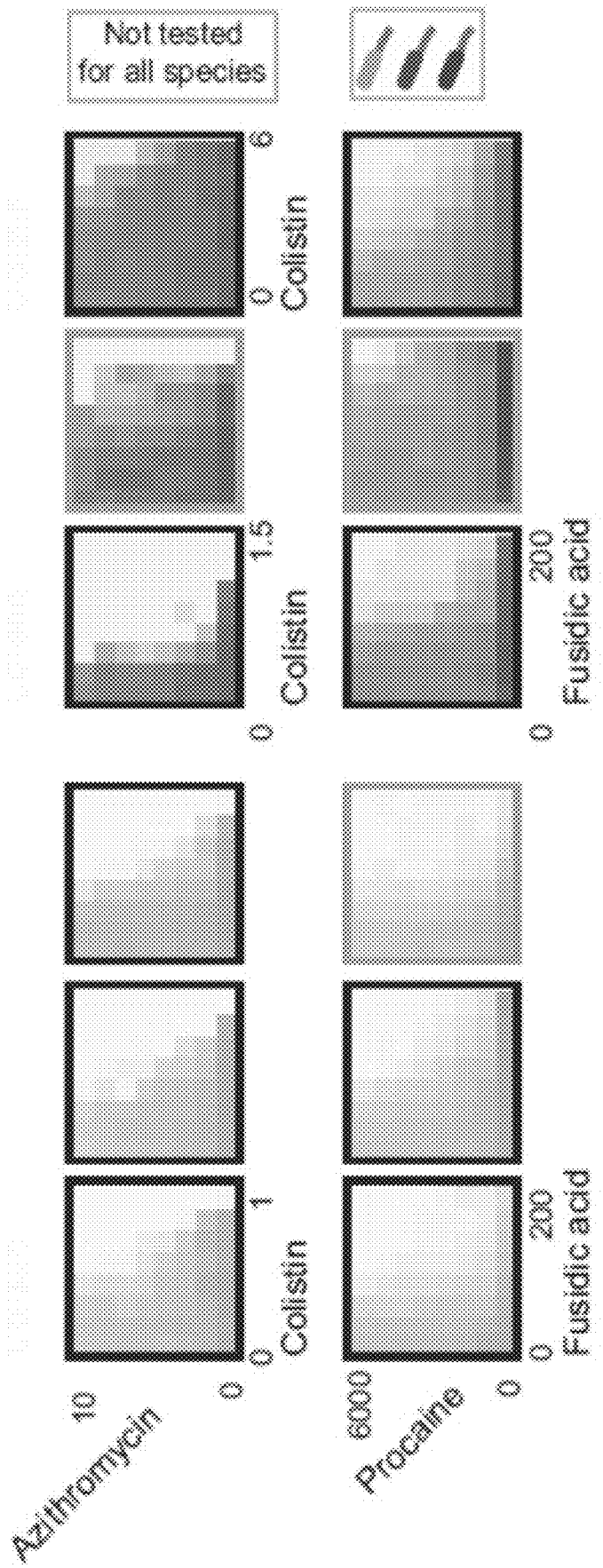
Figure 14:
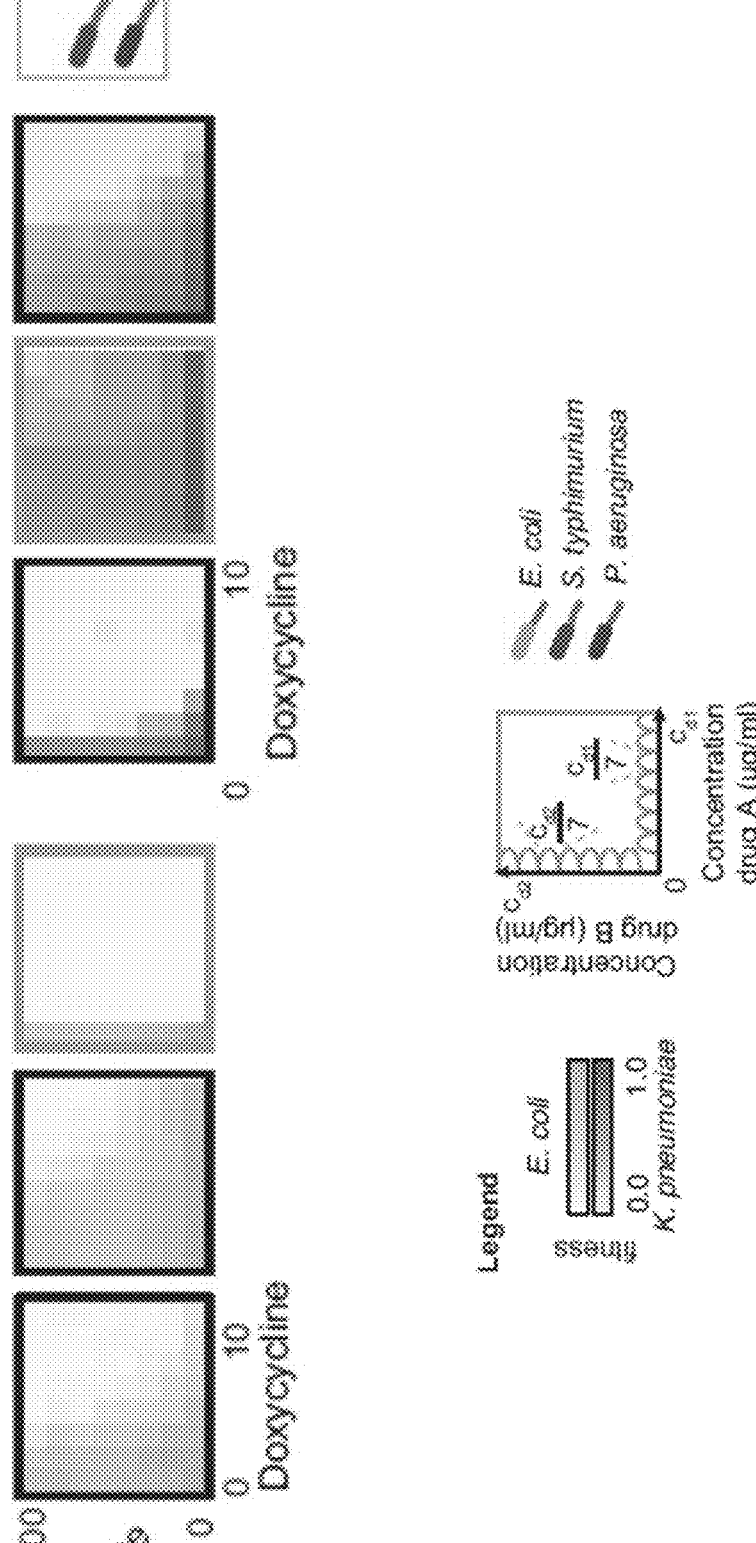

To test whether the interactions the inventors detected are relevant for resistant isolates, the inventors selected seven strong and conserved synergies, comprising antibiotics, human-targeted drugs or food additives, and assessed their efficacy against six MDR and XDR *E. coli* and *Klebsiella pneumoniae* clinical isolates. All these strains were recovered from infected patients, belonging to worldwide occurring successful clonal lineages harboring extended spectrum ß-lactamase (ESBL) resistance and various highly prevalent carbapenemases. One *K. pneumoniae* strain (929) is also resistant to the last-resort antibiotic, colistin. All drug pairs acted synergistically in most of the strains tested (FIG. 5a & FIG. 14). The inventors further tested two of these synergies, colistin-clarithromycin and spectinomycin-vanillin, with an established infection model for evaluating antibacterial activity, that of the greater wax moth, *Galleria mellonella*. Both combinations acted also synergistically in vivo by protecting *Galleria mellonella* from these MDR strains (FIG. 5b).

Figure 15:
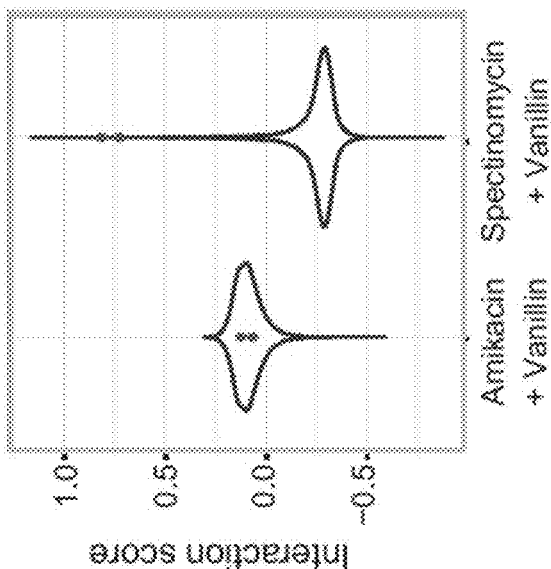
FIG. 15 shows the mode of Action for the vanillin-spectinomycin synergy. a) Spectinomycin MIC decreases upon addition of 100 μg/ml vanillin in the wildtype E. coli BW, as well as single-gene knockouts of members of the AcrAB-TolC efflux pump or its MarA regulator. Thus, the vanillin-spectinomycin synergy is independent of the effect of vanillin on AcrAB-TolC (FIG. 4). b) Synergy is specific to vanillin-spectinomycin, as 500 μg/ml of the vanillin-related compound, aspirin antagonizes spectinomycin, increasing the MIC~3-fold. c) Profiling the vanillin-spec-tinomycin combination in the E. coli BW Keio collection to deconvolute its MoA. Violin plots of the drug-drug interac-tion scores $\varepsilon$ of all mutants (n=9216) are presented for the vanillin-spectinomycin combination (synergy) and as con-trol, for the combination of vanillin with another aminogly-coside, amikacin (antagonism). The interaction scores of the two mdfA deletion clones present in the Keio library are indicated by red dots. The vanillin-spectinomycin synergy is lost in the absence of mdfA, whereas the vanillin-amikacin antagonism remains unaffected, indicating that the vanillin-spectinomycin synergy depends on MdfA. d) Deletion of mdfA leads to increased spectinomycin MIC and abolishes the synergy with vanillin, independent of the presence or absence of AcrAB-TolC. Mild overexpression of mdfA from a plasmid (pmdfA) further enhances the synergy with Van-illin, decreasing the spectinomycin MIC by ~2-fold (com-paring to MIC of combination in wildtype). Thus, MdfA levels are directly correlated to the degree of the spectino-mycin-vanillin synergy. c) Overexpression of mdfA leads to increased spectinomycin sensitivity, even though MIC does not change. The growth of E. coli BW and pmdfA was measured (OD595 nm after 8 h) over 2-fold serial dilutions of spectinomycin and normalized to the no-drug growth of the corresponding strain (white and black dots; average of n=3). Spectinomycin dose response was computed using a logistic fit of the averaged data points (note MICs are calculated by fitting individual replicates first and then averaging) Fitted curves are represented by full and dashed lines for pmdfA and E. coli BW respectively. f) Vanillin leads to accumulation of spectinomycin in the cell in an mdfA dependent manner. Intracellular spectinomycin is measured with a tritiated compound (n=4). For all MIC bar plots, error bars depict standard deviation and n=3-10.
Figure 15:
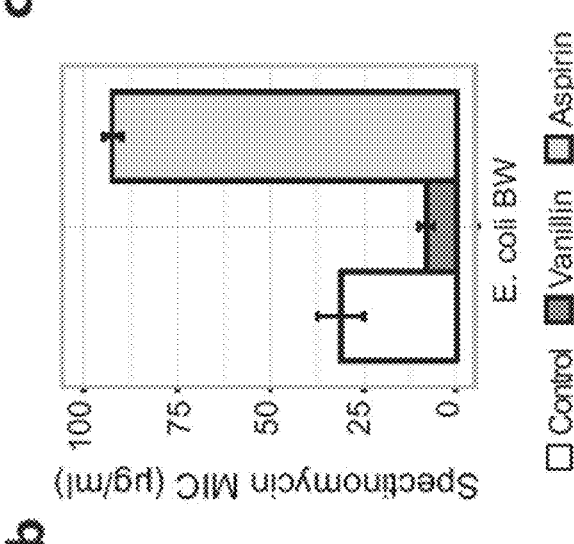
Figure 15:
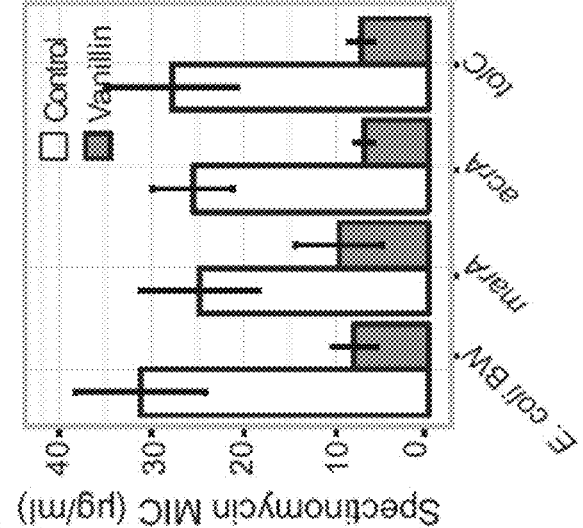
Figure 15:
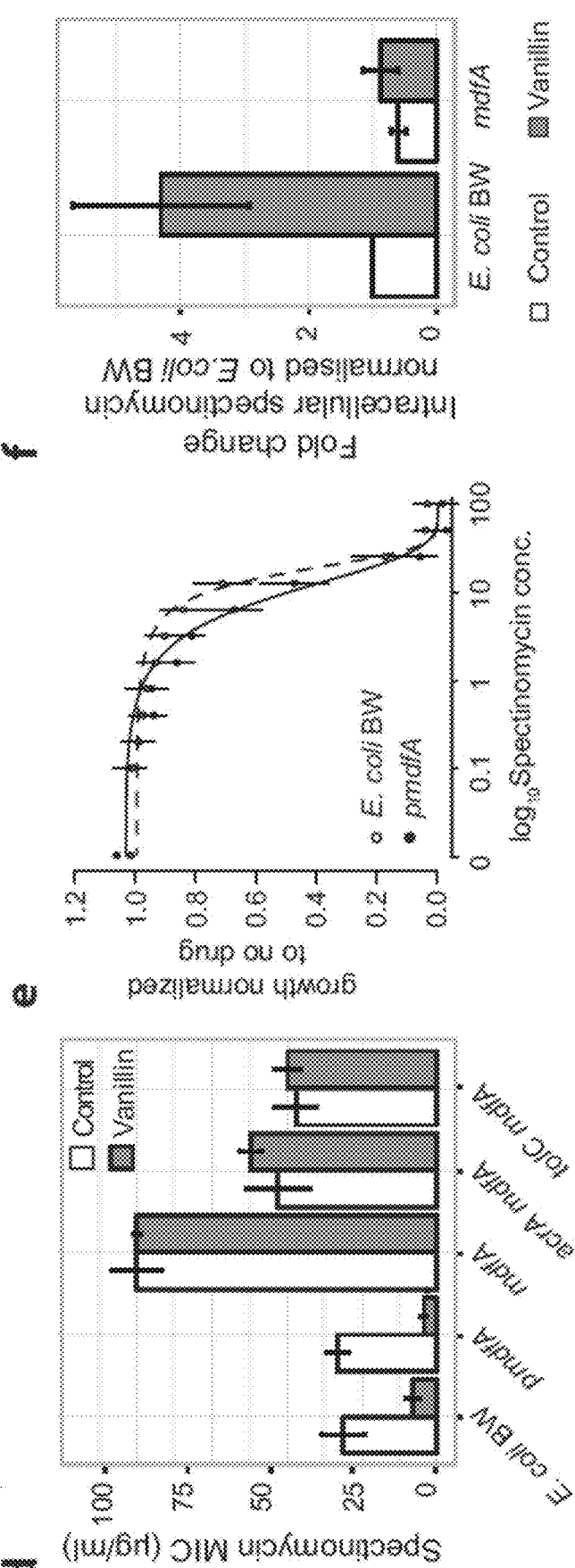

The strongest of these synergies is between colistin and different macrolides (FIG. 5 & FIG. 15). Although other polymyxins are known to help macrolides cross the OM of Gram negative bacteria, this particular synergy occurred at low colistin concentration (<0.3 g/ml) and was active even for the colistin-resistant strain (FIG. 5, *K. pneumoniae* 929), implying that macrolides also potentiate colistin's action via a yet unknown mechanism and that macrolides may resensitize colistin-resistant pathogens to colistin. In addition to antibiotic pairs, combinations of human-targeted drugs or food additives with antibiotics were also effective against MDR isolates. For example, procaine, a local anesthetic, resensitized *E. coli* and *K. pneumoniae* MDR isolates to fusidic acid and doxycycline (FIG. 14), although it did not inhibit bacterial growth on its own in the inventor's screen.

Loperamide potentiated both doxycycline and colistin. As with the combination of macrolides with colistin, it is currently unclear how drugs that inhibit the ribosome or the PMF 7 could potentiate the activity of colistin, which primarily acts on the OM. Furthermore, procaine, a local anesthetic, re-sensitized *E. coli* and *K. pneumoniae* MDR isolates to fusidic acid and doxycycline, although it could not inhibit bacterial growth on its own in the inventors' screen. Finally, the commonly used food additive vanillin potentiated the activity of spectinomycin in *E. coli* MDR isolates. This narrow-spectrum strong interaction opens the door for reusing an almost neglected antibiotic. Low amounts of vanillin (65 µg/ml) sensitized the largely resistant *E. coli* to spectinomycin, bringing the MIC from >30 to ~15 µg/ml. This synergy underlines the importance of exploring the role of food additives in antibacterial therapies.

The strong potentiation of the activity of spectinomycin in *E. coli* MDR isolates by Vanillin was intriguing, since vanillin antagonizes many other drugs, including other aminoglycosides. The inventors confirmed that this interaction is specific to spectinomycin and vanillin, and not to other aminoglycosides or aspirin, and thus also independent of the vanillin effect on AcrAB-TolC (FIG. 15*a-c*). The inventors then probed a genome-wide *E. coli* gene knockout library to identify mutants that abrogate the vanillin-spectinomycin interaction, but do not influence the amikacin (another aminoglycoside)-vanillin interaction. One of the top hits was mdfA, which encodes for a Major Facilitator Superfamily (MFS) transporter, exporting both electrogenic and electroneutral compounds (FIG. 15*c*). Consistent with MdfA being involved in spectinomycin uptake, ΔmdfA cells were more resistant to spectinomycin and not responsive to vanillin (FIG. 15*d*), whereas cells overexpressing mdfA were more sensitive to spectinomycin (FIG. 15*e*, not visible at the MIC level in FIG. 15*d*), as previously reported, with vanillin further exacerbating this effect (FIG. 15*d*). Vanillin addition also increased the intracellular spectinomycin concentration in an mdfA-dependent manner (FIG. 15*e*). At this point, it is unclear how MdfA, which is known to export compounds out of the cell, facilitates spectinomycin import in the cell. However, the presence/absence of mdfA is concordant with the species-specificity of this interaction, as the inventors detected the synergy in *E. coli* and *S. typhimurium* in the inventor's screen and subsequently in MDR *E. coli* isolates, but not in the phylogenetically more distant *P. aeruginosa* and *K. pneumoniae* isolates, which lack mdfA (FIG. 5*a*). Moreover, this narrow-spectrum strong interaction opens the door for reusing an almost neglected antibiotic. Low amounts of vanillin (65 µg/ml) sensitized the largely resistant *E. coli* to spectinomycin, bringing the MIC from >30 to ~15 µg/ml, which is similar to MICs of spectinomycin in Neisseria gonorrhoeae, against which spectinomycin is still clinically used. This synergy underlines the importance of exploring the role of food additives in combinatorial therapies, especially since several have mild antibacterial activities.

TABLE 1

Drug-drug interactions detected in the screen.

| Drug combination | | Interaction sign | | | | | |
|---|---|---|---|---|---|---|---|
| | | *E. coli* | *E. coli* | ST | | | |
| Drug 1 | Drug 2 | BW25113 | iAi1 | LT2 | S114028 | PAO1 | PA14 |
| Bacitracin | Colistin | Syn | Syn | Syn | Syn | Syn | Syn |
| Rifampicin | CHIR-90 | NA | Syn | Syn | Syn | NA | NA |
| Benzalkonium | Colistin | Syn | Syn | Syn | Syn | Syn | Syn |
| Rifampicin | Colistin | Syn | Syn | Syn | Syn | Syn | Syn |
| Pseudomonic acid | Colistin | Syn | Syn | Syn | Syn | NA | NA |
| Fusidic acid | Colistin | Syn | Syn | Syn | Syn | NA | Syn |
| Polymyxin B | Benzalkonium | Syn | Syn | Syn | Syn | Syn | Syn |
| Loperamide | Colistin | Syn | Syn | NA | Syn | Syn | Syn |
| Novobiocin | Colistin | Syn | Syn | Syn | Syn | NA | Syn |
| Cefaclor | Meropenem | NA | NA | NA | Syn | NA | NA |
| Clarithromycin | Colistin | Syn | Syn | Syn | Syn | Syn | Syn |
| Minocycline | Chlorhexidine | NA | NA | Syn | Syn | Syn | Syn |
| Chlorhexidine | Rifampicin | NA | NA | Syn | Syn | NA | NA |
| Erythromycin | Colistin | Syn | Syn | Syn | Syn | NA | Syn |
| Chlorhexidine | Pseudomonic acid | NA | NA | NA | Syn | NA | NA |
| Fusidic acid | Metformin | NA | NA | Syn | Syn | NA | NA |
| Mecillinam | Meropenem | NA | NA | NA | Syn | NA | NA |
| Chlorhexidine | Clarithromycin | NA | NA | NA | Syn | NA | NA |
| Fusidic acid | CHIR-90 | Syn | Syn | Syn | Syn | NA | NA |
| Polymyxin B | Rifampicin | NA | Syn | Syn | Syn | Syn | Syn |
| Levofloxacin | Chlorhexidine | NA | NA | Syn | Syn | Syn | NA |
| Cycloserine D | Mecillinam | NA | NA | Syn | Syn | NA | NA |
| PMS | Meropenem | NA | NA | Syn | Syn | NA | NA |
| Pyocyanin | Meropenem | NA | NA | Syn | Syn | NA | NA |
| CCCP | Colistin | Syn | NA | Syn | NA | NA | NA |
| Rifampicin | Streptozotocin | NA | NA | Syn | Syn | NA | NA |
| Cefaclor | Mecillinam | Syn | Syn | Syn | Syn | NA | NA |
| Amoxicillin | Piperacillin | Syn | Syn | Syn | Syn | Anta | NA |
| Amoxicillin | Aztreonam | Syn | Syn | Syn | Syn | NA | NA |
| Bacitracin | CHIR-90 | Syn | Syn | Syn | Syn | NA | NA |
| Novobiocin | Chlorhexidine | NA | NA | Syn | Syn | Syn | Syn |
| Nitrofurantoin | Phleomycin | Syn | Syn | Syn | Syn | NA | NA |
| Cefaclor | Aztreonam | Syn | Syn | Syn | Syn | NA | NA |
| Chlorhexidine | Cerulenin | NA | NA | NA | Syn | Syn | NA |
| Piperacillin | Mecillinam | NA | NA | Syn | Syn | NA | NA |
| Mecillinam | Aztreonam | NA | NA | Syn | Syn | NA | NA |
| Doxycycline | Metformin | NA | NA | Syn | Syn | NA | Syn |

TABLE 1-continued

| Drug-drug interactions detected in the screen. | | | | | | | |
|---|---|---|---|---|---|---|---|
| Penicillin G | Meropenem | NA | NA | NA | Syn | NA | NA |
| Verapamil | Colistin | Syn | Syn | Syn | Syn | Syn | Syn |
| Doxycycline | Benzalkonium | NA | NA | Syn | Syn | NA | NA |
| Spectinomycin | Vanillin | Syn | Syn | Syn | Syn | NA | NA |
| Bleomycin | CHIR-90 | NA | Syn | NA | Syn | NA | NA |
| Bacitracin | Polymyxin B | NA | NA | NA | Syn | Syn | Syn |
| Verapamil | CHIR-90 | Syn | Syn | NA | Syn | NA | NA |
| Bleomycin | Colistin | Syn | Syn | NA | Syn | NA | NA |
| Pyocyanin | Imipenem | NA | NA | Syn | Syn | NA | NA |
| Cerulenin | Colistin | Syn | NA | Syn | Syn | NA | NA |
| Chlorhexidine | Pyocyanin | NA | NA | Syn | Syn | NA | NA |
| Polymyxin B | Fusidic acid | Syn | Syn | Syn | NA | NA | NA |
| Doxycycline | CHIR-90 | NA | Syn | Syn | Syn | NA | NA |
| Cefaclor | Penicillin G | NA | NA | Syn | Syn | Syn | NA |
| Clarithromycin | CHIR-90 | Syn | Syn | NA | Syn | NA | NA |
| Piperacillin | Tobramycin | NA | NA | Syn | Syn | Syn | Syn |
| Novobiocin | Polymyxin B | Syn | Syn | Syn | Syn | NA | NA |
| Procaine | Azithromycin | Syn | Syn | Syn | Syn | NA | NA |
| Doxycycline | Procaine | NA | NA | Syn | NA | Syn | Syn |
| Procaine | Phleomycin | Syn | Syn | NA | Syn | NA | NA |
| Procaine | Piperacillin | NA | NA | Syn | Syn | NA | NA |
| Procaine | Moxifloxacin | NA | NA | Syn | NA | NA | NA |
| Novobiocin | Bacitracin | Syn | Syn | NA | Syn | NA | NA |
| Pyocyanin | Acetylsalisylic acid | Syn | NA | Syn | NA | NA | NA |
| Bleomycin | Streptozotocin | Syn | NA | Syn | Syn | NA | NA |
| Procaine | Pyocyanin | Syn | NA | Syn | Syn | NA | NA |
| Tobramycin | Aztreonam | NA | NA | NA | Syn | Syn | Syn |
| PMS | Streptozotocin | NA | NA | Syn | Syn | NA | NA |
| Benzalkonium | EGCG | NA | Anta | NA | Syn | NA | Anta |
| Amikacin | Aztreonam | NA | NA | Syn | Syn | Syn | Syn |
| Paraquat | Streptozotocin | NA | NA | Syn | Syn | NA | NA |
| PMS | Acetylsalisylic acid | Syn | NA | Syn | NA | NA | NA |
| Trimethoprim | Sulfamonomethoxine | Syn | Syn | Syn | Syn | NA | NA |
| Amikacin | PMS | Anta | NA | Anta | Syn | NA | NA |
| Fosfomycin | Cefsulodin | Syn | Syn | Syn | NA | NA | NA |
| Fosfomycin | Vanillin | Syn | Syn | Syn | NA | NA | NA |
| Amikacin | Puromycin | Syn | Syn | Syn | NA | NA | NA |
| Fusidic acid | Azithromycin | NA | NA | Syn | NA | NA | NA |
| Nitrofurantoin | Streptozotocin | NA | NA | Syn | NA | NA | NA |
| Amikacin | Pyocyanin | Anta | NA | Anta | NA | NA | NA |
| Amikacin | Streptozotocin | NA | NA | Syn | NA | NA | NA |
| Doxycycline | Spectinomycin | NA | NA | Syn | NA | NA | NA |
| PMS | Rifampicin | Syn | NA | Syn | NA | NA | NA |
| Procaine | Rifampicin | Syn | Syn | Syn | NA | NA | NA |
| PMS | Pyocyanin | NA | NA | Syn | NA | NA | NA |
| Cycloserine D | Paraquat | NA | NA | Syn | NA | NA | NA |
| Pyocyanin | Gentamicin | Anta | NA | Anta | NA | NA | NA |
| Cycloserine D | Tobramycin | NA | NA | Anta | NA | NA | NA |
| Levofloxacin | Metformin | NA | NA | Syn | NA | Syn | NA |
| Rifampicin | Cerulenin | Syn | Anta | Syn | NA | NA | NA |
| Cefsulodin | Piperacillin | Syn | Syn | Anta | NA | NA | NA |
| PMS | Gentamicin | Anta | Anta | Anta | NA | NA | NA |
| Pyocyanin | Phleomycin | Anta | Anta | Anta | NA | NA | NA |
| Pyocyanin | Bleomycin | Anta | NA | Anta | NA | NA | NA |
| Amikacin | Procaine | Anta | NA | Anta | NA | Anta | Anta |
| Benzalkonium | Tobramycin | NA | NA | Anta | NA | NA | NA |
| Fosfomycin | Novobiocin | Anta | Anta | Syn | NA | Syn | NA |
| Penicillin G | Pyocyanin | NA | NA | Anta | NA | NA | NA |
| PMS | Bleomycin | Anta | Anta | Anta | NA | NA | NA |
| Novobiocin | Fusidic acid | NA | Syn | NA | Anta | NA | NA |
| Paraquat | Puromycin | NA | Anta | NA | Anta | NA | NA |
| PMS | Phleomycin | Anta | Anta | Anta | NA | NA | NA |
| Doxycycline | Fosfomycin | Anta | Anta | Anta | NA | NA | NA |
| Paraquat | Phleomycin | NA | NA | Anta | NA | NA | NA |
| Pyocyanin | Mitomycin C | Anta | Anta | Anta | NA | NA | NA |
| Aztreonam | Caffeine | Anta | NA | NA | Anta | NA | NA |
| Procaine | Gentamicin | Anta | NA | Anta | NA | NA | NA |
| Doxycycline | Vanillin | Anta | Anta | NA | Anta | NA | NA |
| PMS | Azithromycin | Anta | NA | NA | Anta | NA | NA |
| Ciprofloxacin | Doxycycline | NA | Anta | Anta | Anta | NA | Anta |
| Paraquat | Piperacillin | NA | NA | Anta | Anta | NA | Anta |
| Chloramphenicol | Ciprofloxacin | NA | NA | Anta | NA | NA | Anta |
| Ciprofloxacin | Benzalkonium | Anta | Anta | NA | Anta | NA | Anta |
| Ciprofloxacin | PMS | Anta | Anta | Anta | Anta | NA | NA |
| Mecillinam | Metformin | Anta | NA | NA | Anta | NA | NA |
| Doxycycline | Mecillinam | Anta | Anta | Anta | Anta | NA | NA |
| Mecillinam | Pyocyanin | Anta | NA | NA | Anta | NA | NA |
| Doxycycline | PMS | Anta | Anta | Anta | Anta | NA | NA |

TABLE 1-continued

| Drug-drug interactions detected in the screen. | | | | | | | |
|---|---|---|---|---|---|---|---|
| Doxycycline | Pyocyanin | Anta | Anta | Anta | Anta | NA | NA |
| Novobiocin | Paraquat | NA | Anta | NA | Anta | NA | NA |
| Novobiocin | Vanillin | NA | Anta | NA | Anta | NA | NA |
| Amikacin | Benzalkonium | Anta | NA | Anta | Anta | NA | NA |
| Vanillin | Moxifloxacin | Anta | Anta | NA | Anta | NA | NA |
| Ciprofloxacin | Pyocyanin | Anta | NA | Anta | Anta | NA | NA |
| PMS | CHIR-90 | Anta | Anta | Anta | NA | NA | NA |
| Novobiocin | PMS | Anta | Anta | NA | Anta | NA | NA |
| Benzalkonium | Gentamicin | NA | Anta | NA | Anta | NA | NA |
| Cerulenin | CHIR-90 | Anta | Anta | Anta | Anta | NA | NA |
| Paraquat | CHIR-90 | Anta | Anta | Anta | Anta | NA | NA |
| Pyocyanin | CHIR-90 | Anta | NA | Anta | Anta | NA | NA |
| Nitrofurantoin | Aztreonam | NA | NA | NA | Anta | NA | NA |
| Procaine | Aztreonam | Anta | Anta | Anta | Anta | NA | NA |
| Paraquat | Moxifloxacin | NA | Anta | NA | Anta | NA | NA |
| EGCG | Moxifloxacin | Anta | Anta | NA | Anta | NA | NA |
| Paraquat | Levofloxacin | NA | NA | Anta | Anta | NA | NA |
| PMS | Aztreonam | Anta | NA | Anta | Anta | NA | NA |
| Cefaclor | Metformin | NA | NA | NA | Anta | NA | NA |
| Cefaclor | Colistin | NA | NA | Anta | Anta | NA | NA |
| Levofloxacin | Acetylsalisylic acid | Anta | Anta | Anta | NA | NA | NA |
| PMS | Levofloxacin | Anta | NA | Anta | Anta | NA | NA |
| Aztreonam | Acetylsalisylic acid | Anta | Anta | Anta | Anta | NA | NA |
| Levofloxacin | Pyocyanin | Anta | Anta | Anta | Anta | NA | NA |
| PMS | Moxifloxacin | Anta | Anta | Anta | Anta | NA | NA |
| Ciprofloxacin | Paraquat | Anta | Anta | Anta | Anta | NA | NA |
| Paraquat | Aztreonam | NA | NA | Anta | Anta | Anta | NA |
| Ciprofloxacin | Vanillin | Anta | Anta | Anta | Anta | NA | NA |
| Vanillin | Aztreonam | Anta | Anta | Anta | Anta | NA | Anta |
| Aztreonam | Pyocyanin | Anta | Anta | Anta | Anta | NA | NA |
| Pyocyanin | Moxifloxacin | Anta | Anta | Anta | Anta | NA | NA |
| Oxacillin | Cefaclor | Syn | Syn | NA | NA | NA | NA |
| Nitrofurantoin | Tobramycin | Syn | NA | NA | NA | Anta | NA |
| Polymyxin B | Curcumin | Syn | NA | NA | NA | NA | NA |
| Procaine | Puromycin | Syn | Syn | NA | NA | NA | NA |
| Spiramycin | Colistin | Syn | Syn | NA | NA | NA | NA |
| Procaine | Bleomycin | Syn | Syn | NA | NA | NA | NA |
| Chloramphenicol | Nitrofurantoin | NA | Syn | NA | NA | NA | Anta |
| Benzalkonium | Procaine | Syn | Syn | NA | NA | NA | Syn |
| Cefsulodin | Aztreonam | Syn | Syn | NA | NA | NA | Syn |
| Polymyxin B | Triclosan | Syn | NA | NA | NA | NA | NA |
| Amikacin | Clindamycin | Anta | NA | NA | NA | NA | NA |
| Erythromycin | Tobramycin | Anta | NA | NA | NA | Anta | Anta |
| Tobramycin | Metformin | Anta | NA | NA | NA | NA | NA |
| A22 | Colistin | Anta | NA | NA | NA | NA | Syn |
| Clindamycin | Tobramycin | Anta | NA | NA | NA | NA | NA |
| Polymyxin B | Cefaclor | Anta | NA | NA | NA | NA | NA |
| Fosfomycin | Mitomycin C | Anta | Anta | NA | NA | Syn | Anta |
| Fosfomycin | Erythromycin | Anta | Anta | NA | NA | Syn | NA |
| Rifampicin | Gentamicin | Anta | NA | NA | NA | NA | NA |
| Rifampicin | Phleomycin | Anta | NA | NA | NA | Anta | NA |
| Fosfomycin | Clarithromycin | Anta | Anta | NA | NA | Syn | Syn |
| Spectinomycin | Fosfomycin | Anta | Anta | NA | NA | NA | NA |
| Fosfomycin | Trimethoprim | Anta | Anta | NA | NA | NA | NA |
| Vanillin | CHIR-90 | Anta | Anta | NA | NA | NA | NA |
| A22 | Acetylsalisylic acid | Anta | Anta | NA | NA | NA | NA |
| Ciprofloxacin | Caffeine | Anta | Anta | NA | NA | NA | NA |
| Aztreonam | Berberine | Anta | Anta | NA | NA | NA | NA |
| Amoxicillin | Vanillin | Anta | Anta | NA | NA | NA | NA |
| Aztreonam | Curcumin | Anta | Anta | NA | NA | NA | NA |
| Benzalkonium | Curcumin | NA | Anta | NA | NA | Anta | Anta |
| Polymyxin B | Chlorhexidine | NA | NA | NA | NA | Syn | Syn |
| Cefotaxime | Metformin | NA | NA | NA | NA | Syn | Syn |
| Procaine | Levofloxacin | NA | NA | NA | NA | Syn | NA |
| Procaine | Minocycline | NA | NA | NA | NA | Syn | NA |
| Loperamide | Clarithromycin | NA | NA | NA | NA | Syn | NA |
| Amoxicillin | Gentamicin | NA | NA | NA | NA | Syn | NA |
| Ciprofloxacin | Metformin | NA | NA | NA | NA | Syn | NA |
| Bacitracin | Gentamicin | NA | NA | NA | NA | Syn | NA |
| Cefotaxime | Tobramycin | NA | NA | NA | NA | Syn | NA |
| Cefotaxime | Gentamicin | NA | NA | NA | NA | Syn | NA |
| Loperamide | Gentamicin | NA | NA | NA | NA | Syn | Syn |
| Minocycline | Colistin | NA | NA | NA | NA | Syn | Syn |
| Chlorhexidine | Colistin | NA | NA | NA | NA | Syn | Syn |
| Chlorhexidine | Moxifloxacin | NA | NA | NA | NA | Syn | Syn |
| Aztreonam | Clarithromycin | NA | NA | NA | NA | Syn | NA |
| Ciprofloxacin | Berberine | NA | NA | NA | NA | Anta | Anta |
| Amikacin | Acetylsalisylic acid | NA | NA | NA | NA | Anta | NA |

TABLE 1-continued

| Drug-drug interactions detected in the screen. | | | | | | | |
|---|---|---|---|---|---|---|---|
| Amikacin | Phleomycin | NA | NA | NA | NA | Anta | NA |
| Benzalkonium | Azithromycin | NA | NA | NA | NA | Anta | Anta |
| Cefsulodin | Loperamide | NA | NA | NA | NA | Anta | Anta |
| Levofloxacin | Berberine | NA | NA | NA | NA | Anta | Anta |
| Piperacillin | Imipenem | NA | NA | NA | NA | Anta | NA |
| Nitrofurantoin | Gentamicin | NA | NA | NA | NA | Anta | NA |
| Minocycline | Gentamicin | NA | NA | NA | NA | Anta | NA |
| Tobramycin | Clarithromycin | NA | NA | NA | NA | Anta | Anta |
| Tobramycin | Azithromycin | NA | NA | NA | NA | Anta | NA |
| Tobramycin | Acetylsalisylic acid | NA | NA | NA | NA | Anta | Anta |
| EGCG | Colistin | NA | NA | NA | NA | Anta | NA |
| Chloramphenicol | Cefsulodin | NA | NA | NA | NA | Anta | NA |
| Cefsulodin | Cephalexin | NA | NA | NA | NA | Anta | NA |
| Cefsulodin | Linezolid | NA | NA | NA | NA | Anta | Anta |
| Procaine | Chlorhexidine | NA | NA | NA | NA | NA | Syn |
| Piperacillin | Metformin | NA | NA | NA | NA | NA | Syn |
| Chloramphenicol | Tobramycin | NA | NA | NA | NA | NA | Anta |
| Doxycycline | Gentamicin | NA | NA | NA | NA | NA | Anta |
| Benzalkonium | Levofloxacin | NA | NA | NA | NA | NA | Anta |
| Flucytosine | Mitomycin C | NA | NA | NA | NA | Syn | Syn |
| Colistin | Phenformin | NA | NA | NA | NA | Syn | Syn |
| Piperacillin | Flucytosine | NA | NA | NA | NA | Anta | Anta |
| Tobramycin | Flucytosine | NA | NA | NA | NA | Anta | Anta |
| Aztreonam | Imipenem | NA | NA | NA | NA | Anta | Syn |
| Colistin | Gentamicin | NA | NA | NA | NA | Anta | NA |

| Drug combination | | Interaction score | | | | | |
|---|---|---|---|---|---|---|---|
| | | *E. coli* | *E. coli* | ST | ST | | |
| Drug 1 | Drug 2 | BW25113 | iAi1 | LT2 | 14028 | PAO1 | PA14 |
| Bacitracin | Colistin | −0.97 | −0.89 | −0.92 | −0.92 | −0.82 | −0.84 |
| Rifampicin | CHIR-90 | −0.35 | −0.55 | −0.73 | −0.92 | NA | NA |
| Benzalkonium | Colistin | −0.89 | −0.86 | −0.91 | −0.92 | −0.85 | −0.79 |
| Rifampicin | Colistin | −0.85 | −0.74 | −0.99 | −0.91 | −0.54 | −0.39 |
| Pseudomonic acid | Colistin | −0.79 | −0.70 | −0.75 | −0.90 | NA | NA |
| Fusidic acid | Colistin | −0.82 | −0.79 | −0.93 | −0.90 | 0.05 | −0.13 |
| Polymyxin B | Benzalkonium | −0.82 | −0.82 | −0.88 | −0.88 | −0.50 | −0.48 |
| Loperamide | Colistin | −0.89 | −0.87 | −0.20 | −0.84 | −0.70 | −0.77 |
| Novobiocin | Colistin | −0.77 | −0.72 | −0.92 | −0.83 | −0.05 | −0.14 |
| Cefaclor | Meropenem | NA | NA | −0.15 | −0.77 | NA | NA |
| Clarithromycin | Colistin | −0.78 | −0.80 | −0.78 | −0.73 | −0.37 | −0.31 |
| Minocycline | Chlorhexidine | NA | NA | −0.79 | −0.72 | −0.44 | −0.58 |
| Chlorhexidine | Rifampicin | NA | NA | −0.84 | −0.72 | NA | NA |
| Erythromycin | Colistin | −0.69 | −0.73 | −0.67 | −0.65 | 0.01 | −0.18 |
| Chlorhexidine | Pseudomonic acid | NA | NA | −0.29 | −0.64 | NA | NA |
| Fusidic acid | Metformin | NA | NA | −0.73 | −0.64 | NA | NA |
| Mecillinam | Meropenem | NA | NA | −0.16 | −0.62 | NA | NA |
| Chlorhexidine | Clarithromycin | NA | NA | −0.49 | −0.61 | NA | NA |
| Fusidic acid | CHIR-90 | −0.48 | −0.61 | −0.83 | −0.57 | NA | NA |
| Polymyxin B | Rifampicin | −0.24 | −0.28 | −0.52 | −0.57 | −0.20 | −0.12 |
| Levofloxacin | Chlorhexidine | NA | NA | −0.63 | −0.57 | −0.44 | <0.005 |
| Cycloserine D | Mecillinam | NA | NA | −0.67 | −0.57 | NA | NA |
| PMS | Meropenem | NA | NA | −0.76 | −0.55 | NA | NA |
| Pyocyanin | Meropenem | NA | NA | −0.74 | −0.55 | NA | NA |
| CCCP | Colistin | −0.52 | −0.41 | −0.80 | −0.53 | NA | NA |
| Rifampicin | Streptozotocin | NA | NA | −0.53 | −0.52 | NA | NA |
| Cefaclor | Mecillinam | −0.20 | −0.37 | −0.61 | −0.51 | NA | NA |
| Amoxicillin | Piperacillin | −0.19 | −0.29 | −0.59 | −0.47 | 0.31 | 0.08 |
| Amoxicillin | Aztreonam | −0.52 | −0.29 | −0.54 | −0.47 | NA | NA |
| Bacitracin | CHIR-90 | −0.55 | −0.24 | −0.82 | −0.47 | NA | NA |
| Novobiocin | Chlorhexidine | NA | NA | −0.18 | −0.47 | −0.28 | −0.64 |
| Nitrofurantoin | Phleomycin | −0.37 | −0.27 | −0.33 | −0.46 | NA | NA |
| Cefaclor | Aztreonam | −0.60 | −0.54 | −0.58 | −0.46 | NA | NA |
| Chlorhexidine | Cerulenin | NA | NA | −0.81 | −0.46 | −0.17 | −0.28 |
| Piperacillin | Mecillinam | NA | NA | −0.63 | −0.45 | NA | NA |
| Mecillinam | Aztreonam | NA | NA | −0.56 | −0.43 | NA | NA |
| Doxycycline | Metformin | NA | NA | −0.70 | −0.43 | −0.07 | −0.39 |
| Penicillin G | Meropenem | NA | NA | −0.27 | −0.41 | NA | NA |
| Verapamil | Colistin | −0.90 | −0.91 | −0.90 | −0.41 | −0.66 | −0.62 |
| Doxycycline | Benzalkonium | NA | NA | −0.54 | −0.41 | NA | NA |
| Spectinomycin | Vanillin | −0.89 | −0.54 | −0.56 | −0.41 | NA | NA |
| Bleomycin | CHIR-90 | −0.20 | −0.40 | −0.58 | −0.40 | NA | NA |
| Bacitracin | Polymyxin B | NA | NA | −0.07 | −0.39 | −0.28 | −0.35 |
| Verapamil | CHIR-90 | −0.52 | −0.34 | −0.20 | −0.39 | NA | NA |
| Bleomycin | Colistin | −0.63 | −0.48 | −0.23 | −0.38 | NA | NA |
| Pyocyanin | Imipenem | NA | NA | −0.50 | −0.37 | NA | NA |

TABLE 1-continued

| | Drug-drug interactions detected in the screen. | | | | | | |
|---|---|---|---|---|---|---|---|
| Cerulenin | Colistin | −0.57 | −0.07 | −0.25 | −0.37 | NA | NA |
| Chlorhexidine | Pyocyanin | NA | NA | −0.60 | −0.36 | NA | NA |
| Polymyxin B | Fusidic acid | −0.85 | −0.42 | −0.32 | −0.35 | NA | NA |
| Doxycycline | CHIR-90 | −0.28 | −0.36 | −0.78 | −0.34 | NA | NA |
| Cefaclor | Penicillin G | NA | NA | −0.18 | −0.33 | −0.11 | −0.04 |
| Clarithromycin | CHIR-90 | −0.44 | −0.32 | −0.17 | −0.32 | NA | NA |
| Piperacillin | Tobramycin | NA | NA | −0.58 | −0.29 | −0.48 | −0.13 |
| Novobiocin | Polymyxin B | −0.29 | −0.36 | −0.18 | −0.28 | NA | NA |
| Procaine | Azithromycin | −0.34 | −0.43 | −0.31 | −0.27 | NA | NA |
| Doxycycline | Procaine | NA | NA | −0.43 | −0.26 | −0.22 | −0.29 |
| Procaine | Phleomycin | −0.35 | −0.40 | −0.15 | −0.25 | NA | NA |
| Procaine | Piperacillin | NA | NA | −0.47 | −0.25 | NA | NA |
| Procaine | Moxifloxacin | NA | NA | −0.42 | −0.24 | NA | NA |
| Novobiocin | Bacitracin | −0.38 | −0.28 | −0.06 | −0.23 | NA | NA |
| Pyocyanin | Acetylsalisylic acid | −0.38 | −0.15 | −0.26 | −0.18 | NA | NA |
| Bleomycin | Streptozotocin | −0.24 | −0.06 | −0.46 | −0.18 | NA | NA |
| Procaine | Pyocyanin | −0.35 | 0.07 | −0.15 | −0.16 | NA | NA |
| Tobramycin | Aztreonam | NA | NA | −0.45 | −0.16 | −0.44 | −0.40 |
| PMS | Streptozotocin | NA | NA | −0.39 | −0.16 | NA | NA |
| Benzalkonium | EGCG | −0.25 | 0.83 | −0.10 | −0.15 | 0.11 | 0.44 |
| Amikacin | Aztreonam | NA | NA | −0.31 | −0.14 | −0.32 | −0.50 |
| Paraquat | Streptozotocin | NA | NA | −0.50 | −0.14 | NA | NA |
| PMS | Acetylsalisylic acid | −0.40 | −0.07 | −0.20 | −0.12 | NA | NA |
| Trimethoprim | Sulfamonomethoxine | −0.50 | −0.34 | −0.18 | −0.12 | NA | NA |
| Amikacin | PMS | 0.49 | 0.05 | 0.32 | −0.11 | NA | NA |
| Fosfomycin | Cefsulodin | −0.35 | −0.21 | −0.22 | −0.10 | NA | NA |
| Fosfomycin | Vanillin | −0.41 | −0.33 | −0.13 | −0.10 | NA | NA |
| Amikacin | Puromycin | −0.42 | −0.26 | −0.29 | −0.10 | NA | NA |
| Fusidic acid | Azithromycin | NA | NA | −0.32 | −0.10 | NA | NA |
| Nitrofurantoin | Streptozotocin | NA | NA | −0.48 | −0.09 | NA | NA |
| Amikacin | Pyocyanin | 0.33 | −0.05 | 0.24 | −0.09 | NA | NA |
| Amikacin | Streptozotocin | NA | NA | −0.48 | −0.09 | NA | NA |
| Doxycycline | Spectinomycin | NA | NA | −0.39 | −0.09 | NA | NA |
| PMS | Rifampicin | −0.38 | 0.09 | −0.23 | −0.08 | NA | NA |
| Procaine | Rifampicin | −0.44 | −0.42 | −0.12 | −0.07 | NA | NA |
| PMS | Pyocyanin | NA | NA | −0.66 | −0.07 | NA | NA |
| Cycloserine D | Paraquat | NA | NA | −0.42 | −0.05 | NA | NA |
| Pyocyanin | Gentamicin | 0.46 | 0.09 | 0.51 | −0.05 | NA | NA |
| Cycloserine D | Tobramycin | NA | NA | 0.78 | −0.04 | NA | NA |
| Levofloxacin | Metformin | NA | NA | −0.47 | <0.005 | −0.32 | 0.07 |
| Rifampicin | Cerulenin | −0.46 | 0.24 | −0.18 | 0.03 | NA | NA |
| Cefsulodin | Piperacillin | −0.31 | −0.45 | 0.16 | 0.04 | NA | NA |
| PMS | Gentamicin | 0.44 | 0.22 | 0.40 | 0.05 | NA | NA |
| Pyocyanin | Phleomycin | 0.47 | 0.28 | 0.46 | 0.05 | NA | NA |
| Pyocyanin | Bleomycin | 0.27 | 0.16 | 0.13 | 0.07 | NA | NA |
| Amikacin | Procaine | 0.47 | 0.06 | 0.20 | 0.08 | 0.19 | 0.11 |
| Benzalkonium | Tobramycin | NA | NA | 0.81 | 0.08 | NA | NA |
| Fosfomycin | Novobiocin | 0.31 | 0.21 | −0.13 | 0.08 | −0.15 | −0.06 |
| Penicillin G | Pyocyanin | NA | NA | 0.24 | 0.10 | NA | NA |
| PMS | Bleomycin | 0.36 | 0.20 | 0.14 | 0.10 | NA | NA |
| Novobiocin | Fusidic acid | −0.32 | −0.22 | −0.03 | 0.10 | NA | NA |
| Paraquat | Puromycin | 0.04 | 0.56 | 0.05 | 0.10 | NA | NA |
| PMS | Phleomycin | 0.33 | 0.24 | 0.56 | 0.10 | NA | NA |
| Doxycycline | Fosfomycin | 0.48 | 0.49 | 0.10 | 0.11 | NA | NA |
| Paraquat | Phleomycin | NA | NA | 0.41 | 0.11 | NA | NA |
| Pyocyanin | Mitomycin C | 0.12 | 0.28 | 0.44 | 0.11 | NA | NA |
| Aztreonam | Caffeine | 0.42 | 0.07 | 0.14 | 0.15 | NA | NA |
| Procaine | Gentamicin | 0.56 | 0.18 | 0.68 | 0.16 | NA | NA |
| Doxycycline | Vanillin | 0.21 | 0.44 | 0.06 | 0.16 | NA | NA |
| PMS | Azithromycin | 0.22 | 0.12 | 0.09 | 0.19 | NA | NA |
| Ciprofloxacin | Doxycycline | 0.21 | 0.33 | 0.23 | 0.21 | 0.04 | 0.38 |
| Paraquat | Piperacillin | NA | NA | 0.25 | 0.21 | 0.16 | 0.46 |
| Chloramphenicol | Ciprofloxacin | NA | NA | 0.23 | 0.23 | 0.14 | 0.14 |
| Ciprofloxacin | Benzalkonium | 0.20 | 0.20 | 0.07 | 0.23 | 0.07 | 0.43 |
| Ciprofloxacin | PMS | 0.54 | 0.22 | 0.41 | 0.24 | NA | NA |
| Mecillinam | Metformin | 0.41 | 0.14 | 0.67 | 0.25 | NA | NA |
| Doxycycline | Mecillinam | 0.23 | 0.33 | 0.43 | 0.26 | NA | NA |
| Mecillinam | Pyocyanin | 0.29 | 0.10 | −0.03 | 0.26 | NA | NA |
| Doxycycline | PMS | 0.25 | 0.29 | 0.15 | 0.26 | NA | NA |
| Doxycycline | Pyocyanin | 0.28 | 0.21 | 0.17 | 0.26 | NA | NA |
| Novobiocin | Paraquat | 0.10 | 0.69 | −0.05 | 0.27 | NA | NA |
| Novobiocin | Vanillin | 0.08 | 0.69 | 0.05 | 0.29 | NA | NA |
| Amikacin | Benzalkonium | 0.40 | 0.08 | 0.29 | 0.29 | NA | NA |
| Vanillin | Moxifloxacin | 0.37 | 0.25 | 0.04 | 0.32 | NA | NA |
| Ciprofloxacin | Pyocyanin | 0.46 | 0.22 | 0.40 | 0.34 | NA | NA |
| PMS | CHIR-90 | 0.79 | 0.39 | 0.94 | 0.34 | NA | NA |
| Novobiocin | PMS | 0.20 | 0.42 | −0.05 | 0.36 | NA | NA |
| Benzalkonium | Gentamicin | 0.36 | 0.32 | 0.22 | 0.38 | NA | NA |

TABLE 1-continued

| Drug-drug interactions detected in the screen. | | | | | | | |
|---|---|---|---|---|---|---|---|
| Cerulenin | CHIR-90 | 0.89 | 0.75 | 1.00 | 0.50 | NA | NA |
| Paraquat | CHIR-90 | 0.49 | 0.61 | 0.84 | 0.51 | NA | NA |
| Pyocyanin | CHIR-90 | 0.51 | 0.24 | 0.97 | 0.55 | NA | NA |
| Nitrofurantoin | Aztreonam | NA | NA | 0.08 | 0.57 | NA | NA |
| Procaine | Aztreonam | 0.45 | 0.31 | 0.42 | 0.57 | NA | NA |
| Paraquat | Moxifloxacin | 0.42 | 0.47 | 0.20 | 0.60 | NA | NA |
| EGCG | Moxifloxacin | 0.35 | 0.24 | 0.04 | 0.60 | NA | NA |
| Paraquat | Levofloxacin | NA | NA | 0.69 | 0.62 | NA | NA |
| PMS | Aztreonam | 0.37 | 0.10 | 0.44 | 0.64 | NA | NA |
| Cefaclor | Metformin | NA | NA | 0.46 | 0.65 | NA | NA |
| Cefaclor | Colistin | NA | NA | 0.83 | 0.65 | NA | NA |
| Levofloxacin | Acetylsalisylic acid | 0.61 | 0.47 | 0.55 | 0.67 | NA | NA |
| PMS | Levofloxacin | 0.54 | 0.18 | 0.72 | 0.69 | NA | NA |
| Aztreonam | Acetylsalisylic acid | 0.64 | 0.68 | 0.55 | 0.70 | NA | NA |
| Levofloxacin | Pyocyanin | 0.56 | 0.28 | 0.72 | 0.70 | NA | NA |
| PMS | Moxifloxacin | 0.71 | 0.41 | 0.26 | 0.72 | NA | NA |
| Ciprofloxacin | Paraquat | 0.40 | 0.26 | 0.30 | 0.73 | NA | NA |
| Paraquat | Aztreonam | NA | NA | 0.45 | 0.74 | 0.18 | 0.11 |
| Ciprofloxacin | Vanillin | 0.47 | 0.68 | 0.32 | 0.76 | NA | NA |
| Vanillin | Aztreonam | 0.39 | 0.47 | 0.65 | 0.79 | 0.07 | 0.15 |
| Aztreonam | Pyocyanin | 0.33 | 0.18 | 0.67 | 0.87 | NA | NA |
| Pyocyanin | Moxifloxacin | 0.58 | 0.30 | 0.25 | 0.88 | NA | NA |
| Oxacillin | Cefaclor | −0.69 | −0.71 | NA | NA | NA | NA |
| Nitrofurantoin | Tobramycin | −0.22 | −0.66 | NA | NA | 0.16 | 0.02 |
| Polymyxin B | Curcumin | −0.65 | −0.62 | NA | NA | NA | NA |
| Procaine | Puromycin | −0.63 | −0.58 | NA | NA | NA | NA |
| Spiramycin | Colistin | −0.71 | −0.52 | NA | NA | NA | NA |
| Procaine | Bleomycin | −0.43 | −0.44 | NA | NA | NA | NA |
| Chloramphenicol | Nitrofurantoin | 0.06 | −0.42 | NA | NA | 0.08 | 0.12 |
| Benzalkonium | Procaine | −0.28 | −0.41 | NA | NA | −0.05 | −0.24 |
| Cefsulodin | Aztreonam | −0.56 | −0.41 | NA | NA | −0.09 | −0.55 |
| Polymyxin B | Triclosan | −0.76 | −0.38 | NA | NA | NA | NA |
| Amikacin | Clindamycin | 0.35 | −0.06 | NA | NA | NA | NA |
| Erythromycin | Tobramycin | 0.37 | −0.04 | NA | NA | 0.46 | 0.38 |
| Tobramycin | Metformin | 0.41 | 0.03 | NA | NA | NA | NA |
| A22 | Colistin | 0.47 | 0.05 | NA | NA | −0.04 | −0.38 |
| Clindamycin | Tobramycin | 0.74 | 0.05 | NA | NA | NA | NA |
| Polymyxin B | Cefaclor | 0.31 | 0.07 | NA | NA | NA | NA |
| Fosfomycin | Mitomycin C | 0.27 | 0.14 | NA | NA | −0.22 | 0.27 |
| Fosfomycin | Erythromycin | 0.24 | 0.14 | NA | NA | −0.16 | −0.04 |
| Rifampicin | Gentamicin | 0.30 | 0.16 | NA | NA | NA | NA |
| Rifampicin | Phleomycin | 0.38 | 0.17 | NA | NA | 0.15 | 0.03 |
| Fosfomycin | Clarithromycin | 0.30 | 0.25 | NA | NA | −0.26 | −0.34 |
| Spectinomycin | Fosfomycin | 0.35 | 0.30 | NA | NA | NA | NA |
| Fosfomycin | Trimethoprim | 0.27 | 0.30 | NA | NA | NA | NA |
| Vanillin | CHIR-90 | 0.38 | 0.32 | NA | NA | NA | NA |
| A22 | Acetylsalisylic acid | 0.40 | 0.32 | NA | NA | NA | NA |
| Ciprofloxacin | Caffeine | 0.37 | 0.36 | NA | NA | NA | NA |
| Aztreonam | Berberine | 0.21 | 0.43 | NA | NA | NA | NA |
| Amoxicillin | Vanillin | 0.18 | 0.49 | NA | NA | NA | NA |
| Aztreonam | Curcumin | 0.53 | 0.56 | NA | NA | NA | NA |
| Benzalkonium | Curcumin | 0.16 | 0.93 | NA | NA | 0.54 | 0.68 |
| Polymyxin B | Chlorhexidine | NA | NA | NA | NA | −0.61 | −0.62 |
| Cefotaxime | Metformin | NA | NA | NA | NA | −0.43 | −0.48 |
| Procaine | Levofloxacin | NA | NA | NA | NA | −0.35 | <0.005 |
| Procaine | Minocycline | NA | NA | NA | NA | −0.33 | <0.005 |
| Loperamide | Clarithromycin | NA | NA | NA | NA | −0.31 | 0.09 |
| Amoxicillin | Gentamicin | NA | NA | NA | NA | −0.38 | −0.13 |
| Ciprofloxacin | Metformin | NA | NA | NA | NA | −0.26 | 0.11 |
| Bacitracin | Gentamicin | NA | NA | NA | NA | −0.38 | −0.08 |
| Cefotaxime | Tobramycin | NA | NA | NA | NA | −0.45 | −0.08 |
| Cefotaxime | Gentamicin | NA | NA | NA | NA | −0.34 | −0.07 |
| Loperamide | Gentamicin | NA | NA | NA | NA | −0.31 | −0.73 |
| Minocycline | Colistin | NA | NA | NA | NA | −0.26 | −0.34 |
| Chlorhexidine | Colistin | NA | NA | NA | NA | −0.78 | −0.83 |
| Chlorhexidine | Moxifloxacin | NA | NA | NA | NA | −0.68 | −0.63 |
| Aztreonam | Clarithromycin | NA | NA | NA | NA | −0.31 | −0.19 |
| Ciprofloxacin | Berberine | NA | NA | NA | NA | 0.29 | 0.43 |
| Amikacin | Acetylsalisylic acid | NA | NA | NA | NA | 0.40 | 0.07 |
| Amikacin | Phleomycin | NA | NA | NA | NA | 0.33 | 0.10 |
| Benzalkonium | Azithromycin | NA | NA | NA | NA | 0.37 | 0.31 |
| Cefsulodin | Loperamide | NA | NA | NA | NA | 0.26 | 0.50 |
| Levofloxacin | Berberine | NA | NA | NA | NA | 0.36 | 0.71 |
| Piperacillin | fmipenem | NA | NA | NA | NA | 0.57 | −0.06 |
| Nitrofurantoin | Gentamicin | NA | NA | NA | NA | 0.39 | <0.005 |
| Minocycline | Gentamicin | NA | NA | NA | NA | 0.33 | 0.37 |
| Tobramycin | Clarithromycin | NA | NA | NA | NA | 0.45 | 0.19 |
| Tobramycin | Azithromycin | NA | NA | NA | NA | 0.55 | 0.10 |

TABLE 1-continued

| Drug-drug interactions detected in the screen. | | | | | | | |
|---|---|---|---|---|---|---|---|
| Tobramycin | Acetylsalisylic acid | NA | NA | NA | NA | 0.59 | 0.67 |
| EGCG | Colistin | NA | NA | NA | NA | 0.37 | 0.04 |
| Chloramphenicol | Cefsulodin | NA | NA | NA | NA | 0.46 | 0.04 |
| Cefsulodin | Cephalexin | NA | NA | NA | NA | 0.38 | 0.04 |
| Cefsulodin | Linezolid | NA | NA | NA | NA | 0.28 | 0.30 |
| Procaine | Chlorhexidine | NA | NA | NA | NA | −0.16 | −0.39 |
| Piperacillin | Metformin | NA | NA | NA | NA | −0.40 | −0.51 |
| Chloramphenicol | Tobramycin | NA | NA | NA | NA | 0.03 | 0.41 |
| Doxycycline | Gentamicin | NA | NA | NA | NA | 0.12 | 0.50 |
| Benzalkonium | Levofloxacin | NA | NA | NA | NA | −0.04 | 0.49 |
| Flucytosine | Mitomycin C | NA | NA | NA | NA | −0.12 | −0.13 |
| Colistin | Phenformin | NA | NA | NA | NA | −0.21 | −0.45 |
| Piperacillin | Flucytosine | NA | NA | NA | NA | 0.24 | 0.72 |
| Tobramycin | Flucytosine | NA | NA | NA | NA | 0.13 | 0.50 |
| Aztreonam | Imipenem | NA | NA | NA | NA | 0.41 | −0.24 |
| Colistin | Gentamicin | NA | NA | NA | NA | 0.44 | 0.26 |

| Drug combination | | $p_{permutations}$ | | | | | |
|---|---|---|---|---|---|---|---|
| | | E. coli | E. coli | ST | ST | | |
| Drug 1 | Drug 2 | BW25113 | iAi1 | LT2 | 14028 | PAO1 | PA14 |
| Bacitracin | Colistin | <0.005 | <0.005 | <0.005 | <0.005 | <0.005 | <0.005 |
| Rifampicin | CHIR-90 | NA | 0.03 | 0.03 | <0.005 | NA | NA |
| Benzalkonium | Colistin | <0.005 | <0.005 | <0.005 | <0.005 | <0.005 | <0.005 |
| Rifampicin | Colistin | <0.005 | 0.02 | <0.005 | <0.005 | <0.005 | <0.005 |
| Pseudomonic acid | Colistin | <0.005 | <0.005 | <0.005 | <0.005 | NA | NA |
| Fusidic acid | Colistin | <0.005 | <0.005 | <0.005 | <0.005 | NA | 0.01 |
| Polymyxin B | Benzalkonium | <0.005 | <0.005 | <0.005 | <0.005 | <0.005 | <0.005 |
| Loperamide | Colistin | <0.005 | <0.005 | NA | <0.005 | <0.005 | <0.005 |
| Novobiocin | Colistin | <0.005 | <0.005 | <0.005 | <0.005 | NA | 0.02 |
| Cefaclor | Meropenem | NA | NA | NA | <0.005 | NA | NA |
| Clarithromycin | Colistin | <0.005 | <0.005 | <0.005 | <0.005 | 0.01 | 0.01 |
| Minocycline | Chlorhexidine | NA | NA | 0.03 | <0.005 | <0.005 | <0.005 |
| Chlorhexidine | Rifampicin | NA | NA | NA | 0.01 | NA | NA |
| Erythromycin | Colistin | <0.005 | <0.005 | <0.005 | <0.005 | NA | <0.005 |
| Chlorhexidine | Pseudomonic acid | NA | NA | NA | 0.02 | NA | NA |
| Fusidic acid | Metformin | NA | NA | <0.005 | <0.005 | NA | NA |
| Mecillinam | Meropenem | NA | NA | NA | 0.01 | NA | NA |
| Chlorhexidine | Clarithromycin | NA | NA | NA | <0.005 | NA | NA |
| Fusidic acid | CHIR-90 | 0.04 | <0.005 | 0.04 | <0.005 | NA | NA |
| Polymyxin B | Rifampicin | NA | 0.02 | <0.005 | <0.005 | 0.02 | 0.02 |
| Levofloxacin | Chlorhexidine | NA | NA | 0.01 | <0.005 | <0.005 | NA |
| Cycloserine D | Mecillinam | NA | NA | 0.03 | <0.005 | NA | NA |
| PMS | Meropenem | NA | NA | 0.02 | 0.01 | NA | NA |
| Pyocyanin | Meropenem | NA | NA | 0.02 | <0.005 | NA | NA |
| CCCP | Colistin | <0.005 | NA | <0.005 | NA | NA | NA |
| Rifampicin | Streptozotocin | NA | NA | 0.01 | <0.005 | NA | NA |
| Cefaclor | Mecillinam | <0.005 | <0.005 | 0.02 | <0.005 | NA | NA |
| Amoxicillin | Piperacillin | <0.005 | <0.005 | <0.005 | <0.005 | <0.005 | NA |
| Amoxicillin | Aztreonam | <0.005 | <0.005 | 0.02 | 0.05 | NA | NA |
| Bacitracin | CHIR-90 | 0.01 | 0.01 | 0.02 | <0.005 | NA | NA |
| Novobiocin | Chlorhexidine | NA | NA | 0.01 | <0.005 | <0.005 | <0.005 |
| Nitrofurantoin | Phleomycin | <0.005 | <0.005 | 0.02 | <0.005 | NA | NA |
| Cefaclor | Aztreonam | <0.005 | <0.005 | <0.005 | 0.01 | NA | NA |
| Chlorhexidine | Cerulenin | NA | NA | NA | NA | 0.01 | NA |
| Piperacillin | Mecillinam | NA | NA | <0.005 | <0.005 | NA | NA |
| Mecillinam | Aztreonam | NA | NA | <0.005 | <0.005 | NA | NA |
| Doxycycline | Metformin | NA | NA | <0.005 | <0.005 | NA | <0.005 |
| Penicillin G | Meropenem | NA | NA | NA | <0.005 | NA | NA |
| Verapamil | Colistin | <0.005 | <0.005 | <0.005 | 0.01 | <0.005 | <0.005 |
| Doxycycline | Benzalkonium | NA | NA | <0.005 | <0.005 | NA | NA |
| Spectinomycin | Vanillin | <0.005 | <0.005 | <0.005 | <0.005 | NA | NA |
| Bleomycin | CHIR-90 | NA | <0.005 | NA | <0.005 | NA | NA |
| Bacitracin | Polymyxin B | NA | NA | NA | 0.03 | <0.005 | <0.005 |
| Verapamil | CHIR-90 | 0.03 | <0.005 | NA | <0.005 | NA | NA |
| Bleomycin | Colistin | <0.005 | 0.04 | NA | 0.05 | NA | NA |
| Pyocyanin | Imipenem | NA | NA | <0.005 | <0.005 | NA | NA |
| Cerulenin | Colistin | 0.04 | NA | <0.005 | 0.02 | NA | NA |
| Chlorhexidine | Pyocyanin | NA | NA | <0.005 | 0.01 | NA | NA |
| Polymyxin B | Fusidic acid | <0.005 | <0.005 | 0.02 | NA | NA | NA |
| Doxycycline | CHIR-90 | NA | 0.01 | 0.02 | <0.005 | NA | NA |
| Cefaclor | Penicillin G | NA | NA | 0.04 | 0.02 | <0.005 | NA |
| Clarithromycin | CHIR-90 | 0.05 | <0.005 | NA | 0.01 | NA | NA |
| Piperacillin | Tobramycin | NA | NA | 0.02 | <0.005 | <0.005 | 0.05 |
| Novobiocin | Polymyxin B | <0.005 | <0.005 | <0.005 | <0.005 | NA | NA |
| Procaine | Azithromycin | <0.005 | <0.005 | <0.005 | 0.01 | NA | NA |

TABLE 1-continued

| | | | | | | |
|---|---|---|---|---|---|---|
| | | Drug-drug interactions detected in the screen. | | | | |
| Doxycycline | Procaine | NA | NA | <0.005 | NA | <0.005 | <0.005 |
| Procaine | Phleomycin | <0.005 | <0.005 | NA | <0.005 | NA | NA |
| Procaine | Piperacillin | NA | NA | <0.005 | 0.01 | NA | NA |
| Procaine | Moxifloxacin | NA | NA | <0.005 | NA | NA | NA |
| Novobiocin | Bacitracin | <0.005 | 0.01 | NA | <0.005 | NA | NA |
| Pyocyanin | Acetylsalisylic acid | <0.005 | NA | <0.005 | NA | NA | NA |
| Bleomycin | Streptozotocin | <0.005 | NA | <0.005 | <0.005 | NA | NA |
| Procaine | Pyocyanin | <0.005 | NA | <0.005 | <0.005 | NA | NA |
| Tobramycin | Aztreonam | NA | NA | NA | 0.02 | <0.005 | 0.03 |
| PMS | Streptozotocin | NA | NA | <0.005 | 0.01 | NA | NA |
| Benzalkonium | EGCG | NA | <0.005 | NA | <0.005 | NA | <0.005 |
| Amikacin | Aztreonam | NA | NA | 0.01 | 0.03 | <0.005 | <0.005 |
| Paraquat | Streptozotocin | NA | NA | <0.005 | 0.02 | NA | NA |
| PMS | Acetylsalisylic acid | <0.005 | NA | <0.005 | NA | NA | NA |
| Trimethoprim | Sulfamonomethoxine | <0.005 | <0.005 | <0.005 | 0.04 | NA | NA |
| Amikacin | PMS | <0.005 | NA | <0.005 | <0.005 | NA | NA |
| Fosfomycin | Cefsulodin | <0.005 | <0.005 | <0.005 | NA | NA | NA |
| Fosfomycin | Vanillin | <0.005 | <0.005 | 0.01 | NA | NA | NA |
| Amikacin | Puromycin | <0.005 | <0.005 | 0.01 | NA | NA | NA |
| Fusidic acid | Azithromycin | NA | NA | <0.005 | NA | NA | NA |
| Nitrofurantoin | Streptozotocin | NA | NA | <0.005 | NA | NA | NA |
| Amikacin | Pyocyanin | <0.005 | NA | <0.005 | NA | NA | NA |
| Amikacin | Streptozotocin | NA | NA | <0.005 | NA | NA | NA |
| Doxycycline | Spectinomycin | NA | NA | <0.005 | NA | NA | NA |
| PMS | Rifampicin | <0.005 | NA | <0.005 | NA | NA | NA |
| Procaine | Rifampicin | <0.005 | <0.005 | 0.01 | NA | NA | NA |
| PMS | Pyocyanin | NA | NA | <0.005 | NA | NA | NA |
| Cycloserine D | Paraquat | NA | NA | <0.005 | NA | NA | NA |
| Pyocyanin | Gentamicin | <0.005 | NA | <0.005 | NA | NA | NA |
| Cycloserine D | Tobramycin | NA | NA | <0.005 | NA | NA | NA |
| Levofloxacin | Metformin | NA | NA | 0.05 | NA | <0.005 | NA |
| Rifampicin | Cerulenin | <0.005 | <0.005 | 0.01 | NA | NA | NA |
| Cefsulodin | Piperacillin | <0.005 | <0.005 | 0.02 | NA | NA | NA |
| PMS | Gentamicin | <0.005 | 0.02 | <0.005 | NA | NA | NA |
| Pyocyanin | Phleomycin | <0.005 | <0.005 | <0.005 | NA | NA | NA |
| Pyocyanin | Bleomycin | <0.005 | NA | <0.005 | NA | NA | NA |
| Amikacin | Procaine | <0.005 | NA | <0.005 | NA | <0.005 | 0.05 |
| Benzalkonium | Tobramycin | NA | NA | <0.005 | NA | NA | NA |
| Fosfomycin | Novobiocin | <0.005 | <0.005 | <0.005 | NA | <0.005 | NA |
| Penicillin G | Pyocyanin | NA | NA | <0.005 | NA | NA | NA |
| PMS | Bleomycin | <0.005 | 0.02 | <0.005 | NA | NA | NA |
| Novobiocin | Fusidic acid | NA | <0.005 | NA | 0.01 | NA | NA |
| Paraquat | Puromycin | NA | <0.005 | NA | <0.005 | NA | NA |
| PMS | Phleomycin | <0.005 | <0.005 | <0.005 | NA | NA | NA |
| Doxycycline | Fosfomycin | <0.005 | <0.005 | <0.005 | NA | NA | NA |
| Paraquat | Phleomycin | NA | NA | <0.005 | NA | NA | NA |
| Pyocyanin | Mitomycin C | 0.05 | <0.005 | <0.005 | <0.005 | NA | NA |
| Aztreonam | Caffeine | <0.005 | NA | NA | 0.01 | NA | NA |
| Procaine | Gentamicin | <0.005 | NA | <0.005 | NA | NA | NA |
| Doxycycline | Vanillin | <0.005 | <0.005 | NA | <0.005 | NA | NA |
| PMS | Azithromycin | <0.005 | NA | NA | <0.005 | NA | NA |
| Ciprofloxacin | Doxycycline | NA | <0.005 | <0.005 | NA | NA | <0.005 |
| Paraquat | Piperacillin | NA | NA | 0.03 | <0.005 | NA | <0.005 |
| Chloramphenicol | Ciprofloxacin | NA | NA | <0.005 | NA | NA | <0.005 |
| Ciprofloxacin | Benzalkonium | 0.02 | <0.005 | NA | 0.01 | NA | <0.005 |
| Ciprofloxacin | PMS | <0.005 | 0.01 | <0.005 | 0.01 | NA | NA |
| Mecillinam | Metformin | <0.005 | NA | NA | 0.01 | NA | NA |
| Doxycycline | Mecillinam | <0.005 | <0.005 | <0.005 | <0.005 | NA | NA |
| Mecillinam | Pyocyanin | <0.005 | NA | NA | <0.005 | NA | NA |
| Doxycycline | PMS | <0.005 | <0.005 | <0.005 | <0.005 | NA | NA |
| Doxycycline | Pyocyanin | <0.005 | <0.005 | <0.005 | <0.005 | NA | NA |
| Novobiocin | Paraquat | NA | <0.005 | NA | <0.005 | NA | NA |
| Novobiocin | Vanillin | NA | <0.005 | NA | <0.005 | NA | NA |
| Amikacin | Benzalkonium | <0.005 | NA | <0.005 | 0.01 | NA | NA |
| Vanillin | Moxifloxacin | 0.02 | <0.005 | NA | 0.02 | NA | NA |
| Ciprofloxacin | Pyocyanin | <0.005 | NA | <0.005 | 0.01 | NA | NA |
| PMS | CHIR-90 | <0.005 | <0.005 | <0.005 | NA | NA | NA |
| Novobiocin | PMS | <0.005 | <0.005 | NA | <0.005 | NA | NA |
| Benzalkonium | Gentamicin | NA | <0.005 | NA | 0.05 | NA | NA |
| Cerulenin | CHIR-90 | <0.005 | <0.005 | <0.005 | 0.01 | NA | NA |
| Paraquat | CHIR-90 | <0.005 | <0.005 | 0.03 | 0.01 | NA | NA |
| Pyocyanin | CHIR-90 | <0.005 | NA | <0.005 | 0.01 | NA | NA |
| Nitrofurantoin | Aztreonam | NA | NA | NA | <0.005 | NA | NA |
| Procaine | Aztreonam | <0.005 | <0.005 | <0.005 | <0.005 | NA | NA |
| Paraquat | Moxifloxacin | NA | <0.005 | NA | 0.01 | NA | NA |
| EGCG | Moxifloxacin | 0.02 | <0.005 | NA | 0.04 | NA | NA |
| Paraquat | Levofloxacin | NA | NA | <0.005 | <0.005 | NA | NA |
| PMS | Aztreonam | <0.005 | NA | <0.005 | <0.005 | NA | NA |

TABLE 1-continued

| Drug-drug interactions detected in the screen. | | | | | | | |
|---|---|---|---|---|---|---|---|
| Cefaclor | Metformin | NA | NA | NA | <0.005 | NA | NA |
| Cefaclor | Colistin | NA | NA | <0.005 | 0.02 | NA | NA |
| Levofloxacin | Acetylsalisylic acid | <0.005 | <0.005 | <0.005 | NA | NA | NA |
| PMS | Levofloxacin | <0.005 | NA | <0.005 | <0.005 | NA | NA |
| Aztreonam | Acetylsalisylic acid | <0.005 | <0.005 | <0.005 | 0.04 | NA | NA |
| Levofloxacin | Pyocyanin | <0.005 | <0.005 | <0.005 | <0.005 | NA | NA |
| PMS | Moxifloxacin | <0.005 | <0.005 | 0.05 | <0.005 | NA | NA |
| Ciprofloxacin | Paraquat | 0.01 | <0.005 | <0.005 | <0.005 | NA | NA |
| Paraquat | Aztreonam | NA | NA | <0.005 | <0.005 | <0.005 | NA |
| Ciprofloxacin | Vanillin | <0.005 | <0.005 | <0.005 | <0.005 | NA | NA |
| Vanillin | Aztreonam | <0.005 | <0.005 | <0.005 | <0.005 | NA | 0.01 |
| Aztreonam | Pyocyanin | <0.005 | <0.005 | <0.005 | <0.005 | NA | NA |
| Pyocyanin | Moxifloxacin | 0.02 | <0.005 | <0.005 | <0.005 | NA | NA |
| Oxacillin | Cefaclor | <0.005 | <0.005 | NA | NA | NA | NA |
| Nitrofurantoin | Tobramycin | <0.005 | NA | NA | NA | <0.005 | NA |
| Polymyxin B | Curcumin | 0.03 | NA | NA | NA | NA | NA |
| Procaine | Puromycin | <0.005 | <0.005 | NA | NA | NA | NA |
| Spiramycin | Colistin | <0.005 | 0.04 | NA | NA | NA | NA |
| Procaine | Bleomycin | <0.005 | <0.005 | NA | NA | NA | NA |
| Chloramphenicol | Nitrofurantoin | NA | <0.005 | NA | NA | NA | <0.005 |
| Benzalkonium | Procaine | <0.005 | <0.005 | NA | NA | NA | <0.005 |
| Cefsulodin | Aztreonam | <0.005 | <0.005 | NA | NA | NA | 0.01 |
| Polymyxin B | Triclosan | 0.03 | NA | NA | NA | NA | NA |
| Amikacin | Clindamycin | <0.005 | NA | NA | NA | NA | NA |
| Erythromycin | Tobramycin | <0.005 | NA | NA | NA | <0.005 | <0.005 |
| Tobramycin | Metformin | <0.005 | NA | NA | NA | NA | NA |
| A22 | Colistin | 0.04 | NA | NA | NA | NA | <0.005 |
| Clindamycin | Tobramycin | <0.005 | NA | NA | NA | NA | NA |
| Polymyxin B | Cefaclor | <0.005 | NA | NA | NA | NA | NA |
| Fosfomycin | Mitomycin C | <0.005 | 0.03 | NA | NA | <0.005 | <0.005 |
| Fosfomycin | Erythromycin | <0.005 | <0.005 | NA | NA | <0.005 | NA |
| Rifampicin | Gentamicin | <0.005 | NA | NA | NA | NA | NA |
| Rifampicin | Phleomycin | <0.005 | NA | NA | NA | 0.02 | NA |
| Fosfomycin | Clarithromycin | <0.005 | <0.005 | NA | NA | <0.005 | 0.04 |
| Spectinomycin | Fosfomycin | <0.005 | <0.005 | NA | NA | NA | NA |
| Fosfomycin | Trimethoprim | <0.005 | <0.005 | NA | NA | NA | NA |
| Vanillin | CHIR-90 | <0.005 | 0.01 | NA | NA | NA | NA |
| A22 | Acetylsalisylic acid | <0.005 | <0.005 | NA | NA | NA | NA |
| Ciprofloxacin | Caffeine | 0.01 | <0.005 | NA | NA | NA | NA |
| Aztreonam | Berberine | <0.005 | <0.005 | NA | NA | NA | NA |
| Amoxicillin | Vanillin | 0.04 | <0.005 | NA | NA | NA | NA |
| Aztreonam | Curcumin | <0.005 | <0.005 | NA | NA | NA | NA |
| Benzalkonium | Curcumin | NA | <0.005 | NA | NA | <0.005 | <0.005 |
| Polymyxin B | Chlorhexidine | NA | NA | NA | NA | <0.005 | <0.005 |
| Cefotaxime | Metformin | NA | NA | NA | NA | <0.005 | 0.01 |
| Procaine | Levofloxacin | NA | NA | NA | NA | <0.005 | NA |
| Procaine | Minocycline | NA | NA | NA | NA | <0.005 | NA |
| Loperamide | Clarithromycin | NA | NA | NA | NA | <0.005 | NA |
| Amoxicillin | Gentamicin | NA | NA | NA | NA | 0.01 | NA |
| Ciprofloxacin | Metformin | NA | NA | NA | NA | 0.01 | NA |
| Bacitracin | Gentamicin | NA | NA | NA | NA | 0.01 | NA |
| Cefotaxime | Tobramycin | NA | NA | NA | NA | <0.005 | NA |
| Cefotaxime | Gentamicin | NA | NA | NA | NA | 0.05 | NA |
| Loperamide | Gentamicin | NA | NA | NA | NA | 0.04 | 0.01 |
| Minocycline | Colistin | NA | NA | NA | NA | 0.02 | <0.005 |
| Chlorhexidine | Colistin | NA | NA | NA | NA | <0.005 | <0.005 |
| Chlorhexidine | Moxifloxacin | NA | NA | NA | NA | 0.04 | 0.01 |
| Aztreonam | Clarithromycin | NA | NA | NA | NA | <0.005 | NA |
| Ciprofloxacin | Berberine | NA | NA | NA | NA | <0.005 | <0.005 |
| Amikacin | Acetylsalisylic acid | NA | NA | NA | NA | <0.005 | NA |
| Amikacin | Phleomycin | NA | NA | NA | NA | <0.005 | NA |
| Benzalkonium | Azithromycin | NA | NA | NA | NA | <0.005 | <0.005 |
| Cefsulodin | Loperamide | NA | NA | NA | NA | <0.005 | <0.005 |
| Levofloxacin | Berberine | NA | NA | NA | NA | 0.01 | <0.005 |
| Piperacillin | Imipenem | NA | NA | NA | NA | <0.005 | NA |
| Nitrofurantoin | Gentamicin | NA | NA | NA | NA | <0.005 | NA |
| Minocycline | Gentamicin | NA | NA | NA | NA | <0.005 | NA |
| Tobramycin | Clarithromycin | NA | NA | NA | NA | <0.005 | <0.005 |
| Tobramycin | Azithromycin | NA | NA | NA | NA | 0.01 | NA |
| Tobramycin | Acetylsalisylic acid | NA | NA | NA | NA | <0.005 | 0.01 |
| EGCG | Colistin | NA | NA | NA | NA | <0.005 | NA |
| Chloramphenicol | Cefsulodin | NA | NA | NA | NA | <0.005 | NA |
| Cefsulodin | Cephalexin | NA | NA | NA | NA | <0.005 | NA |
| Cefsulodin | Linezolid | NA | NA | NA | NA | <0.005 | 0.05 |
| Procaine | Chlorhexidine | NA | NA | NA | NA | NA | <0.005 |
| Piperacillin | Metformin | NA | NA | NA | NA | NA | <0.005 |
| Chloramphenicol | Tobramycin | NA | NA | NA | NA | NA | <0.005 |
| Doxycycline | Gentamicin | NA | NA | NA | NA | NA | <0.005 |

TABLE 1-continued

| Drug-drug interactions detected in the screen. | | | | | | | |
| --- | --- | --- | --- | --- | --- | --- | --- |
| Benzalkonium | Levofloxacin | NA | NA | NA | NA | NA | <0.005 |
| Flucytosine | Mitomycin C | NA | NA | NA | NA | <0.005 | 0.05 |
| Colistin | Phenformin | NA | NA | NA | NA | 0.05 | <0.005 |
| Piperacillin | Flucytosine | NA | NA | NA | NA | <0.005 | <0.005 |
| Tobramycin | Flucytosine | NA | NA | NA | NA | <0.005 | <0.005 |
| Aztreonam | Imipenem | NA | NA | NA | NA | <0.005 | <0.005 |
| Colistin | Gentamicin | NA | NA | NA | NA | <0.005 | NA |

Abbreviations: 'Anta' = antagonism; 'Syn' = synergy; 'NA' = data not available.

The invention claimed is:

1. An antibacterial pharmaceutical composition, comprising:
   (i) vanillin or a pharmaceutically acceptable salt thereof, or a structural related vanillin derivative or a pharmaceutically acceptable salt thereof, and
   (ii) at least one additional antibacterial drug compound, or a pharmaceutically acceptable salt (ii) thereof, or a pharmaceutically acceptable salt thereof, wherein the composition is at an effective amount to yield synergies for antibacterial activity.

2. The composition according to claim 1, wherein said at least one additional anti-bacterial drug compound is spectinomycin.

* * * * *